US010231939B2

(12) United States Patent
McCord et al.

(10) Patent No.: US 10,231,939 B2
(45) Date of Patent: *Mar. 19, 2019

(54) HYDROXYTYROSOL AND OLEUROPEIN COMPOSITIONS FOR INDUCTION OF DNA DAMAGE, CELL DEATH AND LSD1 INHIBITION

(71) Applicant: Darlene E. McCord, Coralville, IA (US)

(72) Inventors: Darlene E. McCord, Coralville, IA (US); Thomas Karagiannis, Melbourne (AU)

(73) Assignee: Darlene E. McCord, Coralville, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/496,866

(22) Filed: Apr. 25, 2017

(65) Prior Publication Data

US 2017/0224633 A1    Aug. 10, 2017

Related U.S. Application Data

(63) Continuation of application No. 14/823,028, filed on Aug. 11, 2015, now Pat. No. 9,662,302, which is a continuation of application No. 14/091,742, filed on Nov. 27, 2013, now Pat. No. 9,144,555.

(60) Provisional application No. 61/819,226, filed on May 3, 2013, provisional application No. 61/731,598, filed on Nov. 30, 2012.

(51) Int. Cl.
| | |
|---|---|
| *A61K 31/05* | (2006.01) |
| *A61K 31/704* | (2006.01) |
| *A61K 31/7048* | (2006.01) |
| *A61K 31/22* | (2006.01) |
| *C12Q 1/6876* | (2018.01) |
| *G01N 33/574* | (2006.01) |
| *C12Q 1/26* | (2006.01) |
| *A61K 45/06* | (2006.01) |

(52) U.S. Cl.
CPC .............. *A61K 31/05* (2013.01); *A61K 31/22* (2013.01); *A61K 31/704* (2013.01); *A61K 31/7048* (2013.01); *A61K 45/06* (2013.01); *C12Q 1/26* (2013.01); *C12Q 1/6876* (2013.01); *G01N 33/574* (2013.01); *A61K 2300/00* (2013.01)

(58) Field of Classification Search
CPC ...... A61K 31/05; A61K 31/22; A61K 31/704; A61K 31/7048; A61K 45/06; C12Q 1/26; C12Q 1/6876; G01N 33/574
USPC ................. 514/1, 1.1, 27, 34, 731; 568/766
See application file for complete search history.

(56) References Cited

U.S. PATENT DOCUMENTS

| | | |
|---|---|---|
| 6,117,844 A | 9/2000 | Fredrickson |
| 6,165,475 A | 12/2000 | Crea et al. |
| 6,179,819 B1 | 1/2001 | Haswell |
| 6,197,308 B1 | 3/2001 | Crea et al. |
| 6,309,652 B1 | 10/2001 | Aeschbach et al. |
| 6,358,542 B2 | 3/2002 | Cuomo et al. |
| 6,416,808 B1 | 7/2002 | Crea |
| 6,437,004 B1 | 8/2002 | Perricone |
| 6,746,706 B1 | 6/2004 | van der Boom et al. |
| 7,045,148 B2 | 5/2006 | Hariri |
| 7,468,276 B2 | 12/2008 | Hariri |
| 7,682,803 B2 | 3/2010 | Paludan et al. |
| 7,976,836 B2 | 7/2011 | Hariri |
| 8,034,329 B2 | 10/2011 | Colter et al. |
| 8,105,634 B2 | 1/2012 | Liu et al. |
| 8,142,806 B2 | 3/2012 | Gupta et al. |
| 8,202,703 B2 | 6/2012 | Edinger et al. |
| 8,216,566 B2 | 7/2012 | Paludan et al. |
| 8,216,599 B2 | 7/2012 | Crea |
| 8,278,102 B2 | 10/2012 | Ennis et al. |
| 8,293,223 B2 | 10/2012 | Hariri |
| 8,309,070 B2 | 11/2012 | Low et al. |
| 8,809,311 B2 | 8/2014 | McCord |

(Continued)

FOREIGN PATENT DOCUMENTS

| | | |
|---|---|---|
| CN | 102397268 A | 4/2012 |
| EP | 0123637 A1 | 4/1984 |

(Continued)

OTHER PUBLICATIONS

Schmidt et al., "trans-2-Phenylcyclopropylamine Is a Mechanism-Based Inactivator of the Histone Demethylase LSD1", 2007, Biochemistry, 46(14), pp. 4408-4416. (Year: 2007).*

(Continued)

*Primary Examiner* — My-Chau T. Tran
(74) *Attorney, Agent, or Firm* — McKee, Voorhees & Sease, PLC

(57) ABSTRACT

Compositions comprising hydroxytyrosol-containing formulations and treatment regiments comprising hydroxytyrosol and/or oleuropein and chemotherapeutic agents are disclosed. Compositions and/or regiments may optionally include the administration of vitamins, minerals, and antioxidants. Methods for using these compositions and treatment regimens for treating subjects for diseases, such as a malignancy, and for inducing or enhancing angiogenesis, treating or preventing oxidative stress, for treating or preventing high glucose-induced dysfunction, treating or preventing chemotherapy-induced dysfunction, and for improving cell viability are provided. Various methods for use of the hydroxytyrosol compositions for inhibition of lysine specific demethylase 1 (LSD1) in various cancers are also provided.

7 Claims, 49 Drawing Sheets

(56) References Cited

U.S. PATENT DOCUMENTS

| | | | |
|---|---|---|---|
| 8,993,808 B2* | 3/2015 | Guibourt | C07C 211/40 564/384 |
| 9,144,555 B2* | 9/2015 | McCord | A61K 31/05 |
| 9,532,970 B2* | 1/2017 | McCord | A61K 45/06 |
| 9,662,302 B2* | 5/2017 | McCord | A61K 31/05 |
| 2003/0032179 A1 | 2/2003 | Hariri | |
| 2004/0101507 A1 | 5/2004 | Predovan | |
| 2006/0120980 A1 | 6/2006 | Eberl | |
| 2006/0121133 A1 | 6/2006 | Chomczynski | |
| 2007/0053888 A1 | 3/2007 | Hariri | |
| 2007/0065396 A1 | 3/2007 | Morariu | |
| 2007/0110727 A1 | 5/2007 | Kang | |
| 2007/0178073 A1 | 8/2007 | Chang et al. | |
| 2007/0207228 A1 | 9/2007 | Giuliani et al. | |
| 2007/0298017 A1 | 12/2007 | Han | |
| 2008/0032401 A1 | 2/2008 | Edinger et al. | |
| 2008/0152629 A1 | 6/2008 | Edinger et al. | |
| 2008/0226595 A1 | 9/2008 | Edinger et al. | |
| 2008/0306037 A1 | 12/2008 | Medina Montano | |
| 2008/0311087 A1 | 12/2008 | Gosiewska et al. | |
| 2008/0311088 A1 | 12/2008 | Chang et al. | |
| 2009/0048187 A1 | 2/2009 | Ricciardiello et al. | |
| 2009/0053805 A1 | 2/2009 | Hariri | |
| 2009/0104650 A1 | 4/2009 | Walton et al. | |
| 2009/0232781 A1 | 9/2009 | Fu | |
| 2009/0232782 A1 | 9/2009 | Fu | |
| 2009/0280093 A1 | 11/2009 | Friedlander | |
| 2010/0068194 A1 | 3/2010 | Kim | |
| 2010/0113611 A1 | 5/2010 | Raederstoriff et al. | |
| 2010/0143289 A1 | 6/2010 | Cohen et al. | |
| 2011/0014308 A1 | 1/2011 | Raederstorff et al. | |
| 2011/0136751 A1 | 6/2011 | Estrela et al. | |
| 2011/0217271 A1 | 9/2011 | Hariri | |
| 2011/0223205 A1 | 9/2011 | Gosiewska et al. | |
| 2011/0280843 A1 | 11/2011 | Edinger et al. | |
| 2012/0107294 A1 | 5/2012 | Kim | |
| 2012/0114712 A1 | 5/2012 | Liu et al. | |
| 2012/0189583 A1 | 7/2012 | Liu et al. | |
| 2012/0192873 A1 | 8/2012 | Bachmann | |
| 2012/0213743 A1 | 8/2012 | Buensuceso et al. | |
| 2013/0005682 A1 | 1/2013 | Raederstorff et al. | |
| 2013/0039893 A1 | 2/2013 | Phan | |
| 2014/0194530 A1 | 7/2014 | Xu et al. | |
| 2014/0194531 A1 | 7/2014 | Liu et al. | |
| 2016/0045519 A1 | 2/2016 | Horcajada et al. | |
| 2017/0065549 A1* | 3/2017 | McCord | A61K 45/06 |

FOREIGN PATENT DOCUMENTS

| | | |
|---|---|---|
| EP | 2070545 A1 | 6/2009 |
| JP | 2007119431 A | 5/2007 |
| WO | 20000036936 A2 | 6/2000 |
| WO | 2004032873 A2 | 4/2004 |
| WO | 2004053067 A2 | 6/2004 |
| WO | 2006020588 A1 | 2/2006 |
| WO | 2008006581 A2 | 1/2008 |
| WO | 2008128629 A1 | 10/2008 |
| WO | 2010000373 A1 | 1/2010 |
| WO | 2010118789 A1 | 10/2010 |
| WO | 2011067302 A1 | 6/2011 |

OTHER PUBLICATIONS

Szewczuk et al., "Mechanistic Analysis of a Suicide Inactivator of Histone Demethylase LSD1", 2007, Biochemistry, 46(23), pp. 6892-6902. (Year: 2007).*

Morera et al., "Targeting histone methyltransferases and demethylases in clinical trials for cancer therapy", 2016, Clinical Epigenetics, 8(1), Article: 57 (DOI: 10.1186/s13148-016-0223-4). (Year: 2016).*

Maiques-Diaz et al., "LSD1: biologic roles and therapeutic targeting", 2016, Epigenomics, 8(8), pp. 1103-1116. (Year: 2016).*

Granados-Principal, S. et al., "New advances in molecular mechanisms and the prevention of adriamycin toxicity by antioxidant nutrients", Food and Chemical Toxicology, vol. 48, pp. 1425-1438 Dec. 31, 2010.

Han, J. et al., "Anti-proliferative and apoptotic effects of oleuropein and hydroxytyrosol on human breast cancer MCF-7 cells", Cytotechnology, vol. 59, pp. 45-53 Dec. 31, 2009.

McCord, E. Darlene et al., PCT/US2013/072276, "Notification of Transmittal of the International Search Report and the Written Opinion of the International Searching Authority, or the Declaration" dated Mar. 25, 2014.

Gonzalez-Correa, Jose Antonia, et al., "Neuroprotective effect of hydroxytyrosol and hydroxytyrosol acetate in rat brain slices subjected to hypoxia-reoxygenation", Neuroscience Letters 446 (2008), 143-146. Dec. 31, 2008.

Granados-Principal, Sergio, et al., "Hydroxytyrosol: from laboratory investigations to future clinical trials", Nutrition Reviews vol. 68 (4), 2010: 191-206. Dec. 31, 2010.

McCord, Darlene, PCT/US2010/045049 filed Jan. 12, 2012, "The Extended European Search Report", dated Mar. 19, 2013. Mar. 19, 2013.

PCT Search Report for PCT/US2010/045049 dated Jan. 28, 2011.

D'Angelo, et. al, "Hydroxytyrosol, a natural antioxidant from olive oil, prevents protein damage induced by long-wave ultraviolet radiation in melanoma cells", Free Radical Biology & Medicine, 38 (2005) pp. 908-919 Jul. 2, 2004.

Bisignano, et al., "On the in-vitro Antimicrobial Activity of Oleuropein and Hydroxytyrosol", J. Pharm.Parmacol, 1990, 51: 971-974 Jan. 29, 1999.

Abu, et.al., "Key Attributes of TKDL", vol. II (11th Centrury AD), Institute of History of Medicine and Medical Research, Jamia Hamdard, New Delhi-62, 1987 AD, pp. 213-215, Last accessed on Aug. 31, 2015.

Abu, et.al, "Key Attributes of TKDL", vol. XX (9th Century AD), (First Edition) 1967 AD, p. 180, last accessed on Aug. 31, 2015.

Abu, et. al, "Key Attributes of TKDL", vol. III (9th Century AD), Second Edition, 1977 AD, p. 321, last accessed on Aug. 31, 2015.

Capasso, et.al. "Production of Glucose and Bioactive Aglycone by Chemical and Enzymatic Hydrolysis of Purified Oleuropein from Olea Europea", Humana Press, Inc., 13 pages May 18, 1995.

Coller, et. al.,"A New Description of Cellular Quiescence", Freely available online through www.plosbiology.org, 21 pages Mar. 7, 2006.

Consenza, et.al.,"Evidence That the Time of Entry into S Is Determined by Events Occurring in Early GI", The Journal of Biological Chemistry, vol. 263, No. 25, pp. 12751-12758 Sep. 5, 1988.

Deiana, et.al., "Protective effect of hydroxytyrosol and its metabolite homovanillic alcohol on H2O2 induced lipid peroxidation in renal tubular epithelial cells", Food and Chemical Toxicology 46 (2008), 7 pages Jan. 4, 2008.

Dog, Tieranona Low, MD.,"Menopause: a review of botanical dietary supplements", The American Journal of Medicine (2005), vol. 118 (12 B), 11 pages, last accessed on Aug. 31, 2015.

Fabiani, et. al., "Cancer chemoprevention by hydroxytyrosol isolated from virgin olive oil through G1 cell cycle arrest and apoptosis", European Journal of Cancer Prevention 2002, 11, pp. 351-358 Nov. 23, 2001.

Fabiani, et. al., "Inhibition of Cell Cycle Progression by Hydroxytyrosol Is Associated with Upregulation of Cyclin-Dependent Protein Kinase Inhibitors . . . ", The Journal of Nutrition, 7 pages Jul. 20, 2007.

Fernandez-Bolanos et. al., "Potential use of olive by-products", Food Biotechnology Dept, Institudo de la Grasa (CSIC), 12 pages Sep. 30, 2005.

Gray, et.al., "Sleeping Beauty: Quienscence in *Saccharomyces cerevisiae*", Microbiology and Molecular Biology Reviews, Jun. 2004, vol. 68, No. 2, p. 187-206 Jun. 30, 2012.

Guichard, et. al., "Dihydroxyphenylethanol induces apoptosis by activating serine/threonine protein . . . " Carcinogenesis vol. 27 No. 9, pp. 1812-1827 Mar. 7, 2006.

Gupta, Third Party Submission under 37 CFR 1.99 in respect of U.S. Appl. No. 12/823,567 and Patent Publication No. 20100331377, filed on Jun. 25, 2010 and published on Dec. 30, 2010, 19 pages Sep. 2, 2011.

(56) References Cited

OTHER PUBLICATIONS

Haber et.al., "N-acetylcysteine and taurine prevent hyperglycemia-induced insulin resistance in vivo: possible role of oxidative stress", American Physiological Society, 285: E744-E753, 2003 Aug. 4, 2013.
Haloui, et.al., "Hydroxytyrosol and oleuropein from olive leaves: Potent anti-inflammatory and analgesic activities" Journal of Food, Agriculture & Environment vol. 9 (3&4): 128-133.2011 Jun. 5, 2011.
Hengartner. "The biochemistry of apoptosis", Macmillan Magazines Ltd, Nature vol. 407, 7 pages Oct. 12, 2000.
Johnson, et. al., In Vitro Formation of Quinoid Metabolites of the Dietary Supplement Cimicifuga racemosa (Black Cohosh)_ Ameican Chemical Society, vol. 16 pp. 838-846 May 21, 2003.
Liu, et.al., "Hydroxytryrosol protects retinal pigment epithelial cells from acrolein-induced oxidative stress and mitochondrial dysfunction", Journal of Neurochemistry, 2007, 103, 2690-2700 Jul. 11, 2007.
Manna, et. al., "Protective Effect of the Phenolic Fraction from Virgin Olive Oils against Oxidative Stress in Human Cells", Journal of Argicultural and Food Chemistry, 2002, 50, 6521-6526 Sep. 24, 2002.
Matthews, "Protein absorption", Journal of Clinical Pathology, 24, Suppl (Roy.Coll. PAth), 5, 29-40 Nov. 8, 2012.
Mohammad, et.al., "Key Attributes of TKDL", vol. IV (19th Century AD), 1872 AD, p. 283, last accessed on Aug. 31, 2015.
Pereira, et. al., Phenolic Compounds and Antimicrobial Activity of Olive (*Olea europaea* L.Cv. Cobrancosa) Leaves, Molecules 2007, 12, 1153-1162 May 26, 2007.
Ragione, et. al., "Hydroxytyrosol, a Natural Molecule Occuring in Olive Oil, Induces Cytochrome c-Dependent Apoptosis", Biochemical and Biophysical Research Communications 278, 733-739 (2000) Oct. 17, 2000.
Romani, et.al., Polyphenolic Content in Five Tuscany Cultivars of *Olea europaea* L., Journal of Argricultrual Food Chemistry 1999, 47, 964-967 Feb. 9, 1999.
Sarsour, et. al., "Manganese Superoxide Dismutas Regulates a Metabolic Switch during the Mammalian Cell Cycle" American Association for Cancer Research, 10 pages, last accessed on Aug. 31, 2015.
Sarsour, et. al., "MnSOD activity regulates hydroxytyrosol-induced extension of chronological lifespan" Amerigan Aging Association 2011, 15 pages Apr. 8, 2013.
Scalbert, et.al., "Absorption and metabolism of polyphenols in the gut and impact on health", Bimed Pharmacother 56 (2002) 276-282 May 12, 2002.
Taavoni, el.al., "Effects of olive oil on striae gravidarum in the second trimetster of pregnancy", Science Direct Complementary Therapies in Clinical Practice, 17(2011) 167-169, last accessed on Aug. 31, 2015.
Tuck, et al., "Major phenolic compounds in olive oil: metabolism and health effects", The Journal of Nutritional Biochemistry 13 (2002) 636-644 Apr. 26, 2002.

Victor, et. al., "N-acetylcysteine Protects Mice from Lethal Endotoxemia by Regulating the Redox State of Immune Cells", Free Radical Research, vol. 37 No. 9 (Sep. 2003), pp. 919-929 Mar. 1, 2003.
Visioli, et. al., "Antioxidant and Other Biological Activities of Olive Mill Waste Waters", Journal of Agricultural Food Chemistry 1999, 47, 3397-3401 Jul. 28, 1999.
Vissers, et.al., "Olive Oil Phenols Are Absorbed in Humans", American Society for Nutritional Sciences, vol. 132: 409-417 Dec. 10, 2001.
Walter, et. al., "Preparation of Antimicrobial Compounds by Hydrolysis of Oleuropein from Green Olives", Applied Microbiology, Nov. 1973 p. 773-776, last accessed on Aug. 31, 2015.
Washington, et. al., "L-Proline induces differentiation of ES Cells: a novel role for an amino acid in the regulation of pluripotent cells in culture", American Journal of Physiological Cell Physiology 298: C982-C992, 2010 Feb. 17, 2010.
Webb, et. al., "Peptide absorption: a review of current concepts and future perspectives", Journal of Animal Sciences 1992, 70:3248-3257 Nov. 8, 2012.
Zanichelli, et.al., "Inhibition of *Staphylococcus aureus* by Oteuripein Is Mediated by Hydrogen Peroxide", Journal of Food Protection, vol. 68, No. 7, 2005, pp. 1492-1496 Nov. 15, 2004.
Zhu, et. al., "Hydroxytyrosol protects against oxidative damage by simultaneous activation of mitochondrial biogenesis and phase II detoxifying enzyme systems in retinal pigment epithelial cells", Journal of Nutritional Biochemistry, 10 pages Mar. 18, 2009.
Ziya, et. al., "Key Attributes of TKDL", vol. IV (13th Century AD), Matba Amra, Cairo, Egypt, 1874, p. 105, last accessed on Aug. 31, 2015.
International Bureau of WIPO, "International Preliminary Report on Patentability", issued in connection to International Application No. PCT/US2013/072276, 10 pages, dated Jun. 11, 2015.
Rafehi et al., "Investigation into the biological properties of the olive polyphenol, hydroxytyroso: mechanistic insights by genome-wide mRNA-Seq analysis", Apr. 2012, Genes & Nutrition, vol. 7, Issue 2, pp. 343-355. Apr. 30, 2012.
Sirianni et al., "Oleuropein and hydroxytyrosol inhibit MCF-7 breast cancer cell proliferation interfering with ERK1/2 activation", Jun. 2010, Molecular Nutrition & Food Research, vol. 54, Issue 6, pp. 833-840. Jun. 30, 2010.
PCT Search Report for PCT/US2010/040008 dated Apr. 1, 2011.
Abu, et al, "Key Attributes of TKDL", vol. XX (9th Century AD), First Addition, 1967 AD, p. 558, last accessed on Aug. 31, 2015.
Crea, Francesco, et al., "The emerging role of histone lysine demethylases in prostate cancer", Molecular Cancer, vol. 11, No. 52, (2012), 10 pages Jan. 1, 2012.
Fabiani, Roberto, et al., "Anti-proliferative and pro-apoptotic activities of hydroxytyrolsol on different tumour cells: the role of extracellular production of hydrogen peroxide", Eur J Nutr, vol. 51, (2012), pp. 455-464. Jul. 30, 2011.
Rietjens, S. et al., "The Olive oil antioxidant hydroxytyrosol protects the aorta against oxidative stress", Chemico-Biological Interactions, abstract, 1 page. Jun. 23, 2007.
European Patent Office, "Extended European Search Report", issued in connection to European Application No. 13858012.1, 11 pages, dated May 11, 2016.

\* cited by examiner

HYDROXYTYROSOL AND OLEUROPEIN COMPOSITIONS FOR INDUCTION OF DNA DAMAGE, CELL DEATH AND LSD1 INHIBITION

CROSS-REFERENCE TO RELATED APPLICATIONS

This application is a Continuation application of U.S. Ser. No. 14/823,028 filed Aug. 11, 2015, which is a continuation of U.S. Ser. No. 14/091,742 filed Nov. 27, 2013, now U.S. Pat. No. 9,144,555, issued Sep. 29, 2015, which claims priority and is related to U.S. Provisional Application Ser. No. 61/819,226 filed on May 3, 2013 and entitled Hydroxytyrosol Compositions for Induction of DNA Damage and Cell Death and Inhibition of LSD1; and to U.S. Provisional Application Ser. No. 61/731,598 filed on Nov. 30, 2012 and entitled Hydroxytyrosol Compositions for Induction of DNA Damage and Cell Death. The entire contents of this patent application are hereby expressly incorporated herein by reference including, without limitation, the specification, claims, and abstract, as well as any figures, tables, or drawings thereof.

FIELD OF THE INVENTION

The invention relates to compositions comprising hydroxytyrosol (HT) and HT-containing formulations and treatment regiments comprising hydroxytyrosol compositions and HT-containing formulations and/or oleuropein and chemotherapeutic agents. Compositions and/or regiments may optionally include the administration of vitamins, minerals, and/or anti-oxidants. Methods for using these compositions and treatment regimens for treating subjects for diseases, such as a malignancy, and for inducing or enhancing angiogenesis, treating or preventing oxidative stress, for treating or preventing high glucose-induced dysfunction, treating or preventing chemotherapy-induced dysfunction, and for improving cell viability are provided. The invention further relates to various methods for use of the hydroxytyrosol compositions and HT-containing formulations for inhibition of lysine specific demethylase 1 (LSD1) in various cancers.

BACKGROUND OF THE INVENTION

The beneficial health effects of phenolic compounds isolated from *Olea Europea* are now evident. In particular, the antioxidant and anti-inflammatory properties of hydroxytyrosol have been widely investigated and shown to have beneficial uses as an antioxidant for the treatment of oxygen free radical-associated diseases or conditions. Specifically, United States Patent Pub. No. US 2011/0034519 A1 describes compositions for and methods of administration of hydroxytyrosol, and optionally other dietary supplements, to a subject in need thereof for the inhibition and treatment of necrosis and extended quiescence that result in cellular necrosis instead of normal proliferation, which is incorporated herein by reference in its entirety. In addition, the beneficial properties of hydroxytyrosol for reversing damage to cells, promoting wound healing, and inhibiting necrosis have been similarly demonstrated. Specifically, United States Patent Pub. No. US 2013-0266545 A1 describes compositions and methods for reversing damage to skin cells and, in particular, to compositions and methods for wound healing and inhibiting necrosis, for example, in the treatment of skin that is distressed or wounded as result of a disease or other biological condition or process.

Compounds for treatment of diseases are often non-naturally occurring, cause harmful side-effects, and are expensive to produce. Chemotherapeutic agents for the treatment of cancer can be prohibitively expensive, and cause a variety of serious side effects. It is therefore unexpected and desirable that the co-therapy and/or co-administration of regimens comprising hydroxytyrosol and chemotherapeutic agents demonstrate beneficial results in treating malignancy.

Furthermore, oxidants and free radical species, such as reactive oxygen species (ROS), are known to contribute to cell damage and/or cell death, as well as having a role in various metabolic and immune system processes. Synthetic antioxidants such as butylated hydroxyanisole (BHA), and butylated hydroxytoluene (BHT) and tertiary butylhydroquinone (TBHQ) have demonstrated carcinogenicity and other toxic properties, underscoring the need for natural antioxidants. Growing evidence links antioxidants with a decreased risk of chronic diseases such as coronary heart disease, cancer, and several other aging-related health concerns (Tahseen Iqbal et al., Antioxidant Activity and Volatile and Phenolic Profiles of Essential Oil and Different Extracts of Wild Mint (*Mentha longifolia*) from the Pakistani Flora, Journal of Analytical Methods in Chemistry, (2013) vol. 2013, Article ID 536490). Oxidative stress has been linked to collateral damage in cancer chemotherapy. (See, e.g., Yumin Chen et al., Collateral Damage in Cancer Chemotherapy: Oxidative Stress in Nontargeted Tissues (2007) Mol. Interventions 7(3); 147-156). Antioxidant activity has also been linked to wound healing. (See, e.g., Arti Shukla et al. Asiaticoside-induced Elevation of Antioxidant Levels in Healing Wounds (1999) Phytother. Res. 13, 50-54); to induction of angiogenesis (see Elena Daghini et al., Antioxidant vitamins induce angiogenesis in the normal pig kidney (2007) American Journal of Physiology—Renal Physiology. 293; F371-F381); and high-glucose induced dysfunction (see G. Cohen et al., The roles of hyperglycaemia and oxidative stress in the rise and collapse of the natural protective mechanism against vascular endothelial cell dysfunction in diabetes (2007), 113(4-5); 259-267). Reduction in the concentration of one or more radical species in a biological environment thus has benefits in various biological environments for amelioration of a host of conditions. As a result compounds capable of enhancing the antioxidant capability in cells, animals, or individuals are important tools in treating or preventing a wide range of conditions. The expression of lysine specific demethylase 1 (LSD1) in various cancers is prevalent and represents a potential mechanism for prevention, treatment and/or detection of cancers. Conventional efforts to develop specific inhibitors of the LDS1 protein expressed in a majority of cancers have had limited success to date. In particular, development of specific inhibitors of the LDS1 protein active and binding sites has not resulted in significant advances in cancer treatment and/or prevention. However, the inhibition of LSD1 activity by hydroxytyrosol, hydroxytyrosol derivatives, substituted hydroxytyrosol compounds and/or hydroxytyrosol prodrugs has provided surprising and unexpected results, demonstrating at least equivalent LSD1 inhibition (or superior inhibition) to known LSDI inhibitors.

Accordingly, it is an objective of the claimed invention to provide compositions and methods for the treatment of diseases currently treated with chemotherapeutic agents, including cancers, malignancies, and tumors.

A further object of the invention is to provide compositions and methods for inhibiting LSD1 activity, particularly in cancer cells, malignancies, and tumors.

A further object of the invention is to provide methods and compositions to increase the antioxidant capacity of normal cells.

Other objects, advantages and features of the present invention will become apparent from the following specification taken in conjunction with the accompanying drawings.

BRIEF SUMMARY OF THE INVENTION

In an aspect of the invention the cytotoxic and apoptotic effects of hydroxytyrosol (HT) and HT-containing formulations in cancer cells compared normal PBMC cells has been demonstrated. "Hydroxytyrosol-containing formulations" or "HT-containing formulations" as used herein encompasses any formulation or composition that includes hydroxytyrosol, including but not limited to hydroxytyrosol alone, hydroxytyrosol in combination with oleuropein, and Formulations 1, 2, and 3 (Table 9), undiluted or at any dilution where an effective amount of hydroxytyrosol is present. The results further demonstrate applications of use treatment, suppression and/or amelioration of various conditions and diseases, including any of those currently treated with chemotoxic compounds, such as for example cancers. In an additional aspect, the ability of hydroxytyrosol to induce double-stranded breaks in DNA in malignant cells, but not normal cells, is demonstrated. The results confirm the specificity of potential treatments using hydroxytyrosol, in particular the specificity of treatment regimens using hydroxytyrosol in combination with chemotherapeutic agents. Genome-wide mRNA-sequencing has been employed to demonstrate molecular mechanisms accounting for the biological effects of hydroxytyrosol disclosed herein according to the invention. In an additional aspect of the invention, the combinatorial effects of hydroxytyrosol and the widely used chemotherapeutic, doxorubicin, in K562 cells, has been demonstrated.

In yet another aspect of the invention, the targeting of lysine specific demethylase 1 (LSD1) for the treatment of cancer cells is provided. In a preferred embodiment, LSD1 is targeted by contacting particular residues in the LSD1 protein—in particular, the tryptophan residue at position 807 (Trp807), the phenylalanine at position 560 (Phe560), and/or the histidine at position 812 (His812). In a more preferred embodiment, LSD1 activity is inhibited by treatment with hydroxytyrosol or a composition comprising hydroxytyrosol (including, as referred to herein this application without limitation, hydroxytyrosol derivatives, substituted hydroxytyrosol compounds and/or hydroxytyrosol prodrugs). In another embodiment, LSD1 expression in cancer cells is downregulated by treatment with hydroxytyrosol or a composition comprising hydroxytyrosol. In another embodiment, hydroxytyrosol is provided to a person in order to prevent or treat the growth, development, or metastasis of cancer cells.

An aspect of the invention encompasses a pharmaceutical composition for treatment, suppression and/or amelioration of a condition or disease currently treated with chemotoxic compounds, wherein said composition comprises hydroxytyrosol, a hydroxytyrosol derived and/or substituted compound, and/or a hydroxytyrosol metabolite.

Another aspect of the invention encompasses a method of treating a condition of disease currently treated with chemotoxic compounds, comprising administering to an individual in need thereof a composition comprising hydroxytyrosol, a hydroxytyrosol derived and/or substituted compound, and/or a hydroxytyrosol metabolite.

Another aspect of the invention encompasses a method for detecting cancer or pre-cancer cells in an individual comprising administering to an individual in need thereof a composition comprising hydroxytyrosol, a hydroxytyrosol derived and/or substituted compound, and/or a hydroxytyrosol metabolite to a particular site of said individual followed by detection of genetic and epigenetic effects to detect cancerous or pre-cancerous cells.

Another aspect of the invention encompasses a hydroxytyrosol-based inhibitor of the LDS1 protein comprising: hydroxytyrosol, a hydroxytyrosol derived and/or substituted compound, and/or a hydroxytyrosol metabolite.

Another aspect of the invention encompasses a pharmaceutical composition for treating cancers comprising the hydroxytyrosol-based inhibitor of the LDS1 protein comprising hydroxytyrosol, a hydroxytyrosol derived and/or substituted compound, and/or a hydroxytyrosol metabolite, a chemotherapeutic agent and a pharmaceutically acceptable carrier.

Another aspect of the invention encompasses a method of inhibiting LSD1 in a cell comprising contacting said cell with a composition comprising hydroxytyrosol, a hydroxytyrosol derived and/or substituted compound, and/or a hydroxytyrosol metabolite.

Another aspect of the invention encompasses a method of inhibiting LSD1 in a cell comprising contacting said cell with a composition comprising a compound that interacts with LSD1 at either the flavin group of LSD1 or close to the adenosine group of LSD1.

Another aspect of the invention encompasses a method of detecting an LSD1-expressing cancer in an individual comprising contacting a sample from said individual with or administering to said individual directly a composition comprising hydroxytyrosol, a hydroxytyrosol derived and/or substituted compound, and/or a hydroxytyrosol metabolite, followed by detection of LSD1 inhibition.

Another aspect of the invention encompasses a method for increasing lysine methylation of a histone polypeptide in a cell comprising contacting said cell with a composition comprising hydroxytyrosol, a hydroxytyrosol derived and/or substituted compound, and/or a hydroxytyrosol metabolite.

Another aspect of the invention encompasses a method for increasing or decreasing gene expression in a cell comprising contacting said cell with a composition comprising hydroxytyrosol, a hydroxytyrosol derived and/or substituted compound, and/or a hydroxytyrosol metabolite.

Another aspect of the invention encompasses a method for inducing cell death in a comprising contacting said cell with a composition comprising hydroxytyrosol, a hydroxytyrosol derived and/or substituted compound, and/or a hydroxytyrosol metabolite.

Another aspect of the invention encompasses a method for improving cell viability comprising contacting said cell with a composition comprising hydroxytyrosol, a hydroxytyrosol derived and/or substituted compound, and/or a hydroxytyrosol metabolite.

Another aspect of the invention encompasses a method for treating or preventing chemotherapy-induced dysfunction in an individual or cell comprising contacting said individual or cell with a composition comprising hydroxytyrosol, a hydroxytyrosol derived and/or substituted compound, and/or a hydroxytyrosol metabolite.

Another aspect of the invention encompasses a method for treating or preventing high glucose-induced dysfunction in an individual or cell comprising contacting said individual or cell with a composition comprising hydroxytyrosol, a hydroxytyrosol derived and/or substituted compound, and/or a hydroxytyrosol metabolite.

Another aspect of the invention encompasses a method for treating or preventing oxidative stress in an individual or cell comprising contacting said individual or cell with a composition comprising hydroxytyrosol, a hydroxytyrosol derived and/or substituted compound, and/or a hydroxytyrosol metabolite.

Another aspect of the invention encompasses a method for inducing or enhancing angiogenesis comprising administering a composition comprising hydroxytyrosol, a hydroxytyrosol derived and/or substituted compound, and/or a hydroxytyrosol metabolite.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1A:
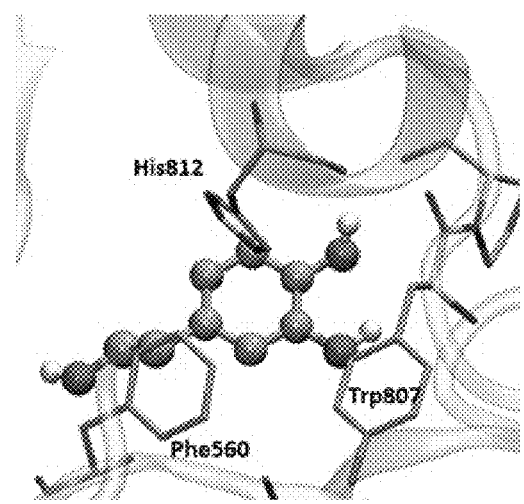
FIG. 1 (A-B) shows the top predicted binding site for HT (CPK spheres) on lysine demethylase 1 (LSD1). LSD1 residues forming close contacts with the ligand are illustrated in thin licorice representation. (A) This model suggests the possibility of $\pi$-$\pi$ interactions between Trp807, Phe560 and HT, as well as cation-$\pi$ interactions between His812 and HT, which may serve to stabilize the binding. (B) Another predicted binding pose for HT superimposed on the tranylcypromine adduct and flavin group (transparent licorice). Docking positions near the adduct in 2EJR may serve as guides to propose FAD-HT covalently bound chemical structures responsible for inhibition.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE PREFERRED EMBODIMENT

The embodiments of this invention are not limited to particular compositions and methods of use thereof, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form. Numeric ranges recited within the specification are inclusive of the numbers defining the range and include each integer within the defined range.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

In the present invention, an "effective amount" or "therapeutically effective amount" of a compound or of a composition of the present invention is that amount of such compound and/or composition that is sufficient to affect beneficial or desired results as described herein. In terms of treatment of a mammal, e.g., a human patient, an "effective amount" is an amount sufficient to at least slow the progression or spread of disease, or render the disease susceptible to therapeutics or remediation.

The term "cancers," as used herein, refers to the commonly understood spectrum of diseases including, but not limited to, solid tumors, such as cancers of the breast, respiratory tract, brain, reproductive organs, digestive tract, urinary tract, eye, liver, skin, head and neck, thyroid, parathyroid and their distant metastases, and also includes lymphomas, sarcomas, and leukemias. Examples of breast cancer include, but are not limited to invasive ductal carcinoma, invasive lobular carcinoma, ductal carcinoma in situ, and lobular carcinoma in situ. Examples of cancers of the respiratory tract include, but are not limited to small-cell and non-small-cell lung carcinoma, as well as bronchial adenoma and pleuropulmonary blastoma. Examples of brain cancers include, but are not limited to brain stem and hypophthalmic glioma, cerebellar and cerebral astrocytoma, medulloblastoma, ependymoma, as well as neuroectodermal and pineal tumor. Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus. Tumors of the digestive tract include, but are not limited to anal, colon, colorectal, esophageal, gallbladder, gastric, pancreatic, rectal, small intestine, and salivary gland cancers. Tumors of the urinary tract include, but are not limited to bladder, penile, kidney, renal pelvis, ureter, and urethral cancers. Eye cancers include, but are not limited to intraocular melanoma and retinoblastoma. Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma. Skin cancers include, but are not limited to squamous cell carcinoma, Kaposi's sarcoma, malignant melanoma, Merkel cell skin cancer, and non-melanoma skin cancer. Head-and-neck cancers include, but are not limited to laryngeal/hypopharyngeal/nasopharyngeal/oropharyngeal cancer, and lip and oral cavity cancer. Lymphomas include, but are not limited to AIDS-related lymphoma, non-Hodgkin's lymphoma, cutaneous T-cell lymphoma, Hodgkin's disease, and lymphoma of the central nervous system. Sarcomas include, but are not limited to sarcoma of the soft tissue, fibrosarcoma, osteosarcoma, malignant fibrous histiocytoma, lymphosarcoma, and rhabdomyosarcoma. Leukemias include, but are not limited to acute myeloid leukemia, acute lymphoblastic leukemia, chronic lymphocytic leukemia, chronic myelogenous leukemia, and hairy cell leukemia. Cancers also specifically include, but are not limited to, chronic myeloid leukemia (CML), acute myeloid leukemia (AML), cutaneous T cell lymphoma (CTCL), cutaneous T cell lymphoma (CTCL), acute T lymphoblast leukemia (ALL), MDR acute T lymphoblast leukemia (MDR ALL), large B-lymphocyte non-Hodgkin's lymphoma, leukemic monocyte lymphoma, epidermal squamous carcinoma, epithelial lung adenocarcinoma, liver hepatocellular carcinoma, colorectal carcinoma, breast adenocarcinoma, brain glioblastoma, prostate adenocarcinoma, gastric carcinoma and other cancerous tissues. Cancers further include all forms of cancer expressing lysine specific demethylase 1 (LSD1). These disorders have been characterized in humans, but also exist with a similar etiology in other mammals, and can be treated by administering the methods and compositions of the present invention.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

As one skilled in the art shall appreciate, there are two distinct mechanisms for cell death. "Apoptosis" refers to "normal" or programmed cell death, which encompasses the physiological process by which cells are routinely eliminated, giving balance to the proliferation of new cells. During apoptosis the outer membrane of the cell forms "bubbles" known as blebs. The content of the cells becomes incased in the blebs. The blebs separate from the cell and are digested by nearby cells or macrophages. This orderly process greatly reduces toxicity to surrounding cells.

"Necrosis" refers to a distinct form of cell death that is not a programmed event and is known as "accidental" death. This pathological process occurs when cells are exposed to extreme stress, chemical insult, and resultant free radical damage. The early stages of necrosis involve a swelling of the cell called oncosis. During oncosis the cell and its organelles begin to swell due to an exchange in the cell's potassium to sodium ratios. Necrosis, after the oncosis stage, is an explosive event where the cells contents stream directly into the surrounding cells environment causing damage and an immune response. Controlling necrosis during the early oncosis stage is important. Up to this point, necrosis is a reversible event. The morphology of cells dying by necrosis centers on changes in the cell's permeability. Hengartner M O, The biochemistry of apoptosis. Nature 407: 770-776, 2000, which is herein incorporated by reference in its entirety. Osmotic changes take place during an exchange of cytosol potassium and extracellular sodium. Early stage necrosis, known as oncosis, is characterized by the dilation or swelling of the cell and its organelles due to this exchange. Cell survival of this non-programmed event is dependent upon repairing the cell's membrane and stopping the flow of sodium ions into the cells interior. Repair of the cell's membrane and improvement in the cell's environment to more homeostatic conditions are paramount to survival "Quiescence" refers to the normal part of the cell cycle, also referred to as "$G_0$," that is the counterpart to proliferation, and involves a myriad of molecular events that occur and trigger the progression to the pre-replicative ($G_1$) phase. Cosenza S C, Owen T A, Soprano D R, Soprano K J, Evidence That the Time of Entry into S is Determined by Events Occurring in Early $G_1$. J Biological Chem 263; 12751-12758; 1988. The $G_0$ phase represents not just the absence of signals for mitosis but an active repression of the genes needed for mitosis. This is an important distinction since cancer cells cannot enter $G_0$ and as a consequence become immortal.

The methods and compositions of the present invention may comprise, consist essentially of, or consist of the components and ingredients of the present invention as well as other ingredients described herein. As used herein, "consisting essentially of" means that the methods and compositions may include additional steps, components or ingredients, but only if the additional steps, components or ingredients do not materially alter the basic and novel characteristics of the claimed methods and compositions.

Compositions

In an aspect of the invention the administration of hydroxytyrosol-containing formulations results in selective cell damage, including for example cell death, apoptosis and/or DNA double-strand breaks in cells in need of treatment according to the invention. The term apoptosis often is used interchangeably with programmed cell death. According to the invention, the selective effects on cells results in no damage to normal cells. In an aspect, the hydroxytyrosol-containing formulations are employed as a pre-treatment for the chemotherapeutic agents. The compositions according to the invention provide a biochemical mechanism by which cellular characteristics are regulated. The compositions and/or treatment regimens according to the invention comprise hydroxytyrosol-containing formulations, and may also include a chemotherapeutic agent.

Hydroxytyrosol-containing formulations as used herein encompasses any formulation or composition that includes hydroxytyrosol, including but not limited to hydroxytyrosol alone, hydroxytyrosol in combination with oleuropein, and Formulations 1, 2, and 3 (Table 9), undiluted or at any dilution where an effective amount of hydroxytyrosol is present. Additional components may be added to hydroxytyrosol-containing formulations, such as a chemotherapeutic agent, carrier, diluent and/or other pharmaceutically acceptable delivery agents or the like.

In one aspect, hydroxytyrosol compositions include any hydroxytyrosol-based inhibitor of the LDS1 protein. Suitable hydroxytyrosol-based inhibitor of the LDS1 protein include, for example, hydroxytyrosol, a hydroxytyrosol derived compound, a hydroxytyrosol substituted compound, a hydroxytyrosol metabolite (originating from a prodrug), and combinations of the same.

Hydroxytyrosol

The compositions according to the invention employ hydroxytyrosol. Hydroxytyrosol (HT; CAS Registry number [10597-60-1]), is also known as 3-hydroxytyrosol, 3,4-dihydroxyphenyl ethanol (DOPET) or 4-(2-hydroxyethyl)-1,2-benzenediol. Hydroxytyrosol has the Formula I set out below:

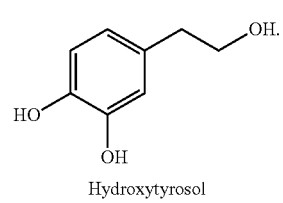

Hydroxytyrosol

For use in the hydroxytyrosol-containing formulations and other compositions of the present invention, hydroxytyrosol may be derived from natural sources or prepared by chemical synthesis. For example, the hydroxytyrosol may be obtained as an extract of, or otherwise derived from, olive leaves, olive fruits and vegetation water of olive oil production. When obtained as an extract, for example, of olive leaves, the extract will contain hydroxytyrosol, tyrosol, oleuropein, and other polyphenols. In one preferred embodiment, the hydroxytyrosol is obtained as an olive leaf extract of *Olea europaea*. Further description regarding the isolation and purification of hydroxytyrosol from olive by-products is described by Fernandez-Bolanos et al., Cur. Org. Chem. 12: 442-463 (2008), which is hereby incorporated by reference in its entirety.

Exemplary synthesis procedures for the chemical and/or enzymatic synthesis of hydroxytyrosol are suitable for use according the present invention. Exemplary synthesis procedures may include, for example, synthesis from tyrosol, synthesis from 3,4-dihydroxyphenylacetic acid (and its methyl ester), and/or synthesis from oleuropein. Such synthesis procedures are suitable for synthesis of hydroxytyrosol, substituted hydroxytyrosol and/or hydroxytyrosol derivatives according to the invention. In further embodiments, hydroxytyrosol derivatives such as hydroxytyrosol acyl derivatives can be synthesized by chemical and/or chemoenzymatic methods. Further description regarding exemplary synthesis of hydroxytyrosol is described by Fernandez-Bolanos et al., Cur. Org. Chem. 12: 442-463 (2008), which is hereby incorporated by reference in its entirety.

In addition to isolated, purified, derived and/or synthesized hydroxytyrosol compositions, according to a further embodiment, a hydroxytyrosol derivative and/or substituted hydroxytyrosol, include for example hydroxytyrosol acyl derivatives according to the following Formula II:

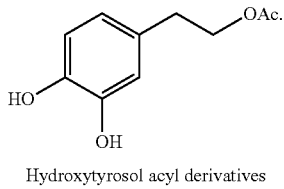

Formula II
Hydroxytyrosol acyl derivatives

Further reaction and/or substitution of the acyl derivative can include use of various acylating agents, including for example, palmitic acid, ethyl butyrate, ethyl stearate, ethyl oleato, ethyl eicosapentaenoate, ethyl docosahexaenoate to produce various fatty acid esters of hydroxytyrosol. Exemplary acyl derivatives include those shown in Table 3 of Fernandez-Bolanos et al., Cur. Org. Chem. 12: 442-463 (2008), which is reproduced below.

| Acylating Agents | Product |
|---|---|
| Palmitic acid[a] | ![structure 46] 46 |
| Ethyl butyrate[b] | ![structure 47] 47 |
| Ethyl stearate[b] | ![structure 48] 48 |
| Ethyl oleato[b] | ![structure 41] 41 |
| Ethyl eicosapentaenoate[b] | ![structure 49] 49 |
| Ethyl docosahexaenoate[b] | ![structure 50] 50 |

In a further embodiment, compounds derived from hydroxytyrosol (hydroxytyrosol derivatives), hydroxytyrosol substituted compound, metabolites of hydroxytyrosol (its derivatives and/or substituted compounds), one or more mixtures thereof, or one or more combinations thereof are employed for hydroxytyrosol compositions.

In a further embodiment, hydroxytyrosol derivative and/or substituted hydroxytyrosol, include for example hydroxytyrosol acyl derivatives, substitute'd hydroxyl groups and/or substituted compositions are employed and have the following general Formula III:

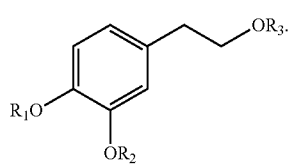

Formula III

Hydroxytyrosol derivative and/or substituted hydroxytyrosol wherein R1, R2, and R3 provide a pharmaceutically acceptable salt, solvate, prodrug and/or isomer of hydroxytyrosol that has inhibitory efficacy against the LSD1 protein; interacts with Trp807, Phe560, and/or His812 of LSD1; improves cell viability in normal, non-cancer cells; abrogates or prevents chemotherapy-induced dysfunction; abrogates or prevents high glucose-induced dysfunction; increases antioxidant activity; and/or induces or enhances angiogenesis.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein. For example, all of the compounds represented by Formula III are hydroxytyrosol derivative and/or substituted hydroxytyrosol derivatives, and have Formula III as a common core.

The term "prodrug" as understood by one skilled in the art refers to compounds or derivatives that are converted in vivo to the compounds of the invention as a result of spontaneous chemical reaction(s), enzyme catalyzed chemical reaction(s), and/or metabolic chemical reaction(s). Examples of prodrugs include, but are not limited to, derivatives and metabolites of the compounds of the formula set forth according to the present invention. These may include, for example, biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Further, prodrugs include compounds that can be oxidized, reduced, aminated, deaminated, esterified, deesterified, alkylated, dealkylated, acylated, deacylated, phosphorylated, dephosphorylated, or other functional group change or conversion involving forming or breaking chemical bonds on the prodrug, by either enzymatic action or by general acid or base solvolysis. Prodrugs can be prepared according to methods known to one skilled in the art, such as those described by Burger "Medicinal Chemistry and Drug Discovery 6th ed. (Donald J. Abraham ed., 2001, Wiley) and "Design and Applications of Prodrugs" (H. Bundgaard ed., 1985, Harwood Academic Publishers). Further, structurally-diverse prodrugs of hydroxytyrosol have been described by Fernandez-Bolanos, J G, Lopez O, Fernandez-Bolanos J, Rodriguez Gutierrez G. "Hydroxytyrosol and derivatives: isolation, synthesis, and biological properties." Cur. Org. Chem. 12: 442-463 (2008), which is hereby incorporated by reference in its entirety. Without limiting the scope of the invention, any compound that is a prodrug of a compound of the formulas according to the invention are included within the scope of the invention.

In a still further embodiment, hydroxytyrosol derivative and/or substituted hydroxytyrosol, include for example hydroxytyrosol acyl derivatives, substituted hydroxyl groups and/or substituted compositions are employed and have the following general structure:

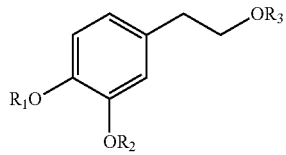

wherein R1, R2 and R3 are independently selected from the group consisting of hydrogen, substituted or unsubstituted alkyl, substituted or unsubstituted alkenyl, substituted or unsubstituted alkynyl, substituted or unsubstituted aryl, substituted or unsubstituted heterocyclyl, substituted or unsubstituted acyl, ORa, SRa, SORa, SO2Ra, OSO2Ra, OSO3Ra, NO2, NHRa, N(Ra)2, =N—Ra, N(Ra)CORa, N(CORa)2, N(Ra)SO2R', N(Ra)C(=NRa)N(Ra)Ra, CN, halogen, CORa, COORa, OCORa, OCOORa, OCONHRa, OCON(Ra)2, CONHRa, CON(Ra)2, CON(Ra)ORa, CON(Ra)SO2Ra, PO(ORa)2, PO(ORa)Ra, PO(ORa)(N(Ra)Ra) and aminoacid ester having inhibitory efficacy against the LSD1 protein; and further wherein each of the Ra groups is independently selected from the group consisting of hydrogen, substituted or unsubstituted alkyl, substituted or unsubstituted alkenyl, substituted or unsubstituted alkynyl, substituted or unsubstituted aryl, and substituted or unsubstituted heterocyclyl, substituted or unsubstituted acyl, and the like having inhibitory efficacy against the LSD1 protein; and further wherein each of the substituted or unsubstituted alkyl, alkenyl, alkynyl, aryl, heterocyclyl, and/or acyl groups are C1-28 (including all ranges therein).

"Alkyl" refers to a straight or branched hydrocarbon chain radical consisting of carbon and hydrogen atoms, containing no unsaturation, and which is attached to the rest of the molecule by a single bond. Alkyl groups may include straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups). Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

Alkyl groups preferably have from 1 to about 22 carbon atoms. Methyl, ethyl, n-propyl, iso-propyl and butyl, including n-butyl, tert-butyl, sec-butyl and iso-butyl are particularly preferred alkyl groups. As used herein, the term alkyl, unless otherwise stated, refers to both cyclic and noncyclic groups, although cyclic groups will comprise at least three carbon ring members, such as cyclopropyl or cyclohexyl. Alkyl radicals may be optionally substituted by one or more substituents, such as an aryl group, like in benzyl or phenethyl.

"Alkenyl" and "Alkynyl" refer to a straight or branched hydrocarbon chain radical consisting of carbon and hydrogen atoms, containing at least one unsaturation (one carbon-carbon double or triple bond respectively) and which is attached to the rest of the molecule by a single bond. Alkenyl and alkynyl groups preferably have from 2 to about 22 carbon atoms. The terms alkenyl and alkynyl as used herein refer to both cyclic and noncyclic groups, although cyclic groups will comprise at least three carbon ring members. Alkenyl and alkenyl radicals may be optionally substituted by one or more substituents.

"Aryl" refers to a radical derived from an aromatic hydrocarbon by removal of a hydrogen atom from a ring carbon atom. Suitable aryl groups in the present invention include single and multiple ring compounds, including multiple ring compounds that contain separate and/or fused aryl groups. Typical aryl groups contain from 1 to 3 separated and/or fused rings and from 6 to about 22 carbon ring atoms. Aryl radicals may be optionally substituted by one or more substituents. Specially preferred aryl groups include substituted or unsubstituted phenyl, substituted or unsubstituted naphthyl, substituted or unsubstituted biphenyl, substituted or unsubstituted phenanthryl and substituted or unsubstituted anthryl.

"Heterocyclyl" refers to a cyclic radical having as ring members atoms of at least two different elements. Suitable heterocyclyl radicals include heteroaromatic and heteroalicyclic groups containing from 1 to 3 separated and/or fused rings and from 5 to about 18 ring atoms. Preferably heteroaromatic and heteroalicyclic groups contain from 5 to about 10 ring atoms. Heterocycles are described in: Katritzky, Alan R., Rees, C. W., and Scriven, E. Comprehensive Heterocyclic Chemistry (1996) Pergamon Press; Paquette, Leo A.; Principles of Modern Heterocyclic Chemistry W.A. Benjamin, New York, (1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28. Suitable heteroaromatic groups in the compounds of the present invention contain one, two or three heteroatoms selected from N, O or S atoms and include, e.g., coumarinyl including 8-coumarinyl, quinolyl including 8-quinolyl, isoquinolyl, pyridyl, pyrazinyl, pyrazolyl, pyrimidinyl, furyl, pyrrolyl, thienyl, thiazolyl, isothiazolyl, triazolyl, tetrazolyl, isoxazolyl, oxazolyl, imidazolyl, indolyl, isoindolyl, indazolyl, indolizinyl, phthalazinyl, pteridinyl, purinyl, oxadiazolyl, thiadiazolyl, furazanyl, pyridazinyl, triazinyl, cinnolinyl, benzimidazolyl, benzofuranyl, benzofurazanyl, benzothienyl, benzothiazolyl, benzoxazolyl, quinazolinyl, quinoxalinyl, naphthyridinyl, and furopyridinyl. Suitable heteroalicyclic groups in the compounds of the present invention contain one, two or three heteroatoms selected from N, O or S atoms and include, e.g., pyrrolidinyl, tetrahydrofuryl, dihydrofuryl, tetrahydrothienyl, tetrahydrothiopyranyl, piperidyl, morpholinyl, thiomorpholinyl, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, pyrazolidinyl, imidazolinyl, imidazolidinyl, 3-azabicyclo[3.1.0]hexyl, 3-azabicyclo[4.1.0]heptyl, 3H-indolyl, and quinolizinyl. Heterocylic radicals may be optionally substituted by one or more substituents.

In each of the aforementioned embodiments, the components of the composition of the present invention may optionally be present in the form of an ester or a physiologically and/or pharmaceutically acceptable salt. Exemplary esters include the mono-, di- and triesters of hydroxytyrosol with (un)saturated carbonic acids R—COON, whereby R is an alkyl or alkenyl chain having 2 to 22 carbon atoms. Exemplary pharmaceutically acceptable salts refers to salts prepared from pharmaceutically acceptable non-toxic acids, including inorganic salts and organic salts. Suitable nonorganic salts include inorganic and organic acids such as acetic, benzenesulfonic, benzoic, camphorsulfonic, citric, ethenesulfonic, fumaric, gluconic, glutamic, hydrobromic, hydrochloric, isethionic, lactic, malic, maleic, mandelic, methanesulfonic, mucic, nitric, pamoic, pantothenic, phosphoric, succinic, sulfuric, tartaric acid, p-toluenesulfonic and other pharmaceutically acceptable salts as provided in Stahl and Wermuth "Pharmaceutical Salts Properties, Selection, and Use", 1st Ed, Wiley-VCH, 374 (2002). Thus, for example, the hydroxytyrosol may be provided as hydroxytyrosol acetate which releases hydroxytyrosol in the stomach or intestine.

In an aspect, the compositions according to the invention deliver at least about 1 µM hydroxytyrosol, at least about 5 µM hydroxytyrosol, at least about 10 µM hydroxytyrosol, at least about 20 µM hydroxytyrosol, at least about 50 µM hydroxytyrosol, at least about 100 µM hydroxytyrosol, or greater. In addition, without being limited according to the invention, all ranges recited are inclusive of the numbers defining the range and include each integer within the defined range. In general, larger doses tend to produce greater effects, with the preferred dosage also depending, at least in part, upon weight, metabolism, individual body chemistry, type of cancer or other condition being treated, and the like.

In an embodiment the dose of hydroxytyrosol administered to a person is about 0.01 to about 1000 micrograms per kilogram of body weight. In addition, without being limited according to the invention, all ranges recited are inclusive of the numbers defining the range and include each integer within the defined range. In a further aspect, the hydroxytyrosol is present at a level such that an effective amount for the induction of cell death, apoptosis and/or DNA double-strand breakage in malignant cells results.

Depending upon the route of administration, greater doses of hydroxytyrosol may be administered. For example, significantly lesser amounts of hydroxytyrosol may be absorbed when the route of administration is oral as compared to parenteral or other forms of systemic administration. For oral delivery, therefore, the daily dose of hydroxytyrosol administered orally may be about 0.01 micrograms to about 1000 micrograms per kilogram of body weight. By way of further example, in one embodiment, the daily dose of hydroxytyrosol administered orally to a person is about 1 to about 100 micrograms per kilogram of body weight. By way of further example, in one embodiment, the daily dose of hydroxytyrosol administered orally to a person is about 5 to about 50 micrograms per kilogram of body weight. By way of further example, in one embodiment, the daily dose of hydroxytyrosol administered orally to a person is about 10 micrograms to about 50 micrograms per kilogram of body weight.

For parenteral delivery the daily dose may be from about 0.01 to about 100 micrograms per kilogram of body weight per day, twice a day, or more than twice a day. In one embodiment, the daily dose of hydroxytyrosol parenterally administered to a person is about 0.1 to about 50 micrograms per kilogram of body weight per day. In another such embodiment, the daily dose of hydroxytyrosol parenterally administered to a person is about 0.1 to about 10 microgram per kilogram of body weight.

Regardless of the route of administration of the hydroxytyrosol, the compositions may be administered in a single dose or multiple doses to achieve a target daily dose. For example, for certain embodiments the hydroxytyrosol is provided in a formulation that will provide a single daily dose. Alternatively, for such embodiments the hydroxytyrosol is provided in a formulation that will provide, in two or more doses over the course of a day.

As one skilled in the art appreciates, greater amounts of hydroxytyrosol may be included in the dosage unit form when the intended route of administration is oral. For example, typical dosage forms for oral administration include tablets, pills, capsules, gelcaps, caplets, and the like. A single dose, therefore, may comprise a single tablet, pill, capsule, gelcap, caplet or the like, or two or more tablets, pills, capsules, gelcaps, caplets, and the like. In general, dosage forms for oral administration may contain 0.01 to 100 milligrams of hydroxytyrosol. For example, in one embodiment, the dosage unit form contains 1 to 50 milligrams hydroxytyrosol.

The route of administration may affect the rate and extent of absorption of hydroxytyrosol. Taking this into account, i.e., taking into account the fraction of an administered dose that is not absorbed or for whatever reason is not systemically bioavailable to the subject, it is generally preferred that the administered dose provide the subject with at least about 100 but less than about 10,000, preferably less than about 6,000 TE of systemically bioavailable hydroxytyrosol per day. In general, it is preferred that the administered dose provide the subject with at least about 250 TE of systemically bioavailable hydroxytyrosol per day. In certain embodiments, it is preferred that the administered dose provide the subject with at least about 500, at least about 750, at least about 1,000, or at least about 5,000 TE of systemically bioavailable hydroxytyrosol per day.

Chemotherapeutic Agents

The compositions according to the invention employ a chemotherapeutic agent. Chemotherapeutics may also be referred to as chemotoxic agents, chemotherapy and the like which are customarily employed to diminish cell proliferation and/or to induce cell apoptosis as one skilled in the art appreciates. Additional cancer therapies may also be employed in combination with the hydroxytyrosol according to the invention, including for example biotherapeutic agents, radiopharmaceuticals, and the like.

As one skilled in the art appreciates, cancer chemotherapeutic agents are used for their lethal action to cancer cells. Unfortunately, few such drugs differentiate between a cancer cell and other proliferating cells. Chemotherapy generally requires use of several agents concurrently or in planned sequence. Combining more than one agent in a chemotherapeutic treatment protocol allows for: (1) the largest possible dose of drugs; (2) drugs that work by different mechanisms; (3) drugs having different toxicities; and (4) the reduced development of resistance. Chemotherapeutic agents mainly affect cells that are undergoing division or DNA synthesis; thus slow growing malignant cells, such as lung cancer or colorectal cancer, are often unresponsive. Furthermore, most chemotherapeutic agents have a narrow therapeutic index. Common adverse effects of chemotherapy include vomiting, stomatitis, and alopecia. Toxicity of the chemotherapeutic agents is often the result of their effect on rapidly proliferating cells, which are vulnerable to the toxic effects of the agents, such as bone marrow or from cells harbored from detection (immunosuppression), gastrointestinal tract (mucosal ulceration), skin and hair (dermatitis and alopecia).

Many potent cytotoxic agents act at specific phases of the cell cycle (cell cycle dependent) and have activity only against cells in the process of division, thus acting specifically on processes such as DNA synthesis, transcription, or mitotic spindle function. Other agents are cell cycle independent. Susceptibility to cytotoxic treatment, therefore, may vary at different stages of the cell life cycle, with only those cells in a specific phase of the cell cycle being killed. Because of this cell cycle specificity, treatment with cytotoxic agents needs to be prolonged or repeated in order to allow cells to enter the sensitive phase. Non-cell-cycle-specific agents may act at any stage of the cell cycle; however, the cytotoxic effects are still dependent on cell proliferation. Cytotoxic agents thus kill a fixed fraction of tumor cells, the fraction being proportionate to the dose of the drug treatment.

Exemplary chemotherapeutic agents suitable for use in compositions and/or combinational therapies according to the invention include: anthracyclines, such as doxorubicin, alkylating agents, nitrosoureas, antimetabolites, such as 5-FU, platins, antitumor antibiotics, such as dactinomycin, daunorubicin, doxorubicin (Adriamycin), idarubicin, and mitoxantrone, miotic inhibitors, alkylating agents, mitotic inhibitors, steroids and natural hormones, including for example, corticosteroid hormones, sex hormones, immunotherapy or others such as L-asparaginase and tretinoin. These and other specific examples of chemotherapeutic agents are well known to those of skill in the art and are included within the scope of the invention.

Additional Functional Ingredients

The components of the treatment compositions according to the invention can further be combined with various functional components suitable for use treating the particular cancer or other condition. Additional functional ingredient components may include those that improve the health and/or viability of a patient and/or the cells of a patient.

In other embodiments, additional functional ingredients may be included in the compositions. The functional ingredients provide desired properties and functionalities to the compositions. For the purpose of this application, the term "functional ingredient" includes a material that when combined with the hydroxytyrosol provides a beneficial property in a particular use or treatment. Some particular examples of functional materials are discussed in more detail below, although the particular materials discussed are given by way of example only, and that a broad variety of other functional ingredients may be used.

In some embodiments, the compositions may include additional amino acids, and other functional ingredients may include, for example oleuropein, N-acetyl cysteine, antioxidants, vitamins and/or minerals, such as those disclosed in U.S. Patent Application Pub. No. US 2011-0034519 which is herein incorporated by reference in its entirety.

In some embodiments, suitable antioxidants include ascorbic acid (vitamin C) and its salts, ascorbyl esters of fatty acids, ascorbic acid derivatives (e.g., magnesium ascorbyl phosphate, sodium ascrobyl phosphate, and ascorbyl sorbate), EGCG, oleuropein, tocopherol (vitamin E), tocopherol sorbate, tocopherol acetate, other esters of tocopherol, tyrosol, butylated hydroxy benzoic acids and their salts, gallic acid and its alkyl esters such as propyl gallate, uric acid and its salts and alkyl esters, sorbic acid and its salts, lipoic acid, amines (e.g., N,N-diethylhydroxylamine and amino-guanidine), sulfhydryl compounds (e.g., glutathione), dihydroxy fumaric acid and it salts, glycine pidolate, arginine pilolate, nordihydroguaiaretic acid, bioflavinoids, curcumin, lysine, methionine, proline, superoxide dismutase, resveratrol, and other polyphenols. In other embodiment, one or more of cystine, cystine derivatives, vitamin C, tannic acid, vitamin E, vitamin E derivatives, catechin, niacin, unsaturated fatty acids, vitamin P, vitamin Q, glutathione, isoflavones, guava, selenium, oleuropein or other polyphenol(s) is further included. In a still further embodiment, one or more of N-acetyl cysteine, glycine, L-taurine, L-proline, niacinamide (vitamin B3), pyridoxine (vitamin B6), and methylsulfonylmethane is further included.

Without being limited according to various aspects of the invention, in some aspects there are benefits to providing certain combined ratios of such functional ingredients for providing additional benefits. In one embodiment, compositions contain N-acetyl cysteine and hydroxytyrosol and the weight ratio of N-acetyl cysteine to hydroxytyrosol to between 1:1 and 50:1, preferably between 10:1 and 30:1, preferably between 20:1 and 25:1, respectively. In one embodiment, compositions contain glycine and hydroxytyrosol and the weight ratio of glycine to hydroxytyrosol to between 1:1 and 50:1, preferably between 30:1 and 40:1, preferably 35:1, respectively. In another embodiment, compositions contain L-taurine and hydroxytyrosol and the weight ratio of L-taurine to hydroxytyrosol is between 1:1 and 50:1, preferably between 20:1 and 50:1, preferably between 30:1 and 40:1, and preferably about 35:1, respectively. In another embodiment, compositions contain L-proline and hydroxytyrosol and the weight ratio of L-proline to hydroxytyrosol is between 1:1 and 20:1, preferably between 1:1 and 10:1, preferably between 1:1 and 5:1, respectively. In yet a further embodiment, the compositions contain methylsulfonylmethane and hydroxytyrosol and the weight ratio of methylsulfonylmethane to hydroxytyrosol is between 1:1 and 30:1, preferably between 5:1 and 25:1, preferably between 10:1 and 20:1, respectively. In a still further embodiment, compositions contain niacinamide and hydroxytyrosol and the weight ratio of niacinamide to hydroxytyrosol to between 1:1 and 10:1, respectively. In one embodiment, the composition contains niacinamide and hydroxytyrosol and the weight ratio of niacinamide to hydroxytyrosol is between 1:1 and 5:1, preferably between 1:1 and 2:1, respectively. In a still further embodiment, the composition contains pyridoxine and hydroxytyrosol and the weight ratio of pyridoxine to hydroxytyrosol is between 1:1 and 10:1, preferably between 1:1 and 5:1, preferably between 1:1 and 2:1, respectively.

Composition Formulations

Compositions containing hydroxytyrosol may be formulated in any conventional manner. Proper formulation is dependent upon the route of administration chosen. Suitable routes of administration include, but are not limited to, oral, parenteral (e.g., intravenous, intraarterial, subcutaneous, rectal, subcutaneous, intramuscular, intraorbital, intracapsular, intraspinal, intraperitoneal, or intrasternal), topical (nasal, transdermal, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal administration.

Pharmaceutically acceptable carriers for use in the compositions of the present invention are well known to those of ordinary skill in the art and are selected based upon a number of factors: hydroxytyrosol concentration and intended bioavailability; the disease, disorder or condition being treated with the composition; the subject, his or her age, size and general condition; and the route of administration. Suitable carriers are readily determined by one of ordinary skill in the art (see, for example, J. G. Nairn, in: Remington's Pharmaceutical Science (A. Gennaro, ed.), Mack Publishing Co., Easton, Pa., (1985), pp. 1492-1517, the contents of which are incorporated herein by reference).

In general, oral routes of administration are preferred. For oral administration, the hydroxytyrosol containing compositions are preferably formulated as tablets, dispersible powders, pills, capsules, gelcaps, caplets, gels, liposomes, granules, solutions, suspensions, emulsions, syrups, elixirs, troches, dragees, lozenges, or any other dosage form which can be administered orally. Techniques and compositions for making oral dosage forms useful in the present invention are described in the following references: 7 Modern Pharmaceutics, Chapters 9 and 10 (Banker & Rhodes, Editors, 1979); Lieberman et al., Pharmaceutical Dosage Forms: Tablets (1981); and Ansel, Introduction to Pharmaceutical Dosage Forms 2nd Edition (1976).

The hydroxytyrosol containing compositions of the present invention may also be preferably formulated for parenteral administration, e.g., formulated for injection via intravenous, intraarterial, subcutaneous, rectal, subcutaneous, intramuscular, intraorbital, intracapsular, intraspinal, intraperitoneal, or intrasternal routes. The compositions of the invention for parenteral administration comprise an effective amount of hydroxytyrosol in a pharmaceutically acceptable carrier. Dosage forms suitable for parenteral administration include solutions, suspensions, dispersions, emulsions or any other dosage form which can be administered parenterally. Techniques and compositions for making parenteral dosage forms are known in the art.

Suitable carriers used in formulating liquid dosage forms for oral or parenteral administration include nonaqueous, pharmaceutically-acceptable polar solvents such as oils, alcohols, amides, esters, ethers, ketones, hydrocarbons and mixtures thereof, as well as water, saline solutions, dextrose solutions (e.g., DW5), electrolyte solutions, or any other aqueous, pharmaceutically acceptable liquid.

Suitable nonaqueous, pharmaceutically-acceptable polar solvents include, but are not limited to, alcohols (e.g., .alpha-glycerol formal, .beta-glycerol formal, 1,3-butyleneglycol, aliphatic or aromatic alcohols having 2-30 carbon atoms such as methanol, ethanol, propanol, isopropanol, butanol, t-butanol, hexanol, octanol, amylene hydrate, benzyl alcohol, glycerin (glycerol), glycol, hexylene glycol, tetrahydrofurfuryl alcohol, lauryl alcohol, cetyl alcohol, or stearyl alcohol, fatty acid esters of fatty alcohols such as polyalkylene glycols (e.g., polypropylene glycol, polyethylene glycol), sorbitan, sucrose and cholesterol); amides (e.g., dimethylacetamide (DMA), benzyl benzoate DMA, dimethylformamide, N-(.beta.-hydroxyethyl)-lactamide, N,N-dimethylacetamide amides, 2-pyrrolidinone, 1-methyl-2-pyrrolidinone, or polyvinylpyrrolidone); esters (e.g., 1-methyl-2-pyrrolidinone, 2-pyrrolidinone, acetate esters such as monoacetin, diacetin, and triacetin, aliphatic or aromatic esters such as ethyl caprylate or octanoate, alkyl oleate, benzyl benzoate, benzyl acetate, dimethylsulfoxide (DMSO), esters of glycerin such as mono, di, or tri-glyceryl citrates or tartrates, ethyl benzoate, ethyl acetate, ethyl carbonate, ethyl lactate, ethyl oleate, fatty acid esters of sorbitan, fatty acid derived PEG esters, glyceryl monostearate, glyceride esters such as mono, di, or tri-glycerides, fatty acid esters such as isopropyl myristate, fatty acid derived PEG esters such as PEG-hydroxyoleate and PEG-hydroxystearate, N-methylpyrrolidinone, pluronic 60, polyoxyethylene sorbitol oleic polyesters such as poly(ethoxylated)30-60 sorbitol poly(oleate)2-4, poly(oxyethylene)15-20 monooleate, poly(oxyethylene)15-20 mono 12-hydroxystearate, and poly(oxyethylene)15-20 mono ricinoleate, polyoxyethylene sorbitan esters such as polyoxyethylene-sorbitan monooleate, polyoxyethylene-sorbitan monopalmitate, polyoxyethylene-sorbitan monolaurate, polyoxyethylene-sorbitan monostearate, and Polysorbate® 20, 40, 60 or 80 from ICI Americas, Wilmington, Del., polyvinylpyrrolidone, alkyleneoxy modified fatty acid esters such as polyoxyl 40 hydrogenated castor oil and polyoxyethylated castor oils (e.g., Cremophor® EL solution or Cremophor® RH 40 solution), saccharide fatty acid esters (i.e., the condensation product of a monosaccharide (e.g., pentoses such as ribose, ribulose, arabinose, xylose, lyxose and xylulose, hexoses such as glucose, fructose, galactose, mannose and sorbose, trioses, tetroses, heptoses, and octoses), disaccharide (e.g., sucrose, maltose, lactose and trehalose) or oligosaccharide or mixture thereof with a C4-C22 fatty acid(s)(e.g., saturated fatty acids such as caprylic acid, capric acid, lauric acid, myristic acid, palmitic acid and stearic acid, and unsaturated fatty acids such as palmitoleic acid, oleic acid, elaidic acid, erucic acid and linoleic acid)), or steroidal esters); alkyl, aryl, or cyclic ethers having 2-30 carbon atoms (e.g., diethyl ether, tetrahydrofuran, dimethyl isosorbide, diethylene glycol monoethyl ether); glycofurol (tetrahydrofurfuryl alcohol polyethylene glycol ether); ketones having 3-30 carbon atoms (e.g., acetone, methyl ethyl ketone, methyl isobutyl ketone); aliphatic, cycloaliphatic or aromatic hydrocarbons having 4-30 carbon atoms (e.g., benzene, cyclohexane, dichloromethane, dioxolanes, hexane, n-decane, n-dodecane, n-hexane, sulfolane, tetramethylenesulfon, tetramethylenesulfoxide, toluene, dimethylsulfoxide (DMSO), or tetramethylenesulfoxide); oils of mineral, vegetable, animal, essential or synthetic origin (e.g., mineral oils such as aliphatic or wax-based hydrocarbons, aromatic hydrocarbons, mixed aliphatic and aromatic based hydrocarbons, and refined paraffin oil, vegetable oils such as linseed, tung, safflower, soybean, castor, cottonseed, groundnut, rapeseed, coconut, palm, olive, corn, corn germ, sesame, persic and peanut oil and glycerides such as mono-, di- or triglycerides, animal oils such as fish, marine, sperm, cod-liver, haliver, squalene, squalane, and shark liver oil, oleic oils, and polyoxyethylated castor oil); alkyl or aryl halides having 1-30 carbon atoms and optionally more than one halogen substituent; methylene chloride; monoethanolamine; petroleum benzin; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (Solutol® HS-15, from BASF, Ludwigshafen, Germany); polyoxyethylene glycerol; sodium laurate; sodium oleate; or sorbitan monooleate.

Methods of Treatment

The hydroxytyrosol containing compositions and/or regimens of the present invention may be used in methods for the treatment of subjects having a variety of diseases. In some embodiments, the hydroxytyrosol containing compositions and/or regimens of the present invention may be used for the treatment of cancers, for example neoplasias, chronic leukemias, non-Hodgkin's lymphoma, Hodgkin's disease, multiple myeloma, chronic myeloid leukemia (CML), acute myeloid leukemia (AML), and other cancerous tissues. In some embodiments, the hydroxytyrosol containing compositions and/or regimens of the present invention may be used for the treatment of any cancer expressing lysine specific demethylase 1 (LSD1).

In an embodiment, the treatment may be performed by administration of the hydroxytyrosol containing compositions and/or regimens to the subject in need thereof or by administration directly to the site of the tumor or other cancer cells. The treatment may be performed in conjunction with administration of a chemotherapeutic agent (e.g. a treatment regimen), either simultaneously, in the same composition or in separate compositions, or sequentially. The treatment may be performed by administration of components in any order and in any combination. The treatment may also be performed using more than one chemotherapeutic agent, or other type of treatment. Further, the treatment may be performed by providing multiple administrations of the compositions. One skilled in the art will ascertain these variations in treatment regimens employing the hydroxytyrosol compositions and/or regimens disclosed herein.

As referred to in the methods of administering hydroxytyrosol compositions, such compositions include any hydroxytyrosol-based inhibitor of the LDS1 protein. Suitable hydroxytyrosol-based inhibitor of the LDS1 protein include, for example, hydroxytyrosol, a hydroxytyrosol derived compound, a hydroxytyrosol substituted compound, a hydroxytyrosol metabolite (originating from a prodrug), and combinations of the same. A hydroxytyrosol-containing formulation may further include other functional ingredients (for example oleuropein, N-acetyl cysteine, antioxidants, vitamins, minerals, and/or amino acids), chemotherapeutic agent, carrier, diluent and/or other pharmaceutically acceptable delivery agents or the like.

The methods of the invention may be further applicable to non-cancerous condition which are treated with regimens employing chemotherapeutic agents, such as for example hepatitis C or other viral infections, ankylosing spondylitis, multiple sclerosis, Crohn's disease, psoriasis, psoriatic arthritis, rheumatoid arthritis, and scleroderma.

The combination of hydroxytyrosol-containing formulations and optionally a chemotherapeutic agent according to methods of the invention results in at least additive effects, preferably synergistic effects. The combinational therapy according to the invention results in a greater reduction in cell number, an increase in apoptosis and/or other indicator of improved treatment for a regimen disclosed herein, in comparison to either compound alone. In and additional aspect, the combination of the hydroxytyrosol and a chemotherapeutic agent according to methods of the invention may allow for a reduction in toxicity of the treatment as a similar result may be achieved with a lower dose of the chemotherapeutic agent. This is important as many of these agents are highly toxic and should be used in as small dose as possible.

Inducing Cell Death

The compositions and/or regimens of the present invention may also be used in methods for inducing cell death. The compositions and/or regimens may be administered to a cell or tissue to promote or enhance the effects of an apoptotic or necrotic agent or other treatment, or agents or treatments that arrest the cell cycle. Such compositions and/or regimens may include, but are not limited to, ultraviolet radiation or other types of radiation, staurosporine, actinomycin, rifampicin, cyclin-dependent kinase (cdk) inhibitors, indirubin, checkpoint kinase inhibitors, DNA and RNA polymerase inhibitors, DNA methyltransferase inhibitors, exonuclease inhibitors, histone acetylase and deacetylase inhibitors, and nuclease inhibitors.

Such methods may be performed, for example, by administration of an apoptotic or necrotic agent, or agents that arrest the cell cycle, either simultaneously, in the same composition or in separate compositions, or sequentially. The treatment may also be performed using more than one agent, or other type of treatment. Further, the treatment may be performed by providing multiple administrations of the compositions to the cell or tissue.

Such methods may further be performed on individuals using the routes of administration and dosages discussed above. Further, the treatment may be performed to provide hydroxytyrosol-containing formulations at the desired dose systemically or to specific locations in the body. Further, the treatment may be performed to provide hydroxytyrosol-containing formulations in multiple administrations to the individual.

Methods of Detecting Pre-Cancer Cells

The compositions of the present invention may also be used in methods for the detection of pre-cancer and/or cancerous tissues/cells in a patient. As disclosed according to the invention, contacting cancer cells with compositions of hydroxytyrosol induces genetic and epigenetic effects in those cells which can be detected. Therefore, an embodiment of this invention is the administration of the hydroxytyrosol compositions according to the various embodiments of the invention followed by detection of genetic and/or epigenetic effects to detect cancerous or pre-cancerous cells.

Such detection methods may be performed by administering the compositions according to the invention to a subject or by administration directly to a specific site of the subject. The methods may further include the collecting of cells, tissue, or other biological material from the patient. Such collection may be used for the determination of genetic and/or epigenetic effects. The detection may be performed by a single administration, or multiple administrations, and may be done by collecting a single sample or by collecting multiple samples. The detection may be performed by collecting a sample from a patient and administering the compositions according to the invention to that isolated sample.

Effects on Non-Cancer Cells

The compositions of the present invention may also be used to induce certain desired changes or effects in other cell types. As disclosed according to the invention, and as shown in FIG. 16, contacting epidermal or endothelial cells with compositions comprising, consisting of and/or consisting essentially of hydroxytyrosol improves migration, response to high glucose-induced dysfunction, and response to doxorubicin-induced damage. Further, contacting endothelial cells with compositions of hydroxytyrosol improves tubule formation/angiogenesis. Further, contacting peripheral blood mononuclear cells (PBMC) with compositions of hydroxytyrosol improves their antioxidant capacity/activity, including in the presence of high glucose (high glucose-induced dysfunction) and chemotherapeutic agents (e.g. doxorubicin-induced damage). Further still, contacting peripheral blood mononuclear cells (PBMC) with compositions of hydroxytyrosol improves cell viability. These beneficial uses of hydroxytyrosol are further confirmed by mRNA sequence and micro-array data summarized in FIG. 16, and further summarized in Table 1.

Further still, contacting muscle cells with compositions of hydroxytyrosol improves cell viability, as shown in FIG. 17. This beneficial use of the compositions of the invention is even more pronounced in the presence of chemotherapeutic agents (e.g. doxorubicin-induced damage) and oxidative stress.

Accordingly, in one embodiment of the invention, the compositions and methods are employed to achieve a protective effect, for example to improve cell viability or to treat or prevent chemotherapy-induced damage, high glucose-induced dysfunction, and/or oxidative stress in non-cancer cells, including for example, epithelial cells, endothelial cells, muscle cells, and PBMC.

Sensitizing Cancer Cells to Immune Surveillance

The hydroxytyrosol-containing formulations and other compositions of the present invention may also be used in methods to sensitize cancers, for example cancer cells, tumors, or malignancies, to surveillance by an individual's immune system. In one aspect, such methods may be performed by administration of hydroxytyrosol-containing formulations to stimulate rapid proliferation of normal peripheral blood cells, increasing the number of naturally occurring natural killer (NK) cells found in the population and enhancing cytotoxic immunity against the cancer. Such methods may be accomplished using the various routs of administration and dosing schemes discussed above. In another aspect, increased sensitization of cancer cells may be achieved by isolating immune cells from an individual, treating the immune cells with hydroxytyrosol-containing compositions ex vivo, and returning the treated cells to an individual.

Lysine Specific Demethylase 1 (LSD1)

LSD1 (also referred to as KDM1A) is a histone H3K4/K9 demethylase and epigenetic regulator with roles in both gene activation and repression. LSD1 has been shown to have increased expression in multiple cancer types. LSD1 is described in U.S. Pat. Nos. 8,323,941 and 7,741,086, which are incorporated herein by reference. LSD1 is a histone demethylase with specificity for mono- and dimethyl histone H3 lysine 4 and mono and dimethyl histone H3 lysine 9. Such histone demethylases contribute to epigenetic regulation of gene expression, which provides cells with a heritable mechanism for controlling gene expression without altering the DNA nucleotide sequence. LSD1 is highly conserved in high eukaryotes, and null mutation of LSD1 genes in mouse causes embryonic lethality.

LSD1 is a member of the flavin adenine dinucleotide (FAD)-dependent family of amine oxidases, which require FAD to oxidize the mono or dimethyl lysine to an imine intermediate that is further hydrolyzed to unmodified lysine and formaldehyde. LSD1 was identified as a component of the Ctb co-repressor complex, and as a member of the CoREST repressor complex. When the CoREST complex is targeted to lineagespecific genes, LSD1 demethylates the activating H3K4me2 mark to silence their expression. Additional repressive complexes containing LSD1 have been identified, including NRD and subsets of the HDAC complexes.

Conversely, LSD1 has been found to interact with multiple proteins/complexes that function in gene activation. LSD1 is recruited via interaction with androgen receptor or estrogen receptor for transcription of androgen receptor and estrogen receptor target genes. In this role, LSD1 is thought to demethylate the repressive H3K9me2 mark to allow for gene activation. LSD1 is also a member of a transcription elongation complex composed of ELL (elongation factor RNA polymerase II), pTEFb, AF4, and AFF4. Additionally, LSD1 is a component of an MLL supercomplex associated with active transcription. MLL itself is an epigenetic modifier as a histone methyltransferase with specificity for H3K4.

In one aspect of the present invention, hydroxytyrosol-containing formulation may be employed to alter the interactions of LSD1 is various proteins or complexes. In a preferred embodiment, hydroxytyrosol-containing formulations are employed to induce epigenetic effects, for example through inhibiting LSD1 and thereby altering H3K9 methylation and/or through altering interactions with other factors. In another aspect, hydroxytyrosol-containing formulations may be utilized to induce changes in gene expression related to particular functions, for example glucose metabolism.

Human LSD1 consists of 852 amino acids and comprises an N-terminal SWIRM domain, involved in protein interactions, and a C-terminal amine oxidase domain, which contains an insertion that forms the CoREST interacting site (the so-called "tower domain"). A truncation mutant of LSD1 lacking its N-terminal 184 residues retained full demethylase activity against methylated H3-K4 peptide substrates.

Studies investigating potential inhibitors of LSD have elucidated the protein crystal structure of LSD1 and a substrate-like peptide inhibitor, which was derived from the N-terminal 21-amino acid residues of histone H3 peptide in which lysine 4 (K4) is replaced by methionine that binds to LSD1 with high binding affinity ($K_i$=0.05 µmol/L). (Wang et al., Cancer Res. 71(23): 7238-7249 (2011)). These studies have further shown that the positively charged residues (Arg2 and Arg8) of the peptide establish favorable electrostatic interactions with a cluster of negatively charged residues on LSD1 surface that involve Asp375, Glu379, Asp553, Asp555, Asp556, Asp557, and Glu559. The funneled channel that accesses to FAD is blocked by the peptide inhibitor.

Inhibition and Inactivation of LSD1

LSD1 can be inhibited or inactivated in a number of ways. Tranylcypromine (Parnate) is a non-reversible monoamine oxidase enzymatic inhibitor of that inhibits the amine oxidase function of LSD1 by covalently modifying the FAD cofactor of LSD1. Phase II clinical trials of tranylcypromine in acute myeloid leukemia patients have already commenced.

Other enzymatic inhibitors of LSD1 have been identified, for example by Wang et al., Cancer Res. 71(23): 7238-7249 (2011), that inhibit LSD1 activity without forming a covalent bond by blocking the funneled channel that accesses to FAD. These novel inhibitors exhibited half maximal inhibitory concentrations (IC50) at 5.27-11.16 µM (5.27-11.16 e-006 M).

Willmann et al., Int. J. of Cancer 131(11): 2704-09 (2012) also reported a selective and reversible LSD1 inhibitor, Namoline, which blocks LSD1 demethylase activity in vitro and in vivo. Namoline has a reported LSD1 half maximal inhibitory concentration (IC50) of 50 µM.

The amine oxidase activity of LSD1 may also be inhibited by preventing binding of the peptide substrate. This can be accomplished by occupying the substrate binding site, by altering the conformation of the binding site, or by interacting with key amino acids that affect substrate binding, including preventing establishment of favorable electrostatic interactions with any of the cluster of negatively charged residues on LSD1 surface that involve Asp375, Glu379, Asp553, Asp555, Asp556, Asp557, and Glu559. Without being bound by any particular theory, compositions of the invention, including hydroxytyrosol, or derivatives or equivalents of hydroxytyrosol or oleuropein, may inhibit the enzymatic activity of LSD1 in any of these ways.

LSD1 can also be inhibited by blocking interactions with partner proteins. For Example, Ferrari-Amorotti et al. showed that preventing the interaction of LSD1 with the E-box-binding transcription repressor Slug suppressed motility and invasiveness of cancer cells similar to inhibition of LSD1 with Parnate. (Cancer Res. 2013 Jan. 1; 73(1):235-45 (2012)).

In addition, LSD1 can be inactivated by downregulation, using methods familiar to a person of skill in the art, including gene down regulation or targeted knock-down of the gene by RNA interference (RNAi). For example, Wang et al. ablated LSD1 expression with a specific siRNA targeted at an mRNA region that is identical between mouse and human LSD1 genes that induced a marked inhibition of cell growth and BrdUrd incorporation in cancer cells.

In one embodiment of the invention, the hydroxytyrosol-containing formulations inhibit LSD1 activity. In one aspect, hydroxytyrosol and/or oleuropein, or homologues of hydroxytyrosol and/or oleuropein, binds directly to LSD1. In a more specific aspect, hydroxytyrosol and/or oleuropein, or homologues of hydroxytyrosol and/or oleuropein, may mediate inhibition of LSD1 by interacting with, for example, the flavin group of the FAD contained in the LSD1 protein or a site close to the adenosine group (FIG. 1). In a more specific aspect, hydroxytyrosol and/or oleuropein, or homologues of hydroxytyrosol and/or oleuropein may mediate inhibition of LSD1 by interacting with specific residues on LSD1, for example the tryptophan residue at position 807 (Trp807), the phenylalanine at position 560 (Phe560), and/or the histidine at position 812 (His812).

In one aspect, LDS1 inhibition results in modification of histone methylation. Such inhibition may comprise alteration of di-methylation of lysine 9 of histone H3 (H3K9). Such alteration may comprise an increase or a decrease in H3K9 dimethylation.

LSD1 in Cancer

LSD1 has been linked to a large number of cancer types, including: non-small cell lung cancer (Lv et al., PLoS ONE 7(4): e35065. doi:10.1371/journal.pone.0035065 (2012)); breast cancer (Wu et al., PNAS 109 (41): 16654-59 (2012)); hepatocellular carcinoma (Zhao et al., Tumor Biology 34(1): 173-80 (2013)); colon cancer (Jin et al., Biochem J. 449(2): 459-68 (2013)); prostate cancer (Willmann et al., Int. J. of Cancer 131(11): 2704-09 (2012)); chondrosarcoma, Ewing's sarcoma, osteosarcoma, and rhabdomyosarcoma (Bennani-Bati et al., Human Pathology 43(8): 1300-07 (2012)); olitary fibrous tumors, synovial sarcomas, rhabdomyosarcomas, desmoplastic small round cell tumors, and malignant peripheral nerve sheath tumors (Schildhaus et al., Human Pathology 42(11): 1667-75 (2011)); teratocarcinoma, embryonic carcinoma, and seminoma or embryonic stem cells that express the stem cell markers Oct4 and Sox2 (Wang et al. Cancer Res. 71(23):7238-49 (2011)); and bladder cancer (Kauffman et al., Mol. Carcinogenesis 50(12): 931-44 (2011)), all of which are incorporated herein by reference.

Schenk et al. specifically showed LSD1 to be a therapeutic target and that it may contribute to acute myeloid leukemia (AML) pathogenesis. Inhibition of LSD1 by tranylcypromine allowed for effective treatment of AML otherwise unresponsive to all-trans-retinoic acid (ATRA) therapy. The authors suggested that LSD1 may contribute to AML pathogenesis, and inhibition of LSD1 could provide for new combinatorial therapies for AML.

In addition, Harris et al. (Cancer Cell. 2012 Apr. 17; 21(4):473-87) showed that inhibition of LSD1 prevented development of leukemia in a murine model of mixed lineage leukemia (MLL) leukemia by inducing differentiation of MLL leukemia cells. The authors suggested that LSD1 was responsible for promoting the oncongenic gene program associated with certain types of leukemia.

Conventional efforts to develop specific inhibitors of the LDS1 protein expressed in a majority of cancers have had limited success to date. In particular, development of specific inhibitors of the LDS1 protein at the FAD or the funneled channel that accesses to FAD, including Asp375, Glu379, Asp553, Asp555, Asp556, Asp557, and Glu559 sites have not resulted in significant advances in cancer treatment and/or prevention.

LSD1 has also been implicated in the activation of HIV viral transcription (Sakane et al., PLoS Pathology 7(8): e1002184. doi:10.1371/journal.ppat.1002184), and in HIV-1 gene silencing in latently infected cells (Le Douce et al., Nucl. Acids Res. (2012) 40 (5): 1904-1915). Further, LSD1 has been linked to both repression of inflammation (Janzer et al., Biochem Biophys Res Commun. 421(4):665-70 (2012)) and hypertension (Williams et al., Am J Hypertens. 25(7):812-17 (2012)).

Hydroxytyrosol Interaction with LSD

Without being limited to a particular theory, it is believed that hydroxytyrosol interacts directly with LSD1 in a manner that inhibits the FAD-dependent oxidation of methylated lysine, either by binding FAD or by blocking the funneled channel that accesses to FAD. In the alternative, hydroxytyrosol may block peptide ligand binding by inhabiting the ligand binding site, altering the conformation of the ligand binding site of LSD1, or interacting with key amino acid residues that affect substrate binding by LSD1. The invention therefore embodies any derivative of oleuropein or hydroxytyrosol, or structural mimic or homologue thereof, that exhibits binding and/or inhibition characteristics similar to hydroxytyrosol.

Figure 9A:
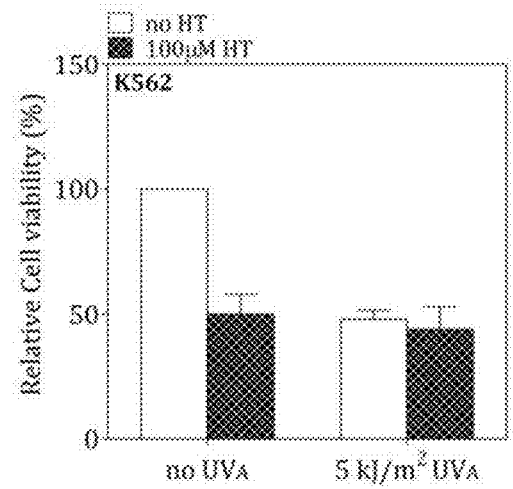
FIG. 9 (A-C) shows hydroxytyrosol enhances DNA damaging effects of UVA radiation. (A-B) Cell cytotoxicity and apoptosis were measured by (A) the Cell-Titer Blue assay kit and (B) the Apo-ONE homogenous caspase 3/7 assay kit respectively. (C) Hydroxytyrosol enhances DNA damage induced by UVA in erythroleukemic K562 cells. K562 cells were pre-treated with 100 μM hydroxytyrosol (HT) for 24 hours prior to 1 hour incubation following exposure to 5 kJ/m2 UVA. Cells were then stained for γH2AX (green), a molecular marker of DNA double strand breaks. Mean±standard deviations from a single experiment performed in duplicate are shown; level of significance was accepted at *$p<0.05$ and **$p<0.01$.
Figure 9B:
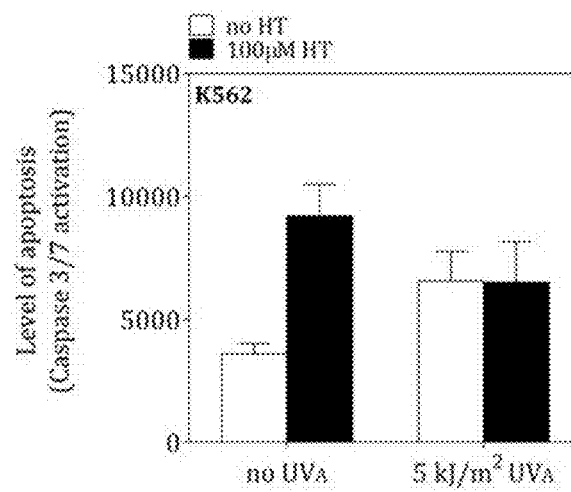
Figure 9C:
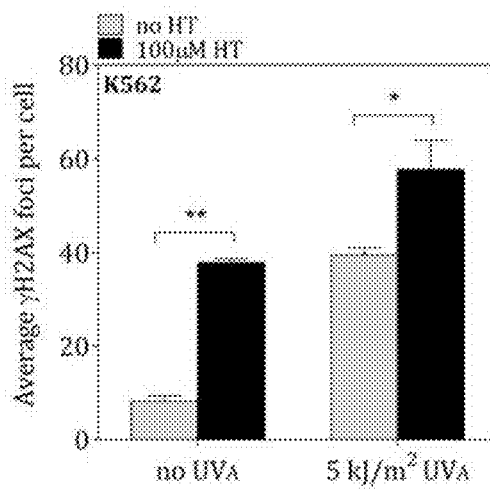

As demonstrated by this invention, hydroxytyrosol inhibits the enzymatic activity of LSD1 (FIG. 9). Unlike other inhibitors of LSD1, hydroxytyrosol is a naturally occurring compound, lacking the substantial toxic side effects of other inhibitors. According to the invention, LSD1 is inhibited by exposure to hydroxytyrosol or compositions comprising hydroxytyrosol. This inhibition of LSD1 prevents the growth, development, migration and metastasis of cancer cells. Although not bound by this exemplary embodiment, hydroxytyrosol can be provided in order to inhibit enzymatic activity, prevent association with co-factors or partner proteins, or decrease expression of LSD1 in target cancer cells, thereby preventing the growth, development, migration or metastasis of cancer cells.

In addition, hydroxytyrosol, or derivatives of hydroxytyrosol and/or oleuropein, may inhibit LSD1 by preventing the binding of partner proteins or cofactors, or by downregulating the protein. It is understood that inhibition of LSD1 by hydroxytyrosol, or derivatives/equivalents of hydroxytyrosol or oleuropein, can be by one or more of these mechanisms.

In another embodiment, hydroxytyrosol is used to treat cancer in an individual by inhibiting LSD1 and thereby inhibiting cancer cell growth, development, or metastasis. In a preferred embodiment, the individual is screened for a cancer that is linked to LSD1, and if the individual has a cancer linked to LSD1 the individual is treated with a composition of the present invention. In another embodiment, hydroxytyrosol is used to prevent the growth or development of cancer in an individual.

Methods of Detecting LSD1-Positive Cancer

The compositions of the present invention may also be used to detect cancer cells that express LSD1 or are susceptible to LSD1 inhibition. As disclosed according to the invention, cancer cells can be assayed for sensitivity to LSD1 inhibition by contacting with compositions comprising hydroxytyrosol. Sensitivity can be measured using a variety of indicators, including, for example: cell growth, proliferation and/or death; alteration of gene expression and epigenetic effects; cell invasion; cell migration; cell adhesion; and/or expression of cancer cell markers.

In a further embodiment, detection of hydroxytyrosol sensitivity of cancer cells may be used as part of a method for treatment of an individual with an LSD1-expressing cancer. According to the invention, and individual may be screened for a cancer sensitive to hydroxytyrosol via LSD1 inhibition, and upon identification of a hydroxytyrosol-sensitive cancer, the individual may be administered a composition of hydroxytyrosol sufficient to treat or prevent development of the cancer.

It is understood from the disclosures made herein that in vitro efficacy of treatment with hydroxytyrosol, alone or as part of an exemplary formulation, or in conjunction with additional treatments, is predictive of in vivo efficacy. For example, dosing schemes for chemotherapeutic agents doxorubicin, vinblastine, and mitomycin C are well understood in the art. Further, according to aspects of the invention dosing for administration of hydroxytyrosol, alone or as part of an exemplary formulation, or in conjunction with additional treatments, wherein the hydroxytyrosol or formulation is administered at 0.5 mg/kg body weight for 5 days per week for 6 weeks.

All publications and patent applications in this specification are indicative of the level of ordinary skill in the art to which this invention pertains. All publications and patent applications are herein incorporated by reference to the same extent as if each individual publication or patent application was specifically and individually indicated as incorporated by reference.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, - - - can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

Structure and Predicted Binding of Hydroxytyrosol to Lysine Demethylase 1 (LSD1)
Methods
Docking The molecular docking program, AutoDock Vina, was used to propose energetically favorable binding sites for hydroxytyrosol on human LSD1. Docking was performed on the crystal structure of LSD1 complexed with FAD covalently bonded to tranylcypromine (PDBID 2EJR). Prior to docking calculations, all waters, as well as the tranylcypromine adduct, were removed to create a PDB file containing only LSD1 and FAD. Although the control compound, tranylcypromine, is known to inhibit LSD1 via covalent attachment to the co-factor FAD, preliminary work does not assume covalent bonding between HT and FAD. This enables identification of possible HT binding sites both near and distal from the FAD pocket. On the other hand, predicted binding sites close to FAD may enable the identification of candidate structures for FAD with HT adduct. Predicted docking poses may also help guide determination and refinement of the HT-FAD chemical structure and conformation within the protein-inhibitor co-crystal structure. In addition, we modeled the novel LSD1 inhibitor 2d (1,15-bis{N 5-[3,3-(diphenyl)propyl]-N 1-biguanido}-4,12-diazapentadecane) and compared binding energies to those of HT.

The hydroxytyrosol ligand structure was obtained from the ZINC small-molecule structure database and converted to PDB format using Deepview. LSD1-FAD and hydroxytyrosol PDB files were pre-processed using PyRx to create their corresponding PDBQT files for use with Autodock Vina. All five rotatable torsions for hydroxytyrosol were activated while LSD1-FAD was assumed to be rigid. PyRx was used to define the ligand search grid with the center coinciding with those of the amine oxidase domain, with (x, y, z) dimensions of 65 Å3. The grid encompasses the amine oxidase domain surface and enables exhaustive search of potential binding sites. The searches were each conducted with exhaustiveness of 2000. Calculations were performed on a 180 node 64-bit Intel® Xeon® ES-2670 cluster housed at the Victorian Partnership for Advanced Computing (VPAC) facilities, utilizing 16 nodes (256 cores) per docking search. The top 20 predicted hydroxytyrosol binding poses were visualized and analyzed using VMD version 1.9.2.

Results and Discussion

Figure 1B:
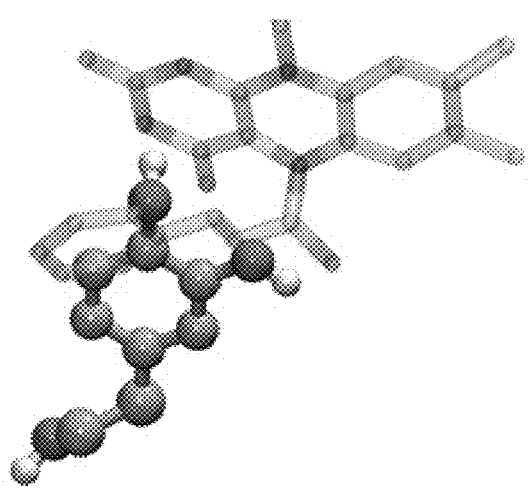
Figure 2A:
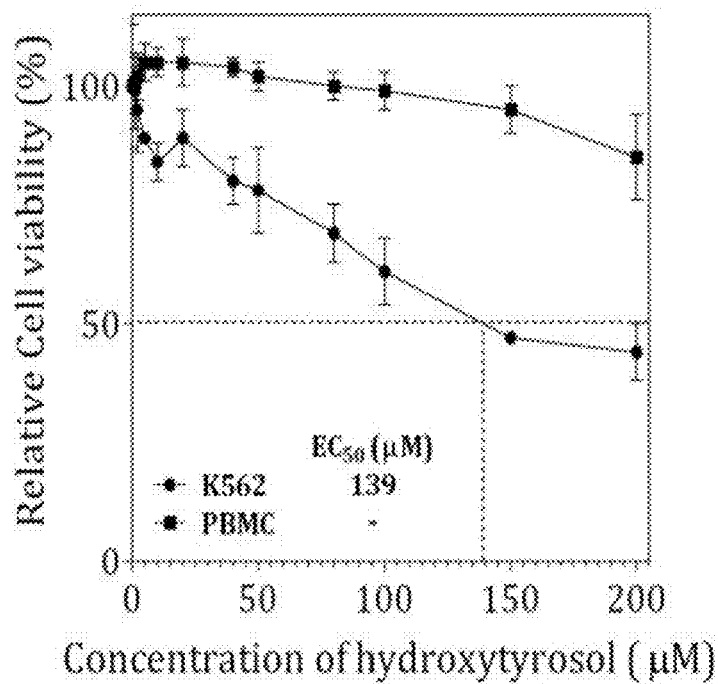
FIG. 2 (A-D) shows reduction in cell viability of erythroleukemic K562 cells following exposure to hydroxytyrosol but no changes in viability in PBMC. (A) shows viability in K562 cells and PBMC exposed to increasing concentrations of hydroxytyrosol. (B) shows viability in K562 cells and PBMC exposed to increasing concentrations of oleuropein. (C) shows viability in K562 cells and PBMC exposed to increasing concentrations of tyrosol. (D) shows viability in K562 cells and PBMC exposed to increasing concentrations of homovanillic acid. Mean±standard deviations from a single experiment performed in triplicate are shown; total of 2 independent experiments tested.
Figure 2B:
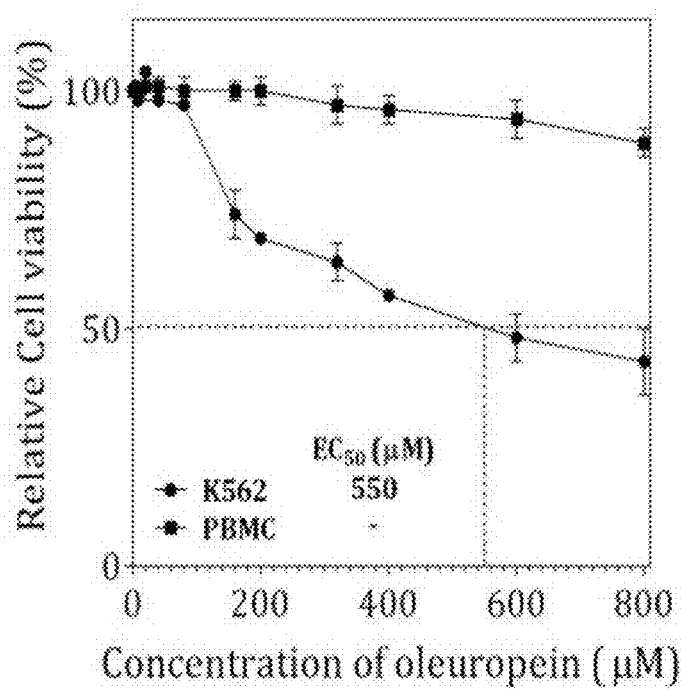
Figure 2C:
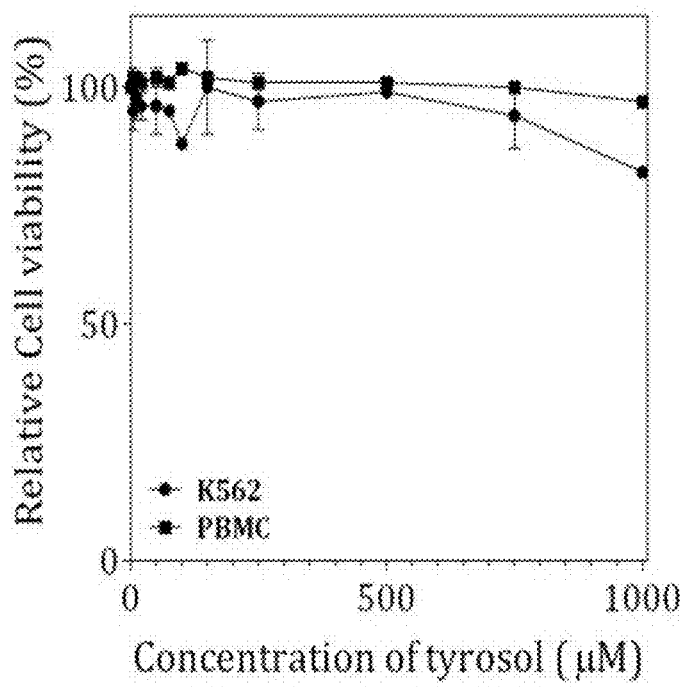
Figure 2D:
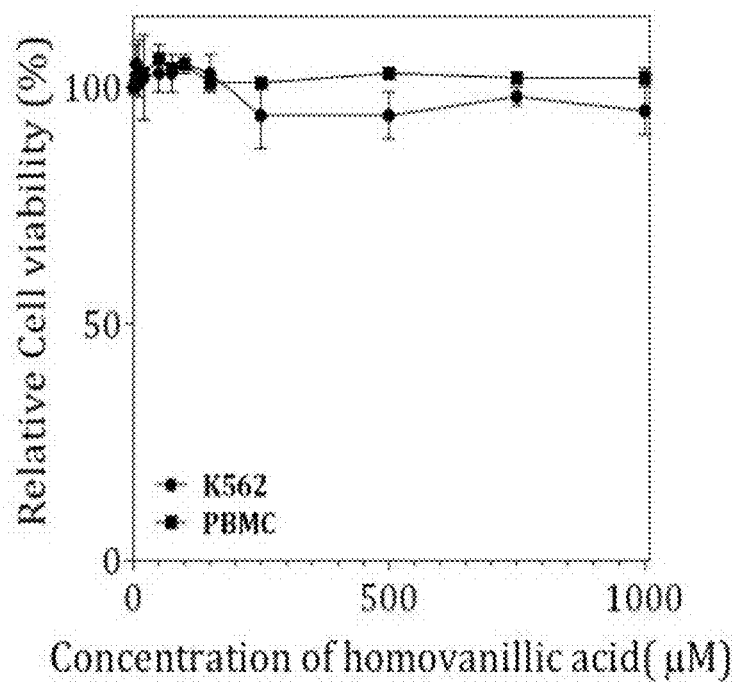
Figure 27A:
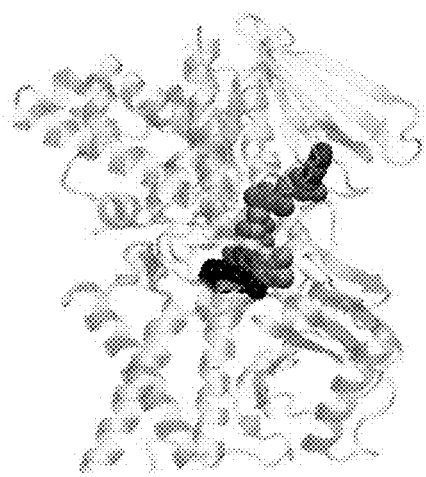
FIG. 27 (A-C) shows structure and predicted binding of hydroxytyrosol to lysine demethylase 1 (LSD1) compared to tranylcypromine and 2d. Structure of human LSD1 (ribbon) amine oxidase domain complexed with FAD with tranylcypromine adduct (space-filling spheres) from PDBID 2EJR (A); and the top 20 predicted docking positions of hydroxytyrosol (black lines), indicating several possible binding sites (B). Two possible binding sites are identified: one close to the flavin group (bottom), another close to the adenosine group (top). Top ranked binding mode of 2d to LSD1 which places 2d directly at the catalytic site (near the edge of FAD) (C). The predicted binding affinities are for competitive binding of 2d: −7.4 kcal/mol, Kd=$5.97*10^{-6}$ mol/L (at 300K) and hydroxytyrosol: −5.8 kcal/mol, Kd=$5.95*10^{-6}$ mol/L (at 300K).
Figure 27B:
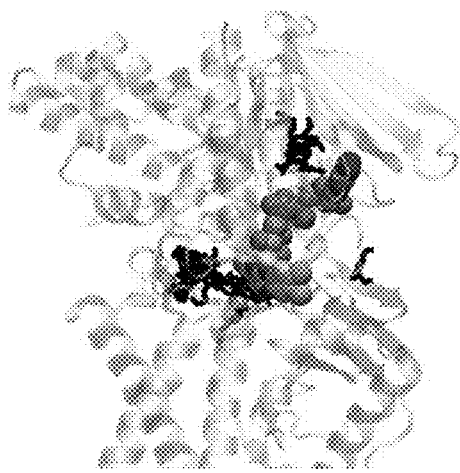
Figure 27C:
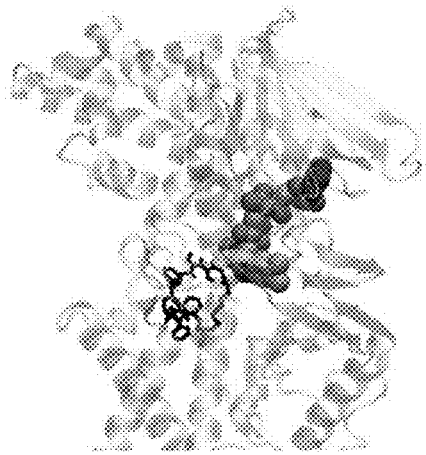

Preliminary docking calculations of HT to FAD-bound LSD1 indicate two "clusters" of docking solutions, indicative of the possible presence of two distinct favorable binding sites for this inhibitor. The most energetically favorable site is close to the flavin group of the FAD, while the other site is close to the adenosine group. The binding pose with the highest predicted binding affinity lies close to the flavin group, and is illustrated in FIG. 1 and FIG. 27. The HT ring is predicted to form close contacts with several aromatic and basic residues—in particular the tryptophan residue at position 807 (Trp807), the phenylalanine at position 560 (Phe560), and/or the histidine at position 812 (His812)—suggesting the possible importance of $\pi$-$\pi$ and cation-$\pi$ interactions in stabilizing the binding between LSD1 and HT (FIG. 1A). Also of interest is a predicted docking site which directly overlaps with the position of the tranylcypromine adduct in 2EJR (FIG. 1B). This binding pose may help in identifying positions on the flavin ring which may covalently bind HT, in a manner analogous to the covalent linkage of tranylcypromine to FAD as part of its inhibition mechanism.

The docking studies indicate that HT binds to LSD1 with an affinity analogous to 2d. The predicted binding affinities are for competitive binding of 2d: −7.4 kcal/mol, Kd=5.97× $10^{-6}$ mol/L (at 300K) and HT: −5.8 kcal/mol, Kd=5.95×$10^{-6}$ mol/L (at 300K).

Example 2

Effects of Polyphenols from Olive in Malignant Erythroleukemic and Normal Peripheral Blood Cells
Summary:

Hydroxytyrosol induces cell-death, apoptosis and DNA double-strand breaks in erythroleukemic cells but not in normal peripheral blood mononuclear cells.
Methods
Cell Culture Human chronic myelogenous leukemia K562 cells were obtained from the American Type Culture Collection (Manassas, Va., USA) and maintained in complete-Royal Park Memorial Institute (RPMI) 1640 medium supplemented with 20 mmol/L HEPES (pH 7.4; GIBCO-Invitrogen, Carlsbad, Calif., USA), 10% (v/v) fetal bovine serum (FBS), 2 mmol/L L-glutamine (GIBCO-Invitrogen), and 80 units gentamicin (GIBCO-Invitrogen). Cells were cultured in suspension in a humidified atmosphere of 5% (v/v) $CO_2$ at 37° C. and were maintained in exponential growth phase. For maintenance, cells were passaged twice per week and seeded at ratios 1:10. Human peripheral blood mononuclear cells (PBMCs) were fractionated using the Ficoll Plaque fractionation method from whole blood obtained from the Australian Red Cross Blood Bank (ARCB) under ethic approval (#304/12). Cells were harvested fresh on the day of the experiments and maintained in complete-RPMI-1640 medium supplemented with 10% FBS, 2 mM L-glutamine and 20 µg/mL gentamicin at 37° C., 5% (v/v) $CO_2$.
Cell Viability and Apoptosis Cells were seeded at densities of 7,500 cells/in black flat bottom 96-well plates (Nalge Nunc, Penfield, N.Y., USA) and treated with a dose response of hydroxytyrosol (0-200 µM), oleuropein (0-800 µM), tyrosol (0-1000 µM) and homovanilic acid (0-1000 µM) for 24 hours at 37° C., 5% (v/v) $CO_2$. Cell viability was determined after 24 hour exposure to hydroxytyrosol and measured using the Cell-Titer Blue® Assay kit (Promega, Madison, Wis., USA) according to the manufacturer's instructions. Cell-Titer Blue reagent was added to each well and incubated for 4 hours at 37° C., 5% $CO_2$, before reading fluorescence intensity (550 nm excitation; 615 nm emission) using the Perkin Elmer Victor3 (Perkin Elmer, MA, USA) multi-label plate reader.
γH2AX Immunofluorescence.

Cells were seeded at densities of $1×10^6$/mL in 24 well culture (Nalge Nunc, New York, USA) and treated with hydroxytyrosol (0, 20, 100 μM), for 24 hours at 37° C., 5% (v/v) $CO_2$. Cells were then stained and quantified for the number of γH2AX foci per cell nuclei. Briefly, using cytofunnels and filter cards, aliquots of 4504 were cytospun (Shandon, Inc.) for 5 minutes at 500 rpm onto Poly-o-lysine slides (Menzel-Glaser, Germany). All cells were then fixed for 10 minutes with 4% paraformaldehyde (Sigma-Aldrich, USA), washed once for five minutes with PBS without calcium and magnesium and permeabilized using 0.1% Triton X-100(Sigma-Aldrich, USA) for 10 minutes at room temperature. After three consecutive 5 minute washes with PBS without calcium and magnesium, cells were blocked in 1% BSA to reduce non specific binding for 20 minutes. After removal of blocking solution, cells were incubated in, mouse monoclonal anti-phospho-histone H2AX antibody (Upstate, New York, USA) diluted in 1% BSA (1:500) in a dark humidified environment for one hour on a rotating platform at room temperature. Following three consecutive washes, cells were exposed to a secondary goat anti-mouse antibody (1:500 in 1% BSA) conjugated with Alexa-488 (Molecular Probes, Oregon, USA) and incubated for 1 hour in a dark humidified environment on a rotating platform at room temperature. Following three consecutive washes cells were incubated in TO-PRO3 (Invitrogen, Molecular Probes, Eugene Oreg., USA) diluted in PBS in a 1:1000 dilution for 20 minutes in the dark on a rotating platform. After two 5 minute washes in PBS, cells were mounted with prolong Gold antifade solution (Invitrogen Molecular Probes, Eugene, Oreg., USA), coverslipped (Biolab, VIC, AUS) and sealed with nail polish. Slides were incubated overnight at 4° C. before imaging.

Images were acquired using a Zeiss LSM 510 Meta laser confocal microscope fitted with a Z-stage motor and 63× oil plan apochromat objective with a refractive index of 1.40. Argon (Alexa 488) and Neon (TOPRO3) lasers were acquired to visualize γH2AX foci and DNA double strand breaks. A step size of 0.5 μm was used, taking 8-16 optical Z-slices of the cells for each microscopic field. A pinhole size of 1 was used to maximize the spatial resolution. Images required for γH2AX quantification were acquired in 512× 512 pixel format and loaded into Image J (Fiji version 1.44a). Images used in the presentation of γH2AX foci formation or DNA double strand breaks repair proteins were acquired in a 1024×1024 pixel format. A minimum of 100 cells were imaged for each experimental group for all cell types.

Figure 3A:
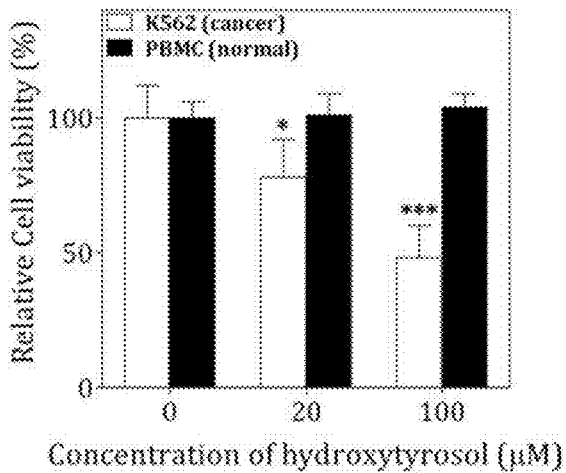
FIG. 3 (A-C) shows induction of cell death, apoptosis, and DNA double-breaks in malignant erythroleukemic K562 cells but not in normal peripheral blood cells. *$p<0.05$, ***$p<0.001$ (A) shows viability of cancer cells and non-cancer cells following exposure to hydroxytyrosol according to an exemplary embodiment of the invention. K562 leukemia cells or normal peripheral blood mononuclear cells (PBMC) were exposed to increasing concentrations of hydroxytyrosol for 24 hours, followed by determination of cell viability using commercially available kits. (B) shows amount of apoptosis in cancer cells and non-cancer cells following exposure to hydroxytyrosol according to an exemplary embodiment of the invention. K562 leukemia cells or normal peripheral blood mononuclear cells (PBMC) were exposed to increasing concentrations of hydroxytyrosol for 24 hours, followed by determination of cell apoptosis using commercially available kits. (C) shows quantification of DNA double-strand breaks in cancer cells and non-cancer cells following exposure to hydroxytyrosol according to an exemplary embodiment of the invention. K562 leukemia cells or normal peripheral blood mononuclear cells (PBMC) were exposed to increasing concentrations of hydroxytyrosol for 24 hours. The cells were fixed, permeablized, and exposed to an antibody to detect double-strand breaks in the cells' DNA. The double-strand DNA breaks in the cells were visualized and quantified.
Figure 3B:
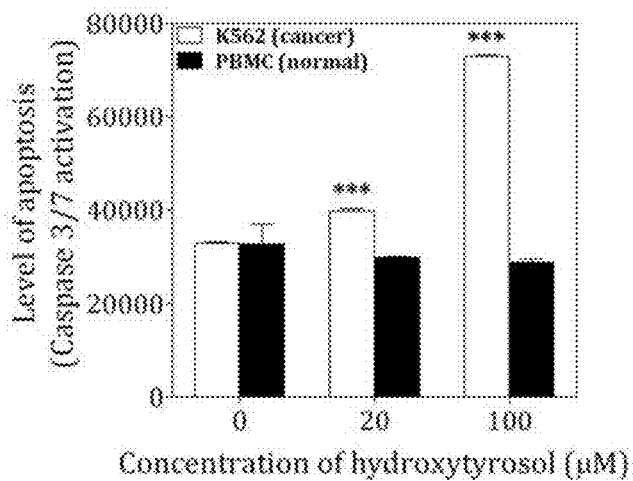
Figure 3C:
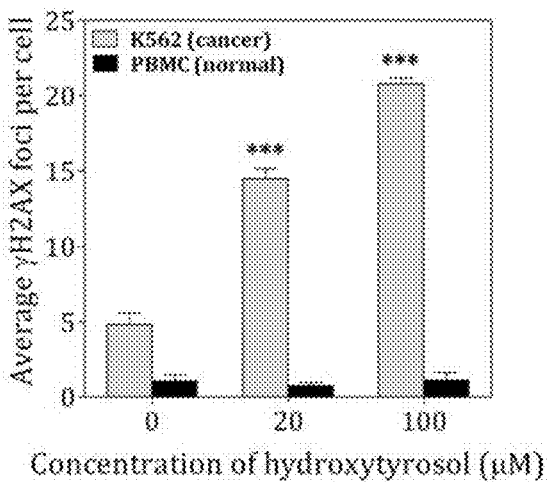
Figure 4A:
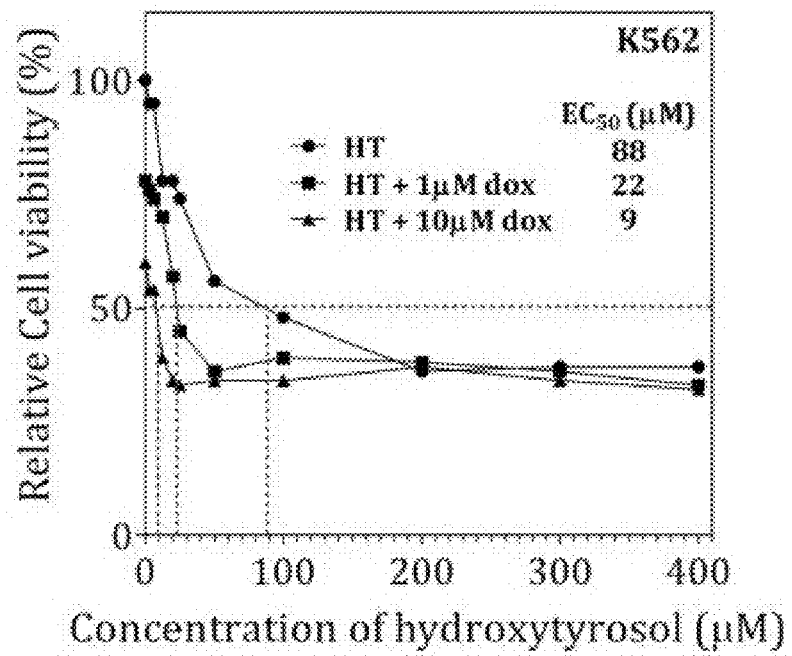
FIG. 4 (A-D) shows a synergistic reduction in cell viability and increased apoptosis in erythroleukemic K562 cells but not PBMC induced by the combination of hydroxytyrosol and chemotherapy. (A) shows cell viability in K562 cells upon treatment with increasing concentrations of hydroxytyrosol alone, or in combination with 1 or 10 $\mu$M doxorubicin. (B) shows levels of apoptosis in K562 cells upon treatment with increasing concentrations of hydroxytyrosol alone, or in combination with 1 or 10 $\mu$M doxorubicin. (C) shows cell viability in PBMC upon treatment with increasing concentrations of hydroxytyrosol alone, or in combination with 1 or 10 $\mu$M doxorubicin. (D) shows levels of apoptosis in PBMC upon treatment with increasing concentrations of hydroxytyrosol alone, or in combination with 1 or 10 $\mu$M doxorubicin. Mean±standard deviations from a single experiment performed in triplicate are shown; total of 3 independent experiments tested.
Figure 4B:
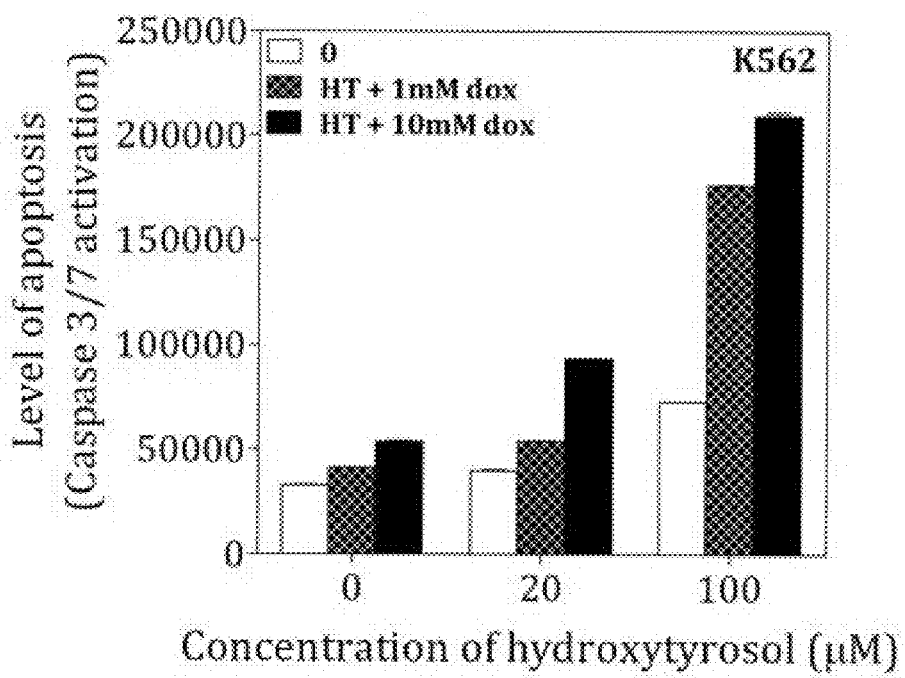
Figure 4C:
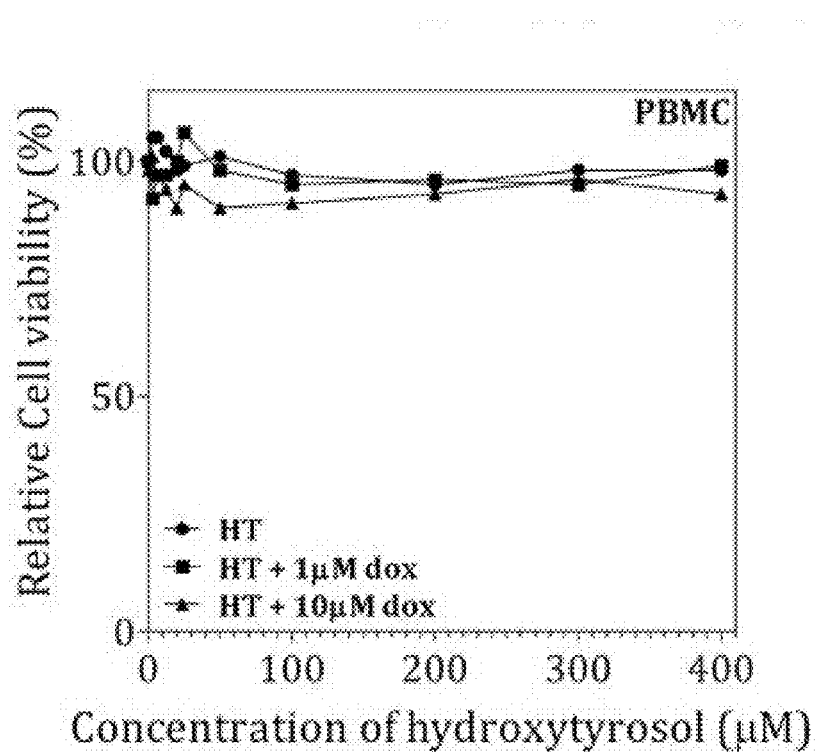
Figure 4D:
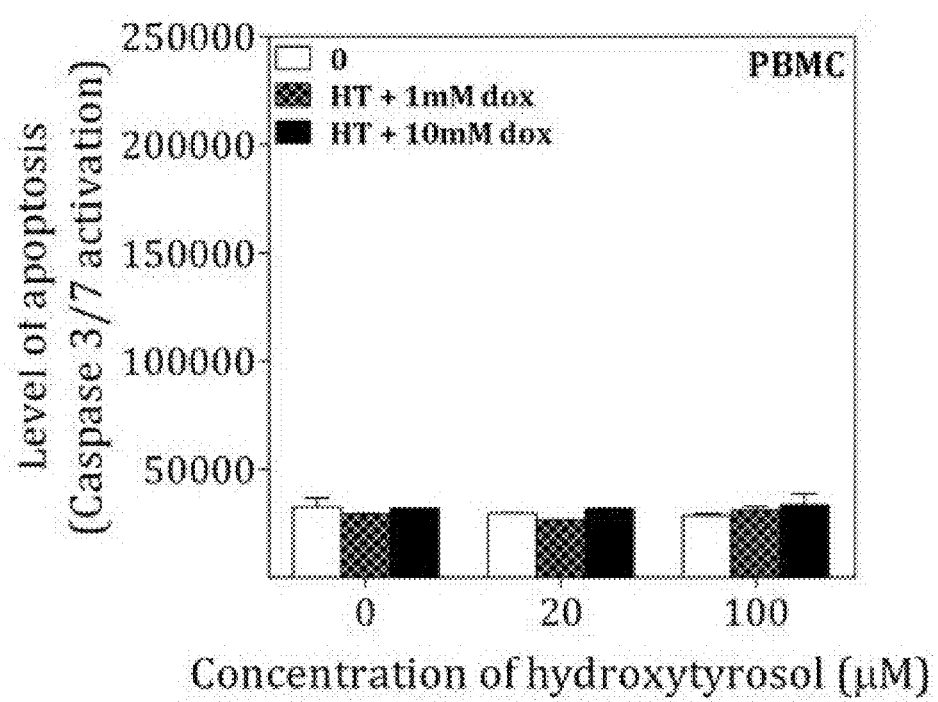

Image J software was used for the quantification of foci in all experiments. Confocal images (lsm files) acquired in Z-series were loaded and the Maximum Z-projection tool was applied to stack individual colors into a 2D image and minimize the loss of dull foci. To analyze more than one cell per image stack, from the nucleus (blue) image, each individual nucleus was defined by manually drawing regions around the nuclei. Nuclei which were not fully in view, dull, out of plan or overlapping were carefully not selected to reduce error in the determination of foci number. The area selected to analyze foci could be automatically transferred to the foci (green) maximum projection image by selecting the corresponding green image. Now clearly defined nuclear regions were selected, numbers of foci were quantified by using the find maxima tool. By selecting the outpoint type as point selection and ticking the preview point selection box, a noise tolerance was selected by carefully comparing visual inspection of foci with automated counts. A noise tolerance was typically chosen between 50 and 1000. Foci were now quantified as a total number for all cells selected. The average number of foci per nucleus was calculated and recorded into Excel spread sheets (Microsoft, Redmond, Wash., USA). A minimum of 100 cells were analyzed for each experiment group with noise tolerance kept constant for the entire analysis.
Statistical Analysis Statistical analysis was measured using Prism (version 5, GraphPad Software, San Diego, Calif., USA). A one-way analysis of variance (ANOVA) was employed, with a Bonferroni post-test to determine the statistical significance between differing treatments. The level of significance was accepted at *$p<0.05$, $p<0.01$ and *$p<0.001$.
Results and Discussion Our findings indicate that hydroxytyrosol induces celldeath and apoptosis preferentially in chronic myeloid leukemic K562 cells compared to normal peripheral blood mononuclear cells (PBMC) (FIG. 2). Using Cell Titer Blue® cell viability assay kit, the cell viability of K562 cells was significantly reduced in a dose dependent manner following treatment with 20 or 100 μM of hydroxytyrosol for 24 hours. In addition, these effects were not reciprocated in the normal PBMC cells and cell viability remained at 100%. Similarly, the Apo-ONE Homogeneous Caspase 3/7 assay kit was employed to levels of caspase 3/7 activity within the cells following hydroxytyrosol. Again, a significant dose dependent increase in caspase 3/7 apoptotic activity was observed in the K562 cells that was not mirrored in the PBMC cells. Using γH2AX investigations, our findings indicate that hydroxytyrosol induces significant DNA-double strand breaks indicated by accumulation of γH2AX in K562, increasing genomic instability and decreasing cell integrity (FIG. 3). These affects were not seen in the PBMC cell.

Example 3

Effects of Combinations of Doxorubicin and Hydroxytyrosol in Malignant Erythroleukemic and Normal Peripheral Blood Cells Summary:

Hydroxytyrosol augments the cytotoxic, apoptotic and DNA damaging effects of doxorubicin in human erythroleukemic cells but in normal peripheral blood mononuclear cells.

Methods
Cell Treatments

Cells were seeded at densities of $1×10^6$/mL in 24 well cultures (Nalge Nunc, New York, USA) and treated with 0, 20, or 100 μM hydroxytyrosol for 24 hours prior to one hour incubation in 1 μM doxorubicin. The cells were then washed twice and incubated for a further 24 hours in fresh media; 37° C., 5% (v/v) $CO_2$.

Alternatively Cells were seeded at densities of 7,500 cells/in black flat bottom 96-well plates (Nalge Nunc, Penfield, N.Y., USA) and treated with 100 μM hydroxytyrosol for 24 hours at 37° C., 5% (v/v) $CO_2$. Following incubation cells were either treated with 1 or 10 μM doxorubicin, 1 μM mitomycin C, 100 ng/mL vinblastin, 5 $kJ/m^2$ UVA or 2 Gy (137Cs) and incubated for a further 24 hours before measuring cytotoxic and apoptotic effects. Cell-Titer Blue reagent (20 μl per 100 μL) was added to each well and mixed gently for 5 sec prior to 4 hr incubation at 37° C. in a humidified atmosphere of 5% $CO_2$. Fluorescence intensity ($\lambda$ex=550 nm and $\lambda$em=615 nm) was determined using a Perkin Elmer Victor3 multilabel microplate counter (PerkinElmer, Waltham, Mass., USA). Data were expressed as % relative cell viability compared to untreated cells after correction of subtracting the media control fluorescence reading.

Apoptosis was determined by cell lysis prior to measuring caspase-3/7 enzymatic activity with Apo-ONE Homogeneous Caspase-3/7 Assay kit (Promega, Wis., USA), according to the manufacturer's instructions. Following determination of growth inhibition as described above, Apo-1 substrate/buffer mix was added to each well at a ratio of 1:1 and incubated for 4 hours on a rotating platform in the dark at 22° C. The fluorescence intensity ($\lambda$ex=485 nm and $\lambda$em=525 nm) was determined on a Victor3 multilabel plate counter (PerkinElmer, Waltham, Mass., USA). Apoptosis was reported as the change in fluorescence over 4 hours and after subtraction of the media control.

DNA Damage Cell Treatments

Cells were seeded at densities of $0.5 \times 10^6$/mL in 24 well cultures (Nalge Nunc, New York, USA) and treated with or without 100 μM hydroxytyrosol for 24 hours prior to one hour incubation in 1 μM doxorubicin. The cells were then washed twice and incubated for a further 24 hours in fresh media; 37° C., 5% (v/v) $CO_2$ prior to staining for γH2AX. In separate experiments were treated with 1 μM mitomycin C or 100 ng/mL vinblastin for 2 hours following treatment with hydroxytyrosol, or were exposed to 5 kJ/m$^2$ UVA or 2 Gy (137Cs) and incubated for a further 1 hour before fixing and staining for γH2AX.

γH2AX Immunofluorescence.

Following combinations treatments cells were then stained and quantified for the number of γH2AX foci per cell nuclei. Briefly, using cytofunnels and filter cards, aliquots of 450 μL were cytospun (Shandon, Inc.) for 5 minutes at 500 rpm onto Poly-o-lysine slides (Menzel-Glaser, Germany). All cells were then fixed for 10 minutes with 4% paraformaldehyde (Sigma-Aldrich, USA), washed once for five minutes with PBS without calcium and magnesium and permeabilized using 0.1% Triton X-100 (Sigma-Aldrich, USA) for 10 minutes at room temperature. After three consecutive 5 minute washes with PBS without calcium and magnesium, cells were blocked in 1% BSA to reduce non specific binding for 20 minutes. After removal of blocking solution, cells were incubated in, mouse monoclonal anti-phospho-histone H2AX antibody (Upstate, New York, USA) diluted in 1% BSA (1:500) in a dark humidified environment for one hour on a rotating platform at room temperature. Following three consecutive washes, cells were exposed to a secondary goat anti-mouse antibody (1:500 in 1% BSA) conjugated with Alexa-488 (Molecular Probes, Oregon, USA) and incubated for 1 hour in a dark humidified environment on a rotating platform at room temperature. Following three consecutive washes cells were incubated in TO-PRO3 (Invitrogen, Molecular Probes, Eugene Oreg., USA) diluted in PBS in a 1:1000 dilution for 10 minutes in the dark on a rotating platform. After two 5 minute washes in PBS, cells were mounted with prolong Gold antifade solution (Invitrogen Molecular Probes, Eugene, Oreg., USA), coverslipped (Biolab, VIC, AUS) and sealed with nail polish. Slides were incubated overnight at 4° C. before imaging.

Images were acquired using a Zeiss LSM 510 Meta laser confocal microscope fitted with a Z-stage motor and 63× oil plan apochromat objective with a refractive index of 1.40. Argon (Alexa 488) and Neon (TOPRO3) lasers were acquired to visualize γH2AX foci and DNA double strand breaks. A step size of 0.5 μm was used, taking 8-16 optical Z-slices of the cells for each microscopic field. A pinhole size of 1 was used to maximize the spatial resolution. Images required for γH2AX quantification were acquired in 512× 512 pixel format and loaded into Image J (Fiji version 1.44a). Images used in the presentation of γH2AX foci formation or DNA double strand breaks repair proteins were acquired in a 1024×1024 pixel format. A minimum of 100 cells were imaged for each experimental group for all cell types.

Image J software was used for the quantification of foci in all experiments. Confocal images (lsm files) acquired in Z-series were loaded and the Maximum Z-projection tool was applied to stack individual colors into a 2D image and minimize the loss of dull foci. To analyses more than one cell per image stack, from the nucleus (blue) image, each individual nucleus was defined by manually drawing regions around the nuclei. Nuclei which were not fully in view, dull, out of plan or overlapping were carefully not selected to reduce error in the determination of foci number. The area selected to analyses foci could be automatically transferred to the foci (green) maximum projection image by selecting the corresponding green image. Now clearly defined nuclear regions were selected, numbers of foci were quantified by using the find maxima tool. By selecting the outpoint type as point selection and ticking the preview point selection box, a noise tolerance was selected by carefully comparing visual inspection of foci with automated counts. A noise tolerance was typically chosen between 50 and 1000. Foci were now quantified as a total number for all cells selected. The average number of foci per nucleus was calculated and recorded into Excel spread sheets (Microsoft, Redmond, Wash., USA). A minimum of 100 cells were analyzed for each experiment group with noise tolerance kept constant for the entire analysis.

Statistical Analysis

Statistical analysis was measured using Prism (version 5, GraphPad Software, San Diego, Calif., USA). A one-way analysis of variance (ANOVA) was employed, with a Bonferroni post-test to determine the statistical significance between differing treatments. The level of significance was accepted at *$p<0.05$, $p<0.01$ and *$p<0.001$.

Cell-Titer Blue reagent (20 μl per 100 μL) was added to each well and mixed gently for 5 sec prior to 4 hr incubation at 37° C. in a humidified atmosphere of 5% $CO_2$. Fluorescence intensity ($\lambda$ex=550 nm and $\lambda$em=615 nm) was determined using a Perkin Elmer Victor3 multilabel microplate counter (PerkinElmer, Waltham, Mass., USA). Data were expressed as % relative cell viability compared to untreated cells after correction of subtracting the media control fluorescence reading.

Apoptosis was determined by cell lysis prior to measuring caspase-3/7 enzymatic activity with Apo-ONE Homogeneous Caspase-3/7 Assay kit (Promega, Wis., USA), according to the manufacturer's instructions. Following determination of growth inhibition as described above, Apo-1 substrate/buffer mix was added to each well at a ratio of 1:1 and incubated for 4 hours on a rotating platform in the dark at 22° C. The fluorescence intensity ($\lambda$ex=485 nm and $\lambda$em=525 nm) was determined on a Victor3 multilabel plate counter (PerkinElmer, Waltham, Mass., USA). Apoptosis was reported as the change in fluorescence over 4 hours and after subtraction of the media control.

Results and Discussion

Figure 5A:
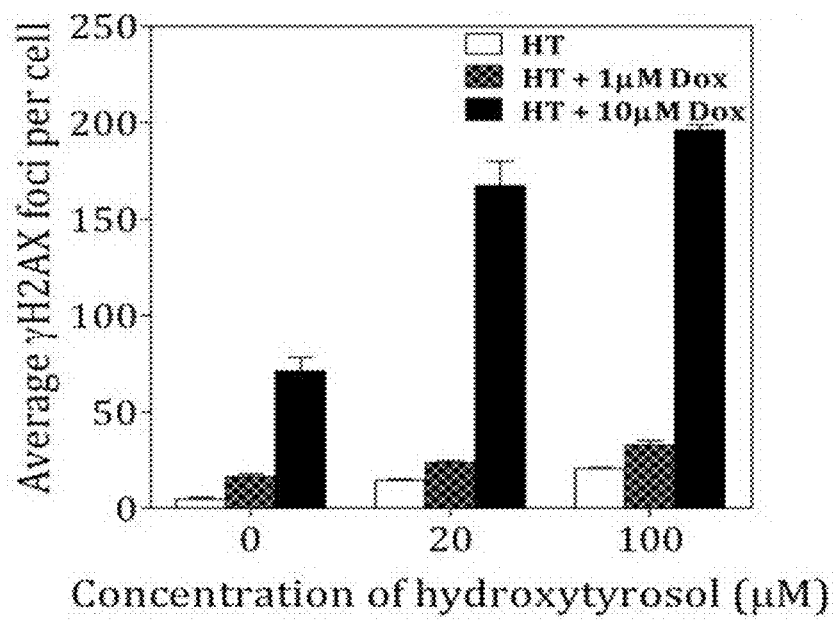
FIG. 5 (A-B) shows double-stranded DNA breaks in cancer cells induced by doxorubicin in the presence of hydroxytyrosol according to an exemplary embodiment of the invention. (A) shows a quantification of double-stranded DNA breaks in cancer cells induced by doxorubicin in the presence of hydroxytyrosol according to an exemplary embodiment of the invention. (B) shows a quantification of double-stranded DNA breaks in PBMC following exposure to doxorubicin in the presence of hydroxytyrosol according to an exemplary embodiment of the invention; total of 2 independent experiments tested.
Figure 5B:
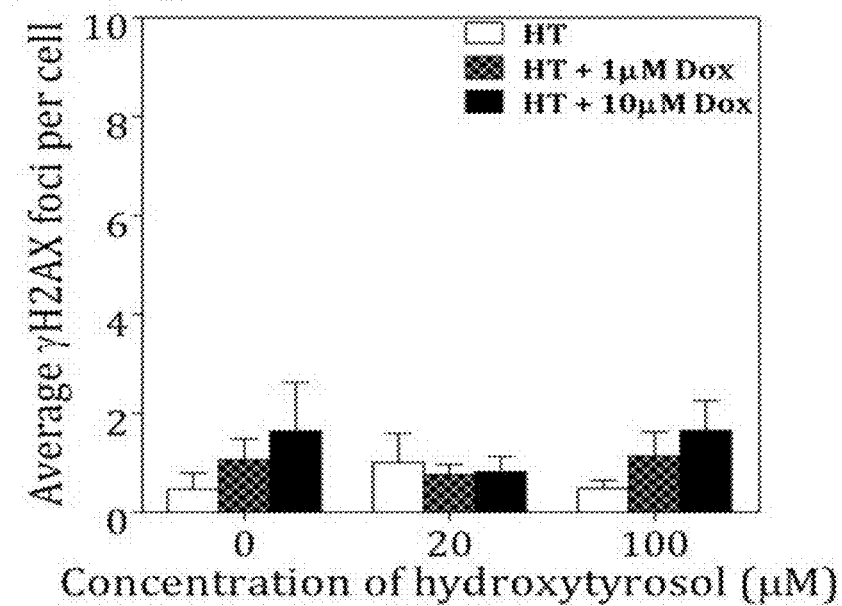

Hydroxytyrosol enhances the cytotoxicity of doxorubicin in K562 cells. The anthracycline doxorubicin is widely used in cancer therapy as a front line chemotherapeutic. Findings indicate that pre-treatment of K562 cells with hydroxytyrosol enhances the DNA damaging and cytotoxic effects of doxorubicin by inducing caspase 3/7 apoptosis (FIG. 4) and DNA double strand breaks (FIG. 5). Importantly, this effect was evident preferentially in the malignant K562 cells compared to the PBMC cells.

Figure 6A:
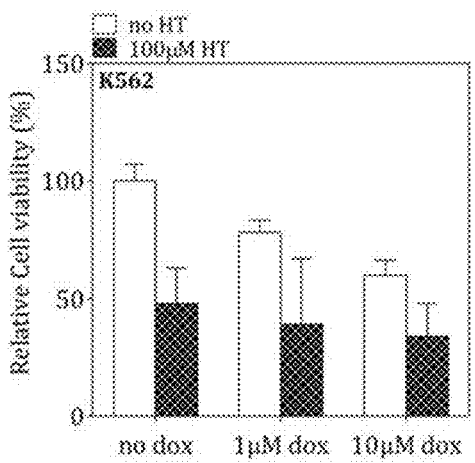
FIG. 6 (A-C) shows that hydroxytyrosol enhances the cytotoxic, apoptotic and DNA damaging effects of the chemotherapeutic agent doxorubicin. (A-B) The combination of hydroxytyrosol and chemotherapy induces synergistic cytotoxic effects and apoptosis measured by (A) the Cell-Titer Blue assay kit and (B) Apo-ONE homogenous caspase 3/7 assay kit respectively. (C) Further, hydroxytyrosol enhances DNA damage induced by doxorubicin in erythroleukemic K562 cells in a dose-dependent manner. K562 cells were pre-treated with 100 $\mu$M hydroxytyrosol (HT) for 24 hours and 1 hour incubation with 1 $\mu$M or 10 $\mu$M doxorubicin. Cells were then stained for $\gamma$H2AX (green), a molecular marker of DNA double strand breaks. Mean±standard deviations from a single experiment performed in duplicate are shown; total of 2 independent experiments tested. The level of significance was accepted at $p<0.01$ and **$p<0.0001$.
Figure 6B:
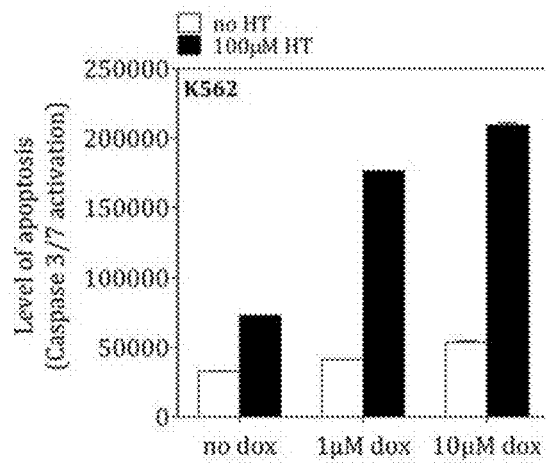
Figure 6C:
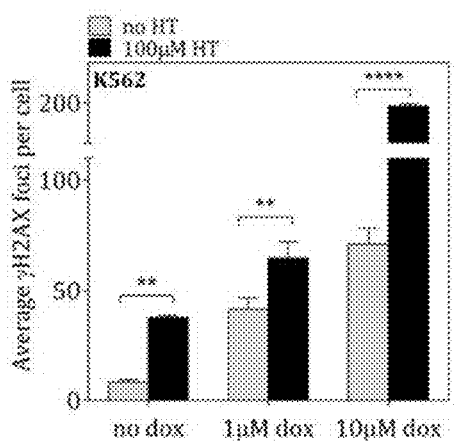
Figure 7A:
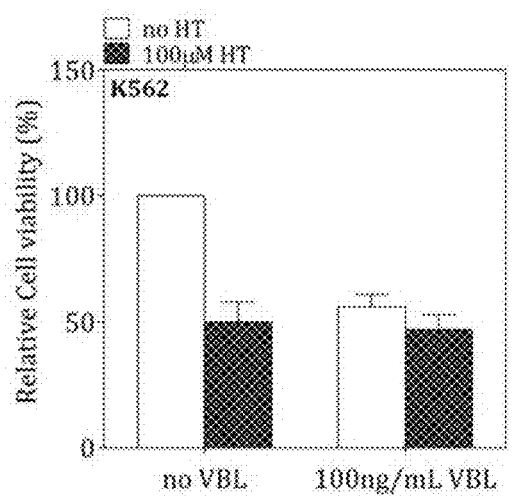
FIG. 7 (A-C) shows hydroxytyrosol enhances the DNA damaging effects of the chemotherapeutic agent vinblastin (VBL). (A-B) The combination of hydroxytyrosol and chemotherapy increases the cytotoxic effects and apoptosis measured by (A) the Cell-Titer Blue assay kit and (B) Apo-ONE homogenous caspase 3/7 assay kit respectively. (C) Further, hydroxytyrosol enhances DNA damage induced by vinblastin in erythroleukemic K562 cells. K562 cells were pre-treated with 100 $\mu$M hydroxytyrosol (HT) for 24 hours prior to a 2 hour incubation with 100 ng/mL vinblastin. Cells were then stained for $\gamma$H2AX (green), a molecular marker of DNA double strand breaks. Mean±standard deviations from a single experiment performed in duplicate are shown; level of significance was accepted at **$p<0.01$.
Figure 7B:
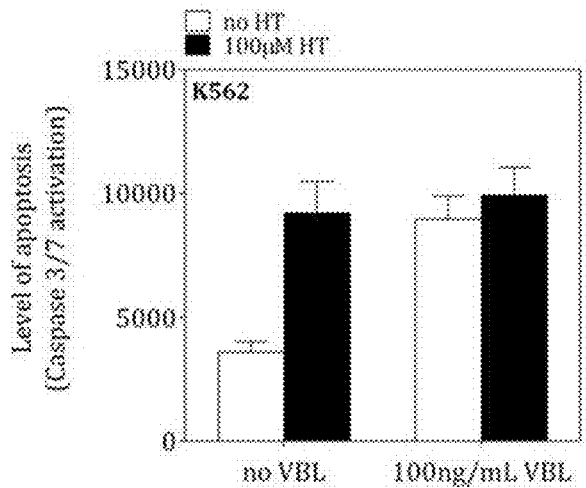
Figure 7C:
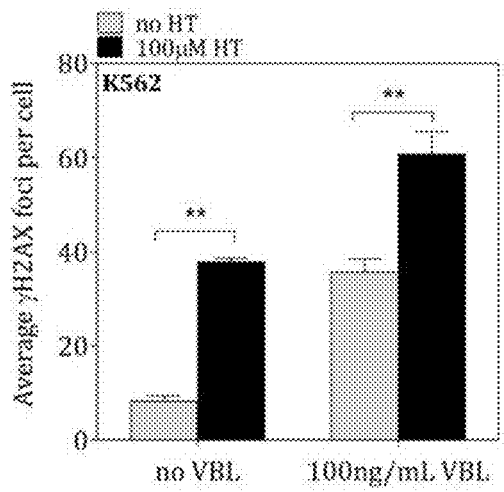
Figure 8A:
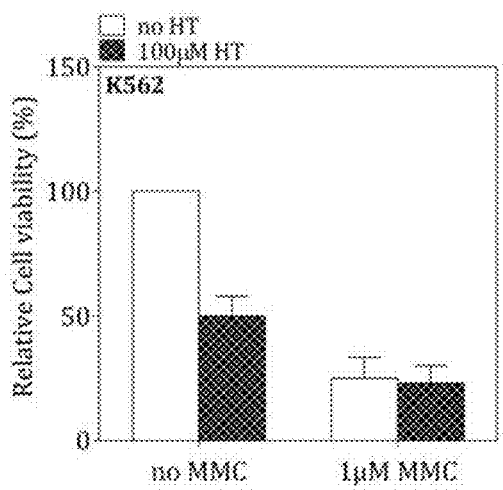
FIG. 8 (A-C) shows hydroxytyrosol enhances the apoptotic and DNA damaging effects of the chemotherapeutic agent mitomycin C (MMC). (A-B) The combination of hydroxytyrosol and chemotherapy induces synergistic apoptosis measured by (A) the Cell-Titer Blue assay kit and (B) Apo-ONE homogenous caspase 3/7 assay kit respectively. (C) Further, hydroxytyrosol enhances DNA damage induced by mitomycin C in erythroleukemic K562. K562 cells were pre-treated with 100 μM hydroxytyrosol (HT) for 24 hours prior to a 2 hour incubation with 1 μM mitomycin C. Cells were then stained for γH2AX (green), a molecular marker of DNA double strand breaks. Mean±standard deviations from a single experiment performed in duplicate are shown; level of significance was accepted at **$p<0.01$.
Figure 8B:
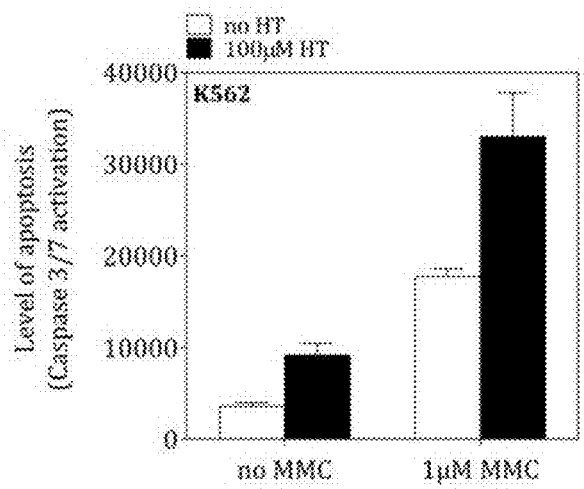
Figure 8C:
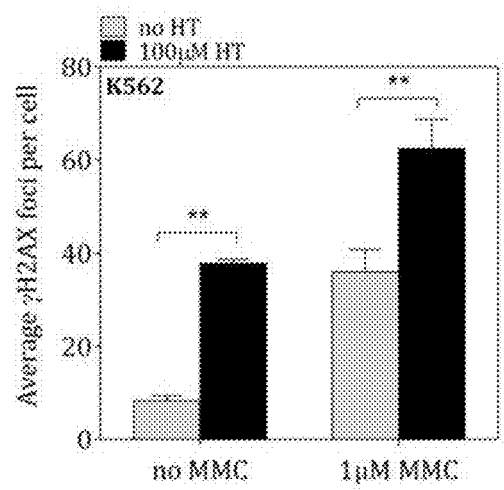
Figure 10:
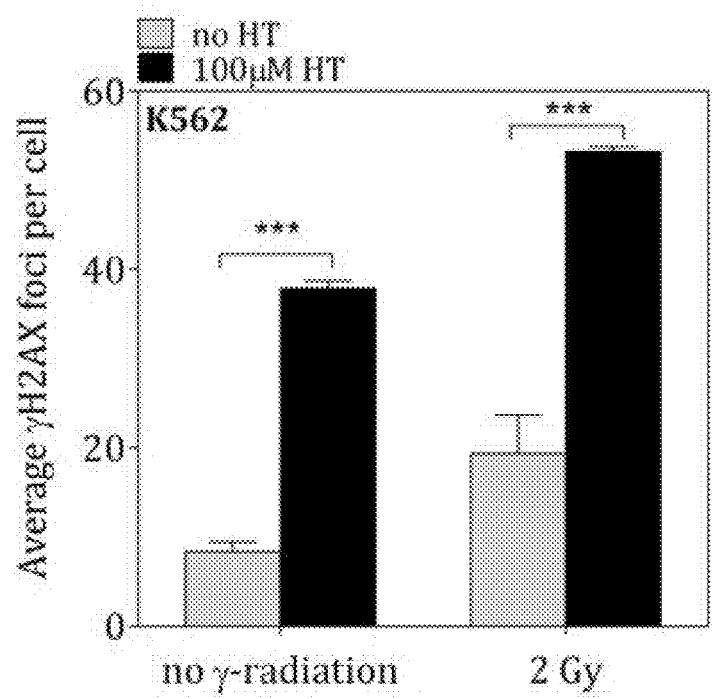
FIG. 10 shows Hydroxytyrosol enhances DNA damage induced by γ-radiation in erythroleukemic K562 cells. K562 cells pre-treated with 100 μM hydroxytyrosol (HT) for 24 hours prior to 1 hour incubation following exposure to 2 Gy (137Cs). Cells were then stained for γH2AX (green), a molecular marker of DNA double strand breaks. Mean±standard deviations from a single experiment performed in duplicate are shown; level of significance was accepted at ***$p<0.001$.

The results further show hydroxytyrosol enhances the DNA damaging effects of all anti-cancer modalities tested in the erythroleukemic K562 malignant cell model. The efficacy of hydroxytyrosol used in conjunction with the anthracycline doxorubicin (FIG. 6)—widely used in cancer therapy as a front line chemotherapeutic; anti-cancer agents vinblastine (FIG. 7) and mitomycin C (FIG. 8) and the radiation modalities UVA (FIG. 9) and ionizing γ-radiation (FIG. 10) was investigated. The results indicate that pre-treatment of K562 cells with hydroxytyrosol enhances the cytotoxic effects of most anti-cancer modalities also via the induction of caspase 3/7 apoptosis and DNA double strand breaks. These findings suggest the potential for combinatorial effects of hydroxytyrosol with current conventional cancer therapies.

According to embodiments of the invention, the use of HT-containing compositions in conjunction with chemotherapeutic agents, e.g. doxorubicin, demonstrate benefits for the combined use of hydroxytyrosol and doxorubicin in cancer therapy.

Example 4

Figure 11A:
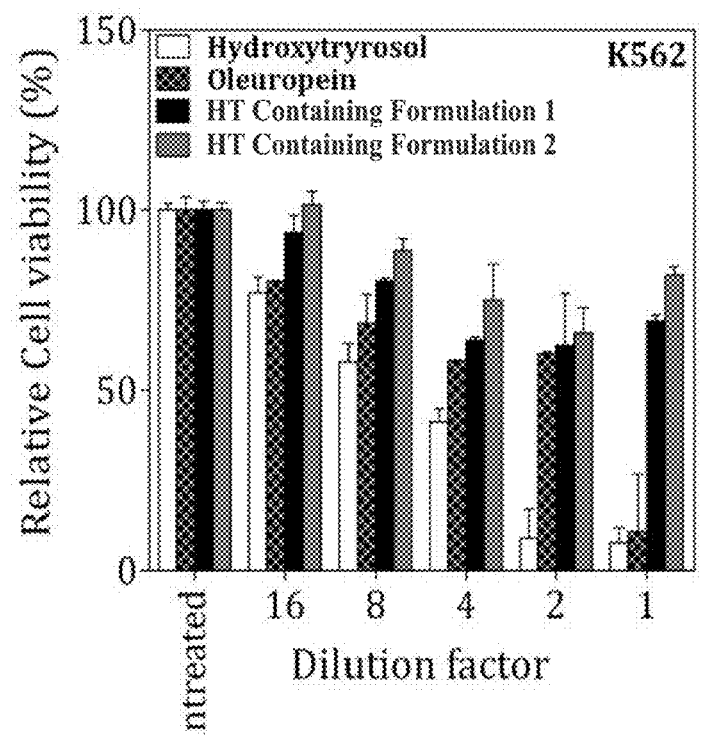
FIG. 11 (A-B) shows a decrease in K562 cell viability (A) and an increase in PBMC cell viability (B) induced by hydroxytyrosol according to an exemplary embodiment of the invention. (For Formulations (1, 2 and 3), see Table 9). Mean±standard deviations from a single experiment performed in triplicate are shown; total of 2 independent experiments tested.
Figure 11B:
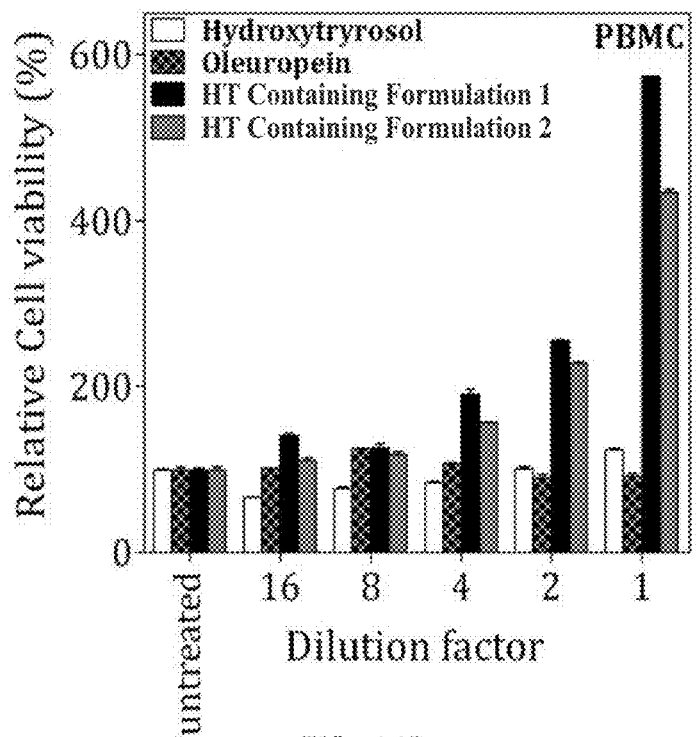
Figure 12A:
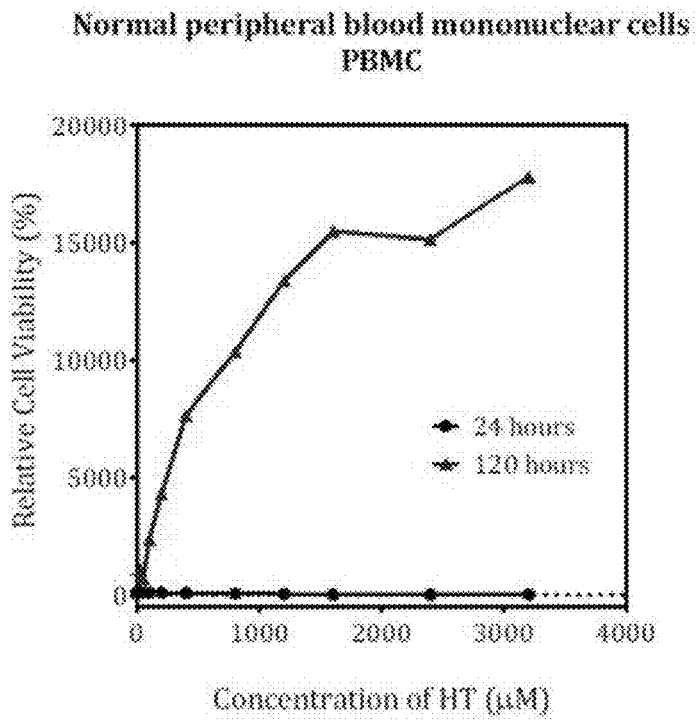
FIG. 12 (A-I) shows induction of cell-death and apoptosis by hydroxytyrosol preferentially in malignant cells compared to normal cells. Hydroxytyrosol (HT) decreases cell proliferation in haematological malignancies. (A) HT increases the proliferation of normal peripheral blood mononuclear cells (PBMCs) following 120 hours incubation. HT reduces the cell proliferation of human haematological malignancies in a dose and time-dependent manner (B-I) but does not affect PBMCs (A) following 24 hours of incubation with HT. (B) Chronic myeloid leukemia K562 cells; (C) acute myeloid leukemia (AML) HL-60 cells; (D) cutaneous T cell lymphoma (CTCL) MyLa CD4+ cells; (E) cutaneous T cell lymphoma (CTCL) MyLa CD8+ cells; (F) large B-lymphocyte non-Hodgkin's lymphoma LCL-25 cells; (G) acute T lymphoblast leukemia (ALL) CEM CCRF cells; (H) MDR acute T lymphoblast leukemia (MDR ALL) R100 cells; (I) leukemic monocyte lymphoma U937 cells. Mean±standard deviations from a three independent experiments performed in duplicate are shown.
Figure 12B:
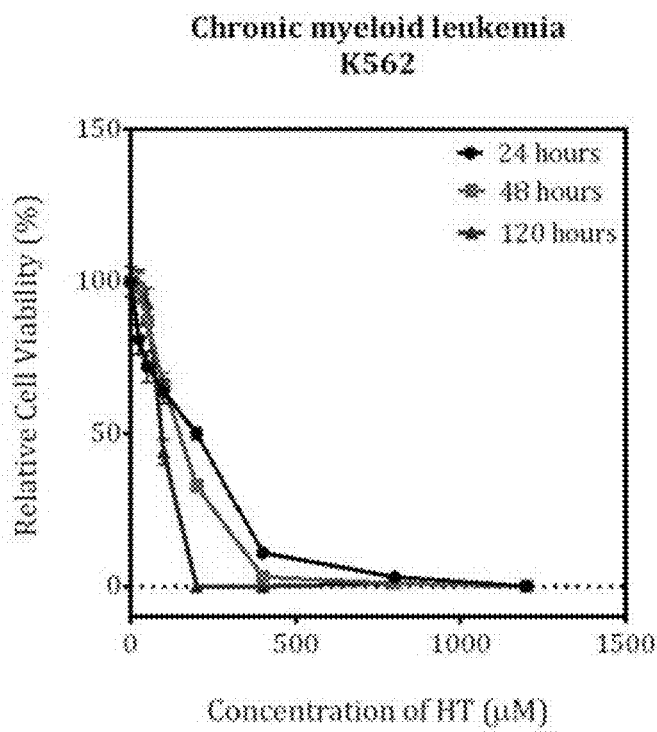
Figure 12C:
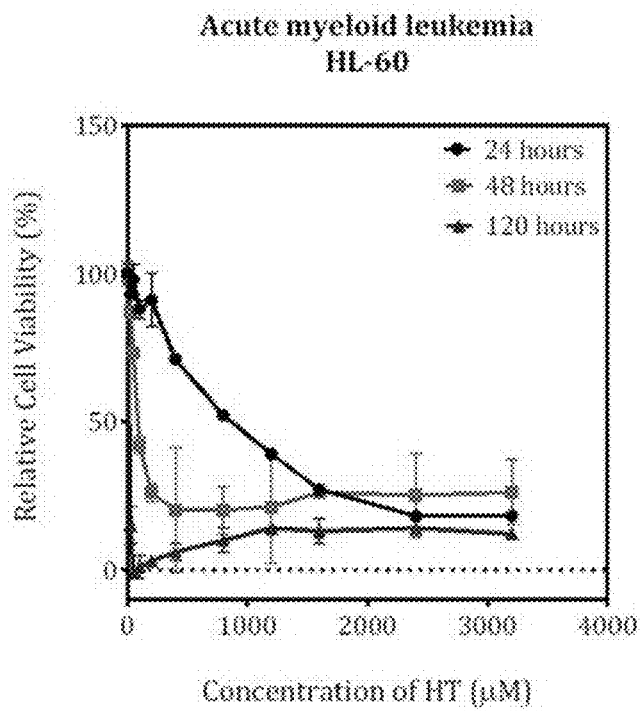
Figure 12D:
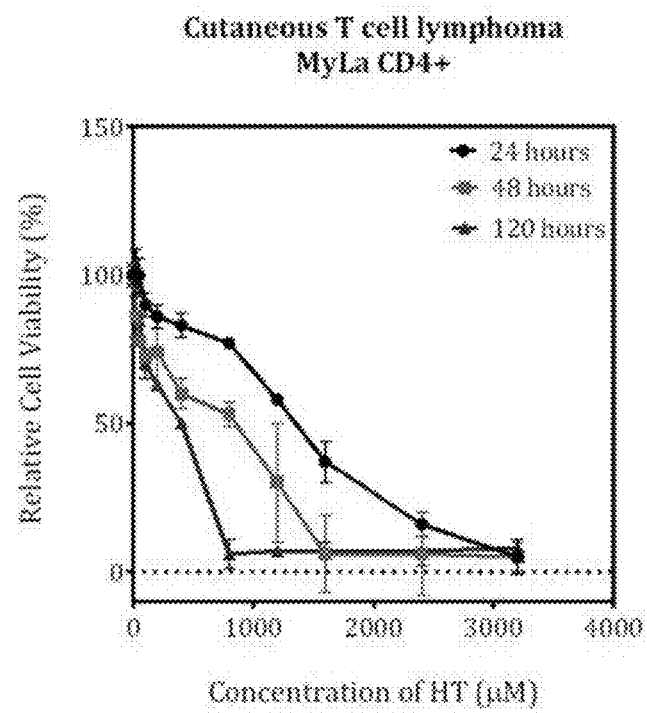
Figure 12E:
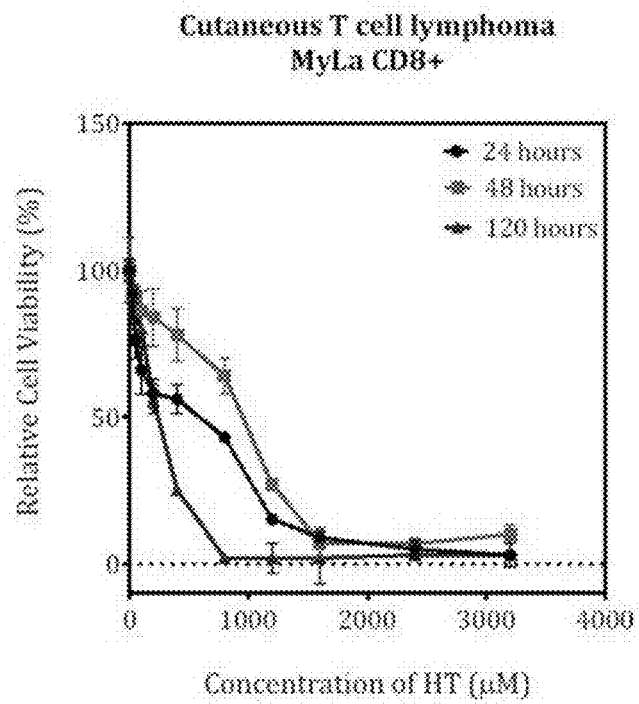
Figure 12F:
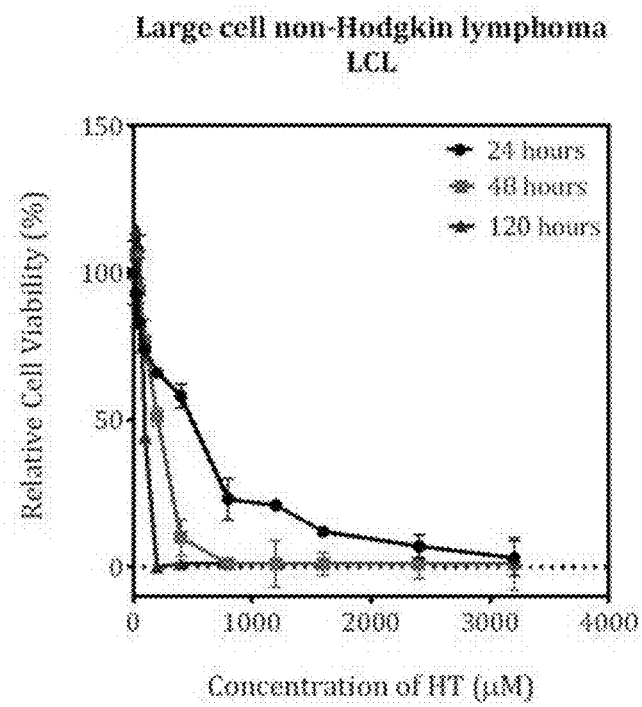
Figure 12G:
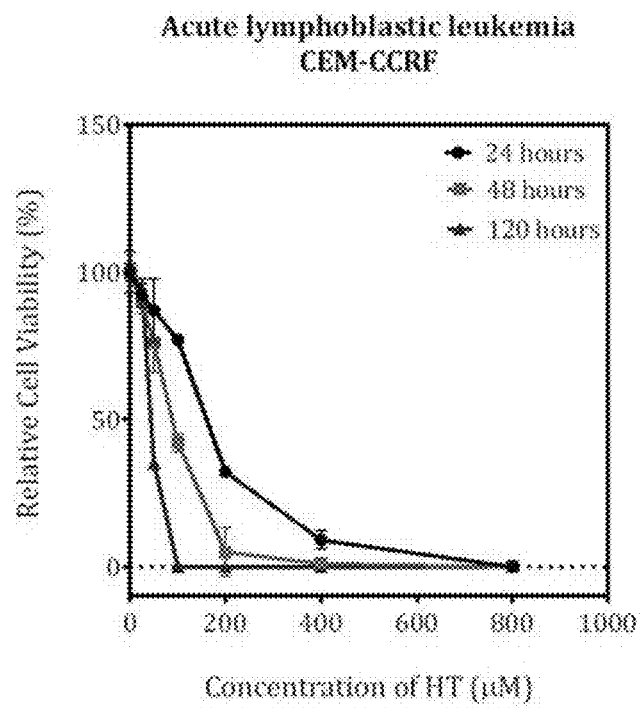
Figure 12H:
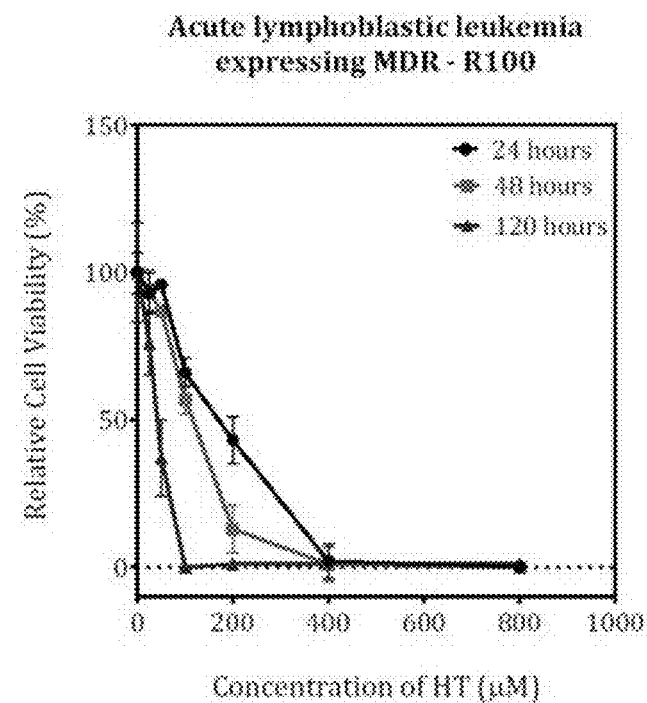
Figure 12I:
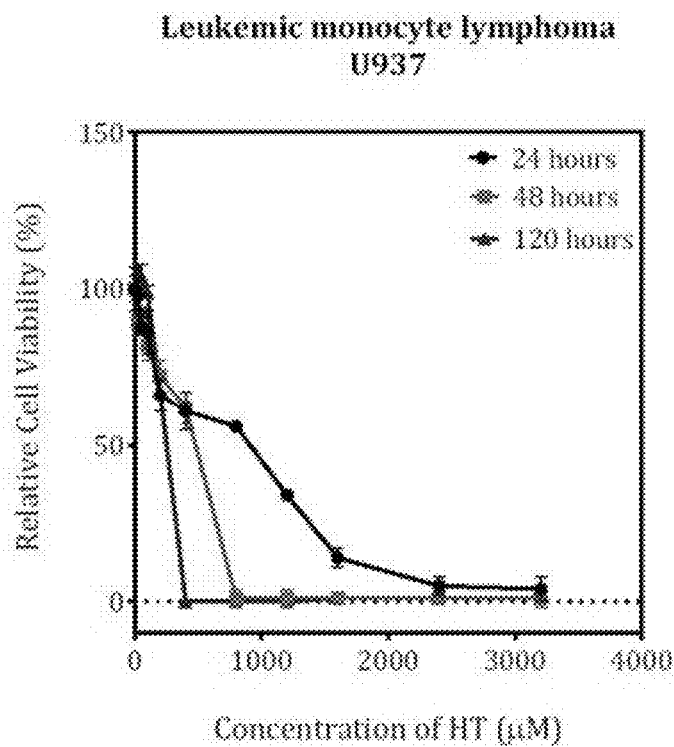
Figure 13A:
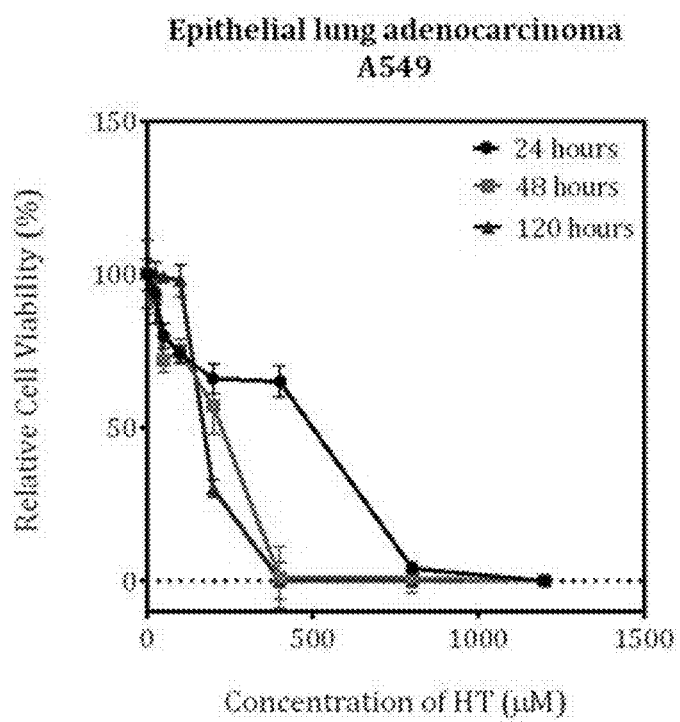
FIG. 13 (A-H) shows induction of cell-death and apoptosis by hydroxytyrosol preferentially in malignant cells compared to normal cells. Hydroxytyrosol (HT) decreases cell proliferation in non-haematological malignancies. HT reduces the cell proliferation of numerous human malignancies in a dose and time-dependent manner: (A) epithelial lung adenocarcinoma A549 cells; (B) liver hepatocellular carcinoma Hep G2 cells; (C) colorectal carcinoma HT-29 cells; (D) breast adenocarcinoma MCF7 cells; (E) prostate adenocarcinoma PC3 cells; (F) brain glioblastoma T98G cells; (G) gastric carcinoma SNU-16; (H) epidermal squamous carcinoma A431 cells. Mean±standard deviations from a three independent experiments performed in duplicate are shown.
Figure 13B:
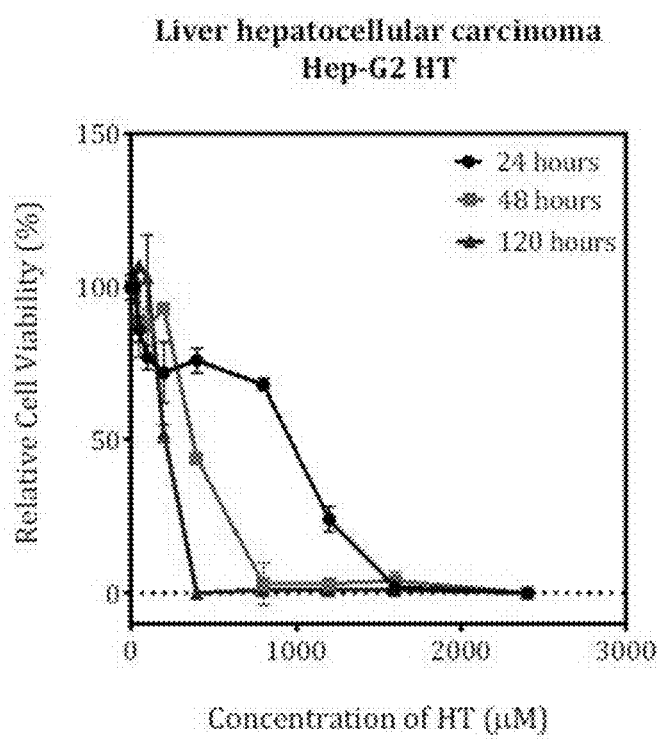
Figure 13C:
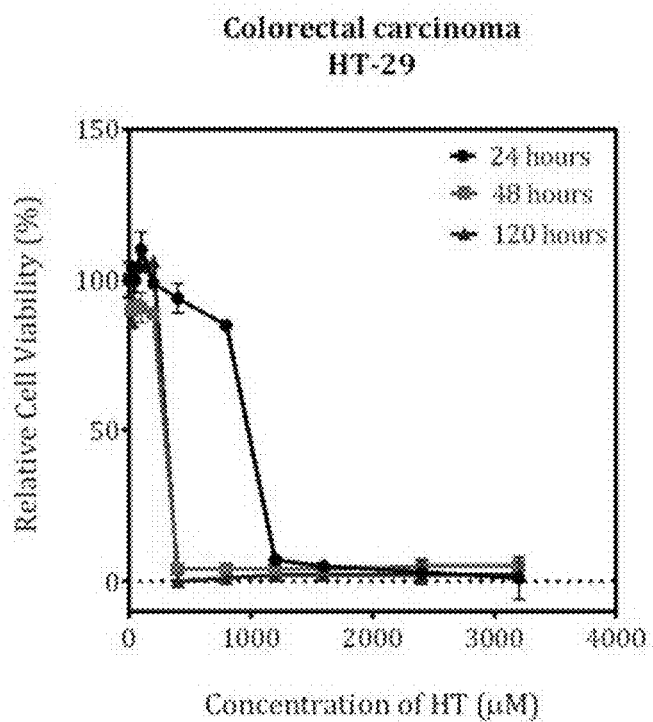
Figure 13D:
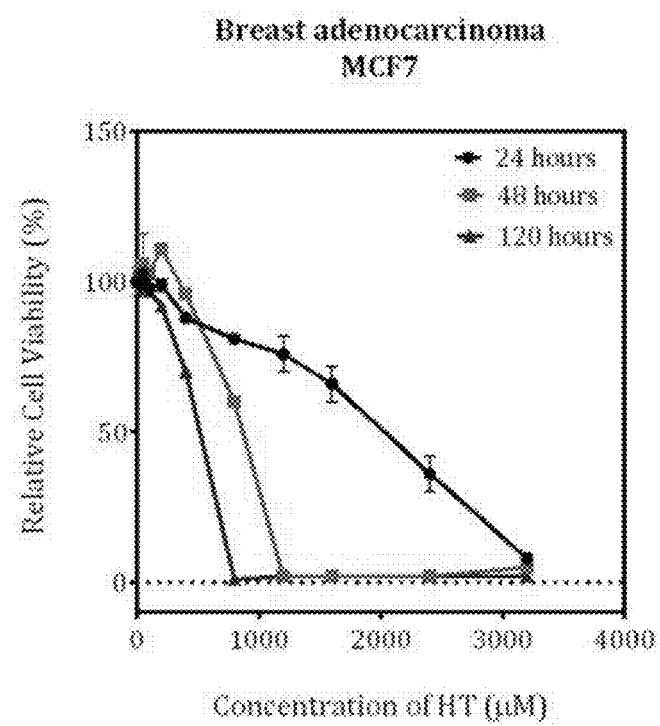
Figure 13E:
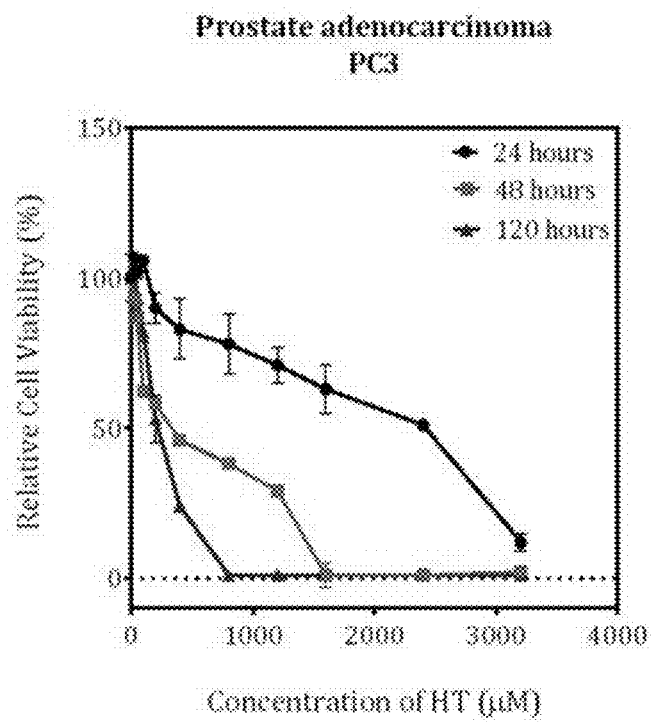
Figure 13F:
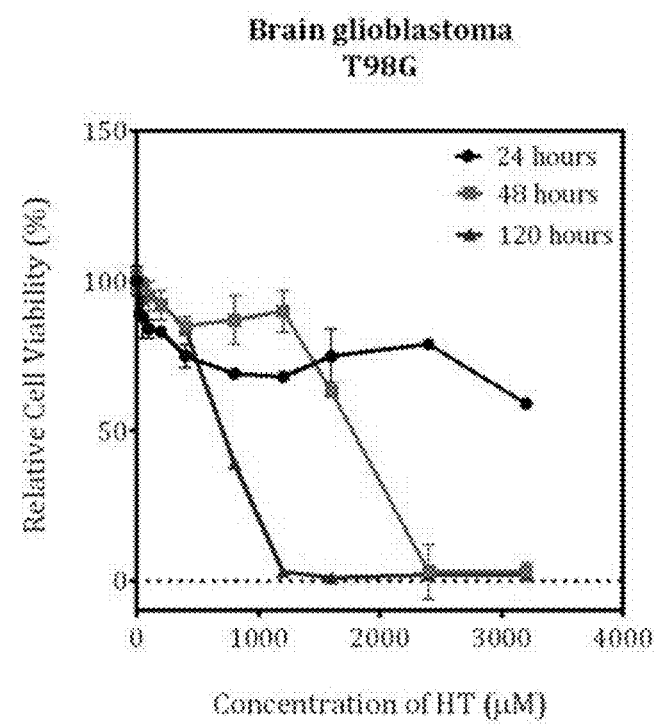
Figure 13G:
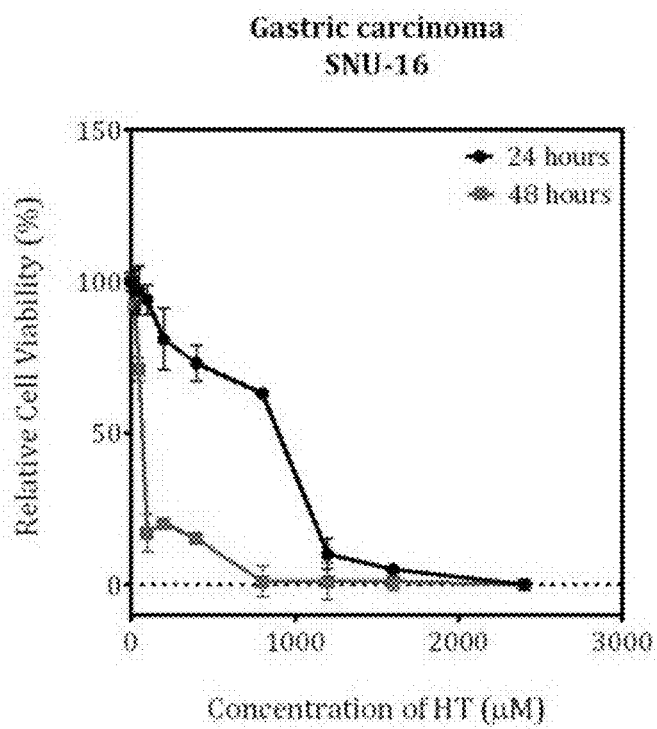
Figure 13H:
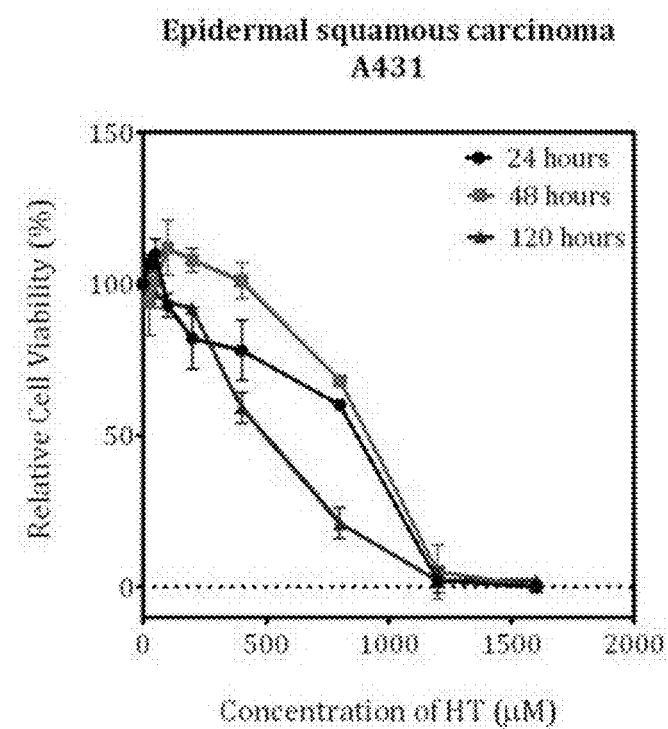
Figure 14A:
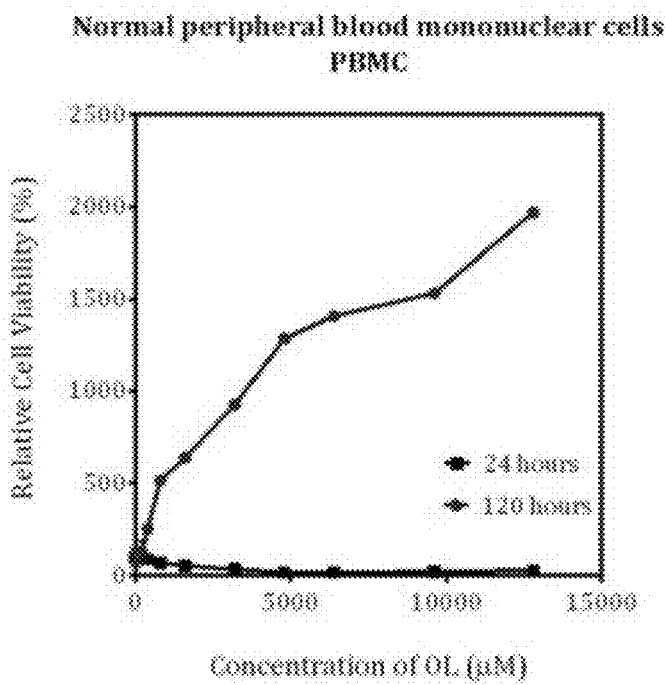
FIG. 14 (A-I) shows induction of cell-death and apoptosis by hydroxytyrosol preferentially in malignant cells compared to normal cells. An exemplary embodiment of the invention, Oleuropein (OL), decreases cell proliferation in haematological malignancies. (A) OL increases the proliferation of normal peripheral blood mononuclear cells (PBMCs) following 120 hours incubation. OL reduces the cell proliferation of human haematological malignancies (B-I) in a dose and time-dependent manner but does not affect PBMC (A) following 24 hours of incubation with OL. (B) Chronic myeloid leukemia K562 cells; (C) acute myeloid leukemia (AML) HL-60 cells; (D) cutaneous T cell lymphoma (CTCL) MyLa CD4+ cells; (E) cutaneous T cell lymphoma (CTCL) MyLa CD8+ cells; (F) large B-lymphocyte non-Hodgkin's lymphoma LCL-25 cells; (G) acute T lymphoblast leukemia (ALL) CEM CCRF cells; (H) MDR acute T lymphoblast leukemia (MDR ALL) R100 cells; (I) leukemic monocyte lymphoma U937 cells. Mean±Standard deviations from a three independent experiments performed in duplicate are shown.
Figure 14B:
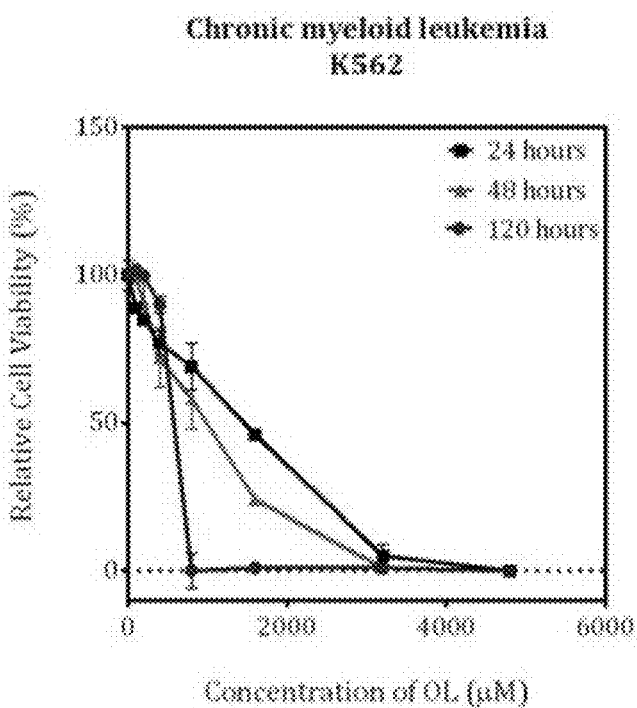
Figure 14C:
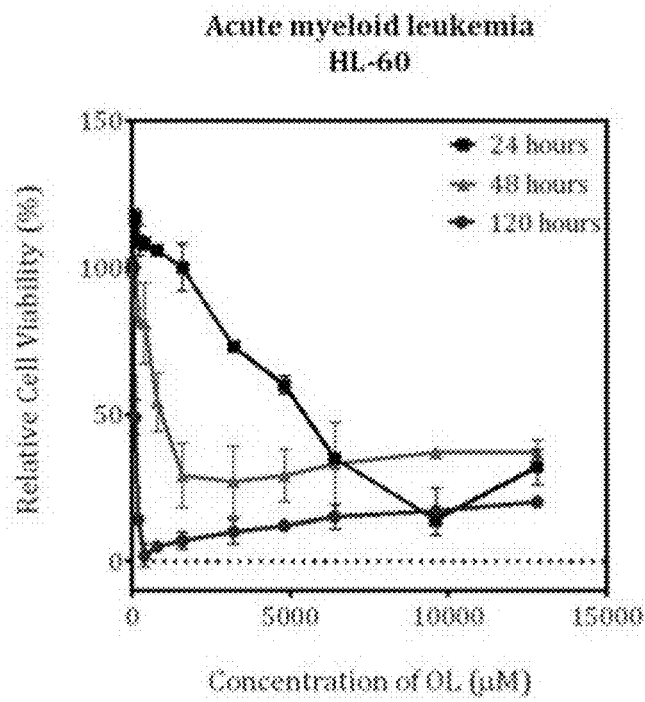
Figure 14D:
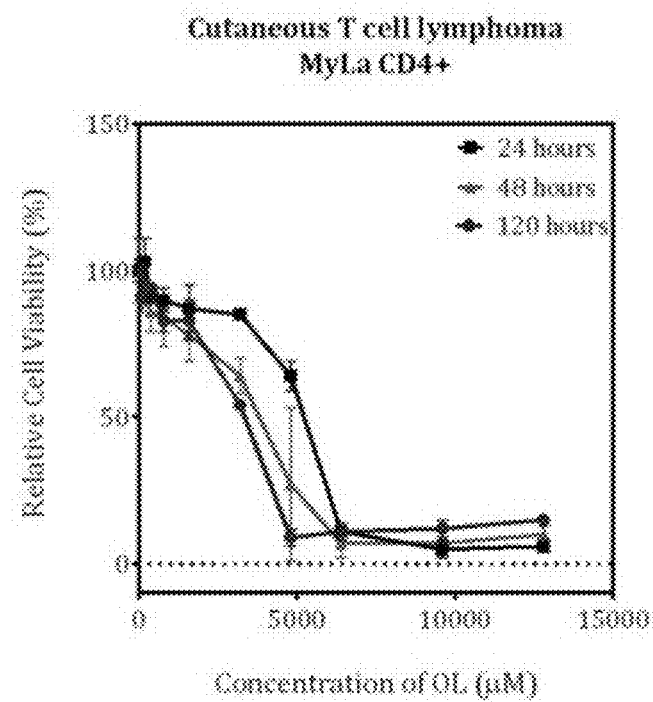
Figure 14E:
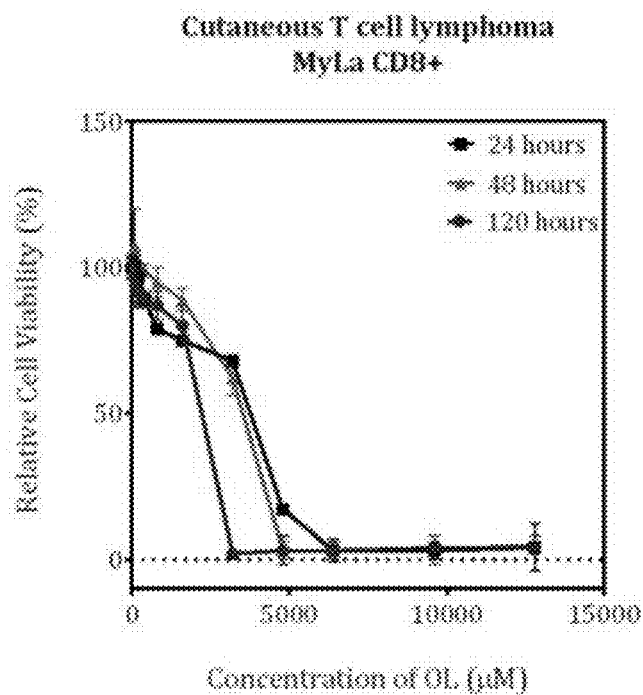
Figure 14F:
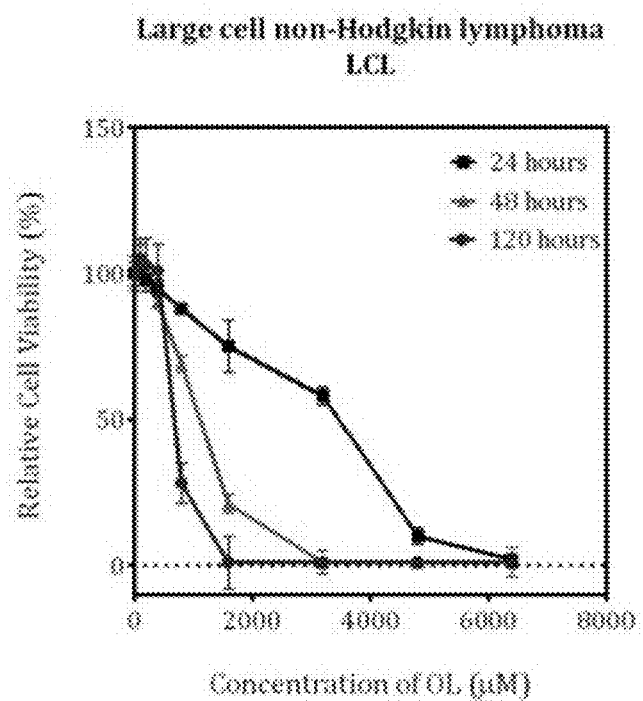
Figure 14G:
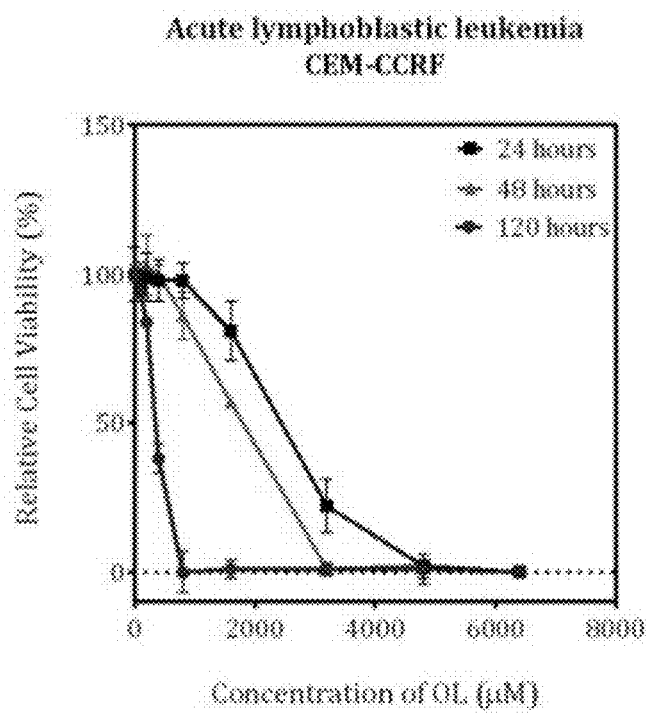
Figure 14H:
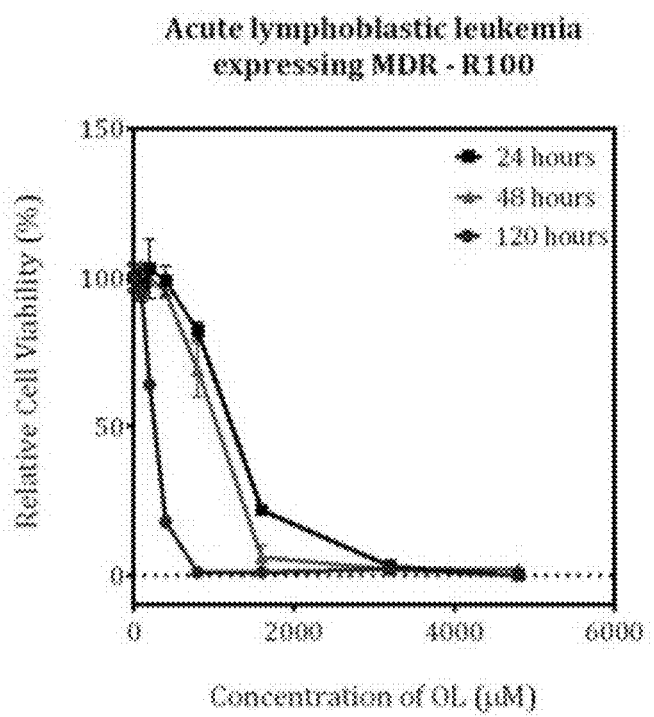
Figure 14I:
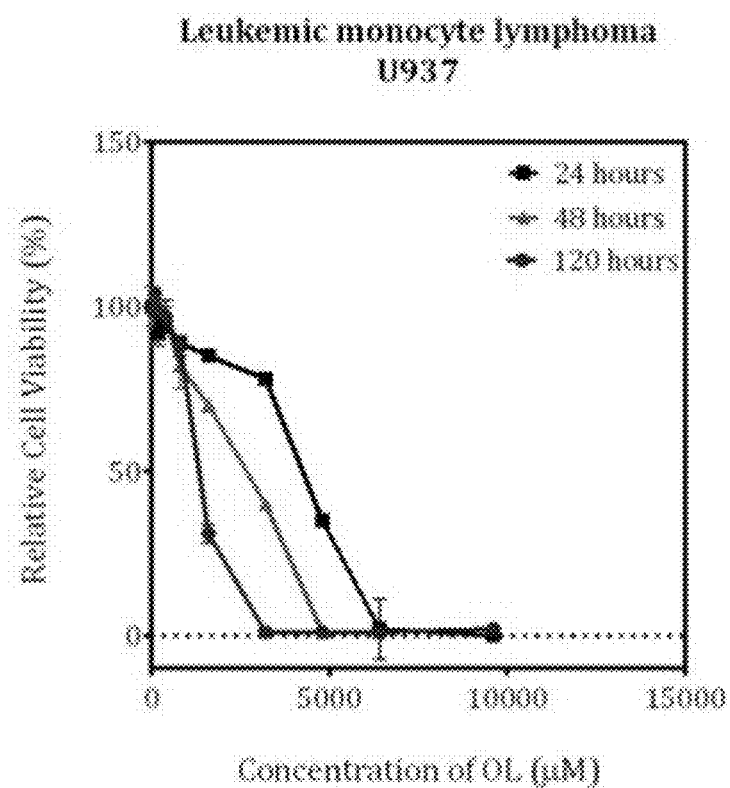
Figure 15A:
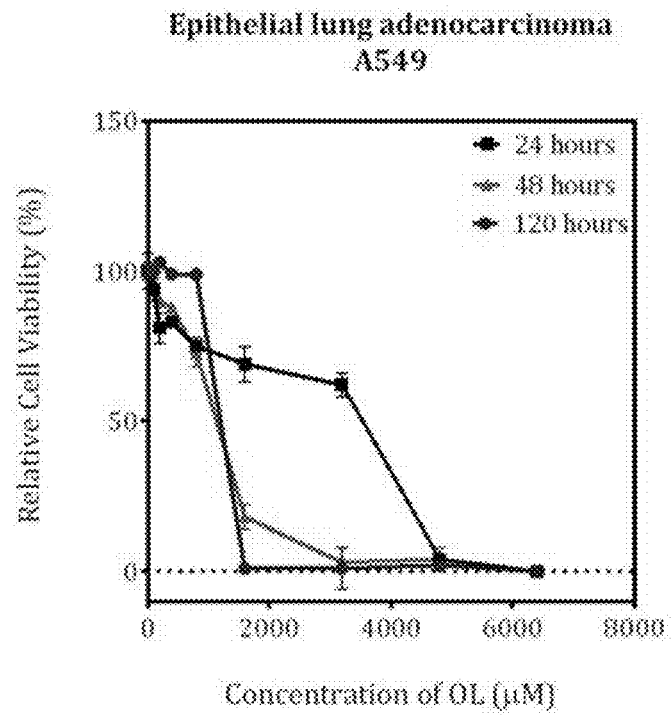
FIG. 15 (A-H) shows induction of cell-death and apoptosis by hydroxytyrosol preferentially in malignant cells compared to normal cells. An exemplary embodiment of the invention, Oleuropein (OL), decreases cell proliferation in non-haematological malignancies. OL reduces the cell proliferation of numerous human malignancies in a dose and time-dependent manner: (A) epithelial lung adenocarcinoma A549 cells; (B) liver hepatocellular carcinoma Hep G2 cells; (C) colorectal carcinoma HT-29 cells; (D) breast adenocarcinoma MCF7 cells; (E) prostate adenocarcinoma PC3 cells; (F) brain glioblastoma T98G cells; (G) gastric carcinoma SNU-16; (H) epidermal squamous carcinoma A431 cells. Mean±standard deviations from a three independent experiments performed in duplicate are shown.
Figure 15B:
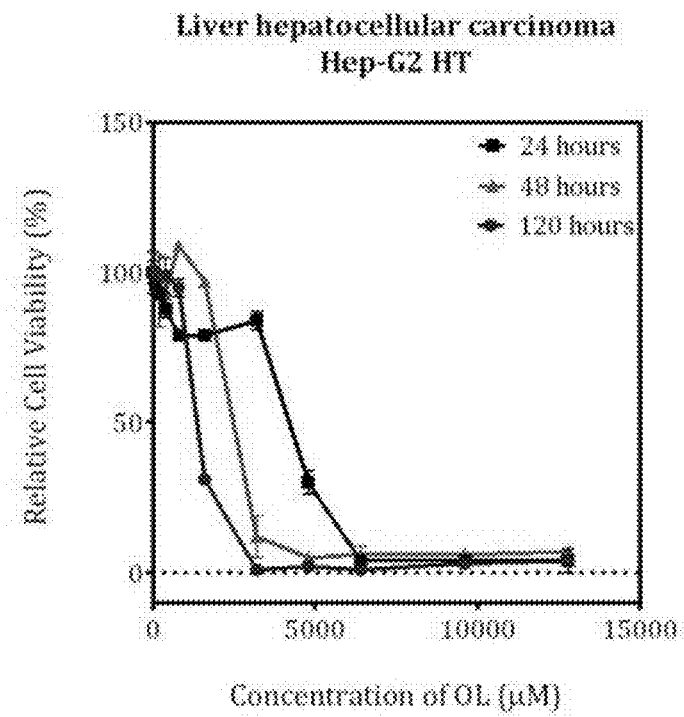
Figure 15C:
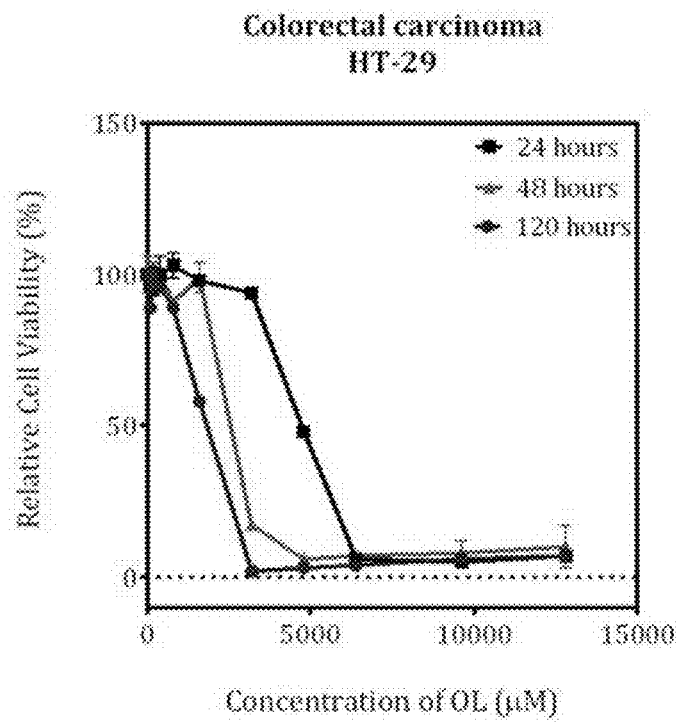
Figure 15D:
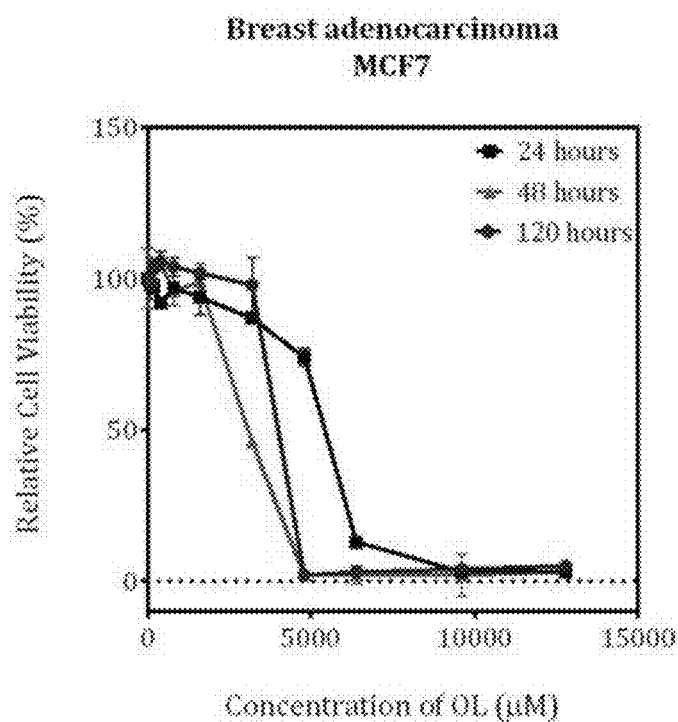
Figure 15E:
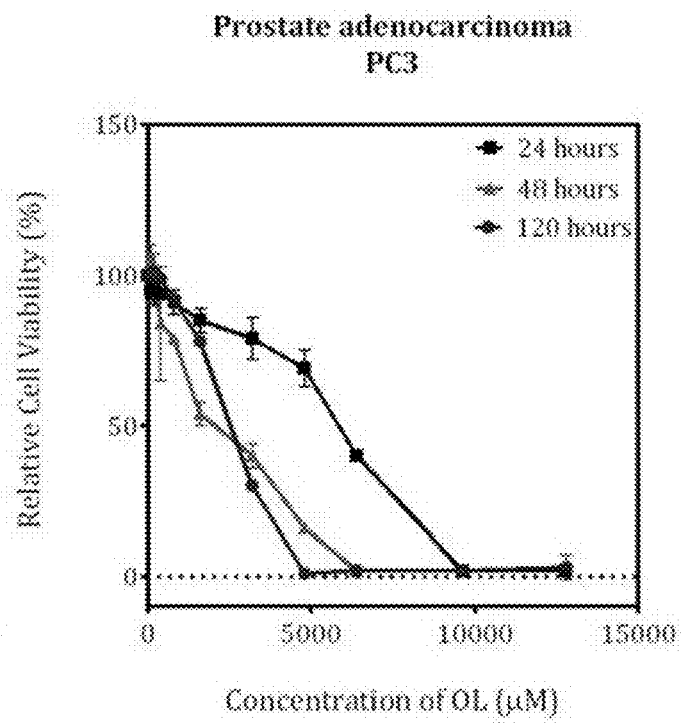
Figure 15F:
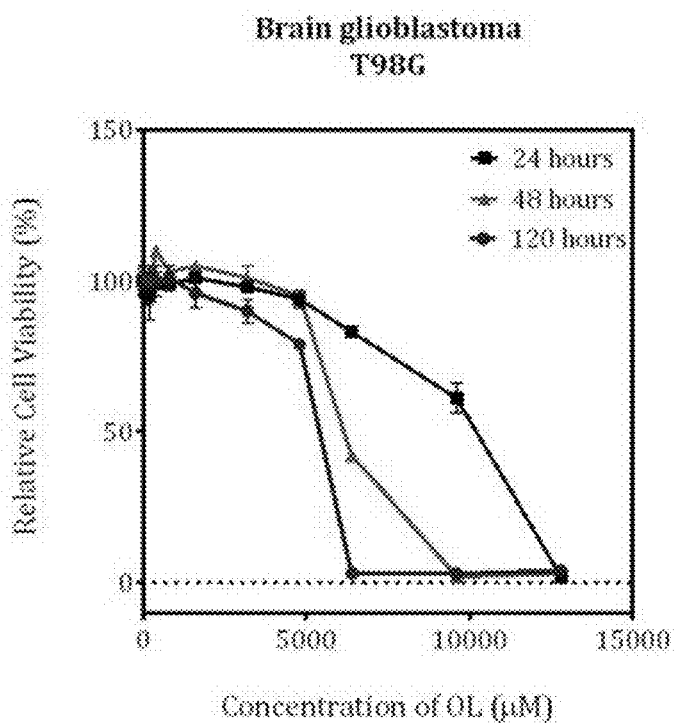
Figure 15G:
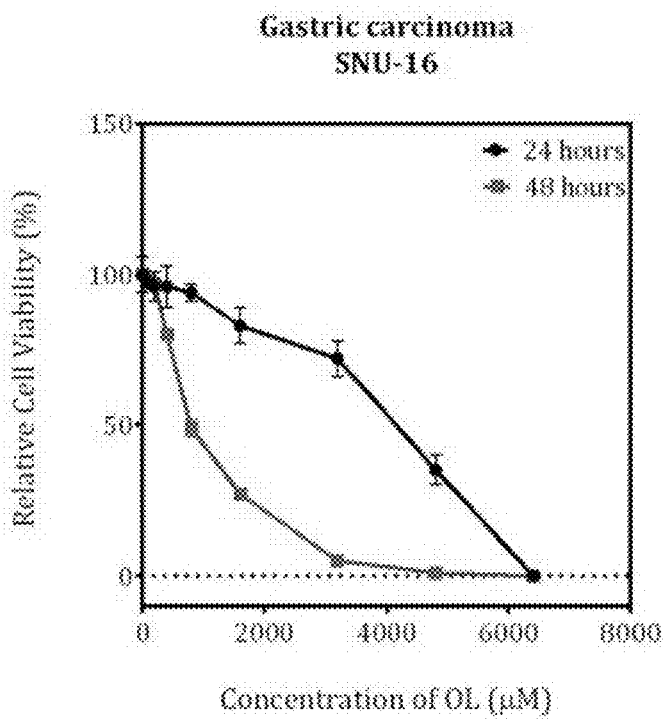
Figure 15H:
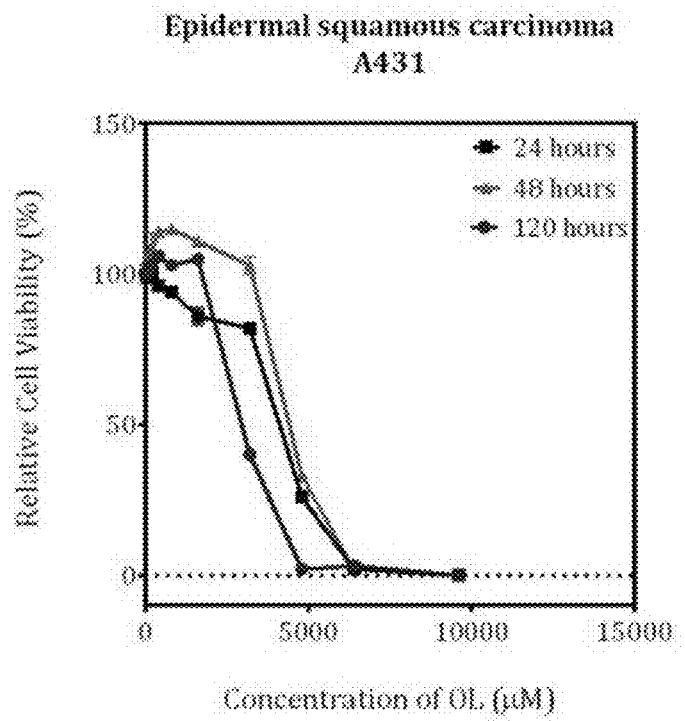
Figure 16A:
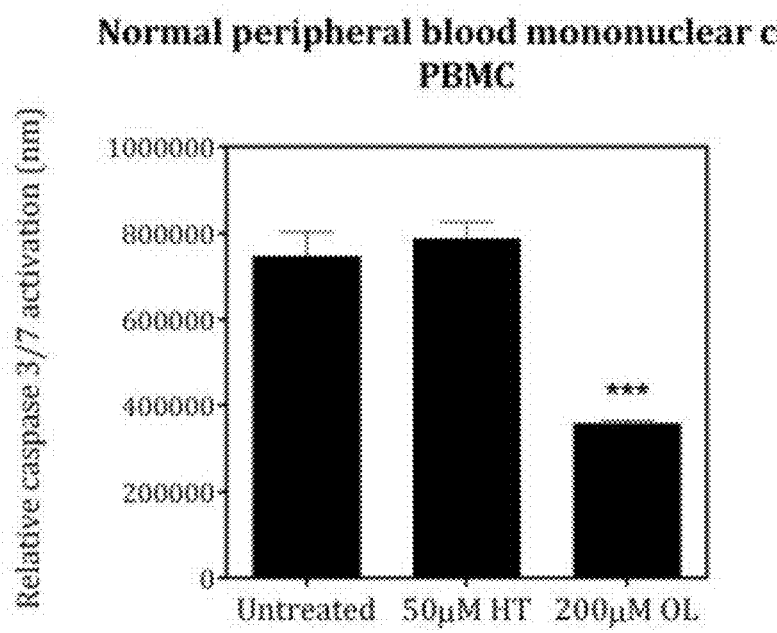
FIG. 16 (A-H) shows induction of cell-death and apoptosis by hydroxytyrosol preferentially in malignant cells compared to normal cells. Hydroxytyrosol (HT) and oleuropein (OL) increase apoptosis via caspase 3/7 induction in haematological malignancies but not in normal blood cells. (A) OL significantly reduces apoptosis in normal peripheral blood mononuclear cells. (B-H) Either HT or OL or both olive constituents significantly increase caspase 3/7 apoptosis in the indicated human haematological malignant cells lines: (B) Chronic myeloid leukemia K562 cells; (C) cutaneous T cell lymphoma (CTCL) MyLa CD4+ cells; (D) cutaneous T cell lymphoma (CTCL) MyLa CD8+ cells; (E) acute T lymphoblast leukemia (ALL) CEM CCRF cells; (F) MDR acute T lymphoblast leukemia (MDR ALL) R100 cells; (G) large B-lymphocyte non-Hodgkin's lymphoma LCL-25 cells; (H) MDR acute T lymphoblast leukemia (MDR ALL) R100 cells; (I) leukemic monocyte lymphoma U937 cells. Mean±standard deviations from a single experiment performed in triplicate are shown; total of 2 independent experiments tested.
Figure 16B:
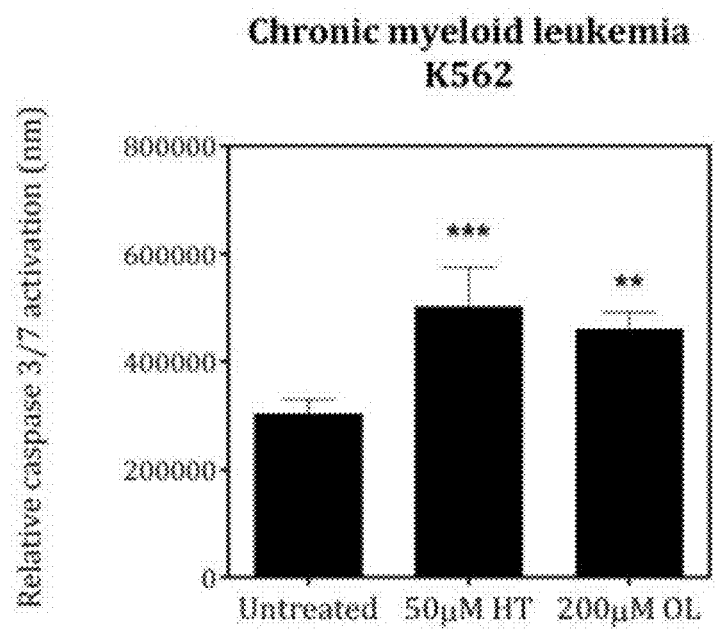
Figure 16C:
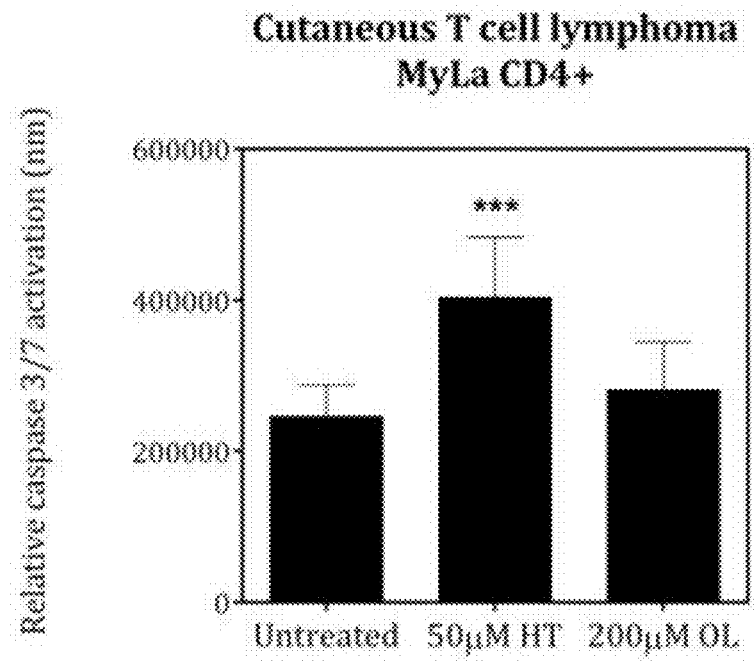
Figure 16D:
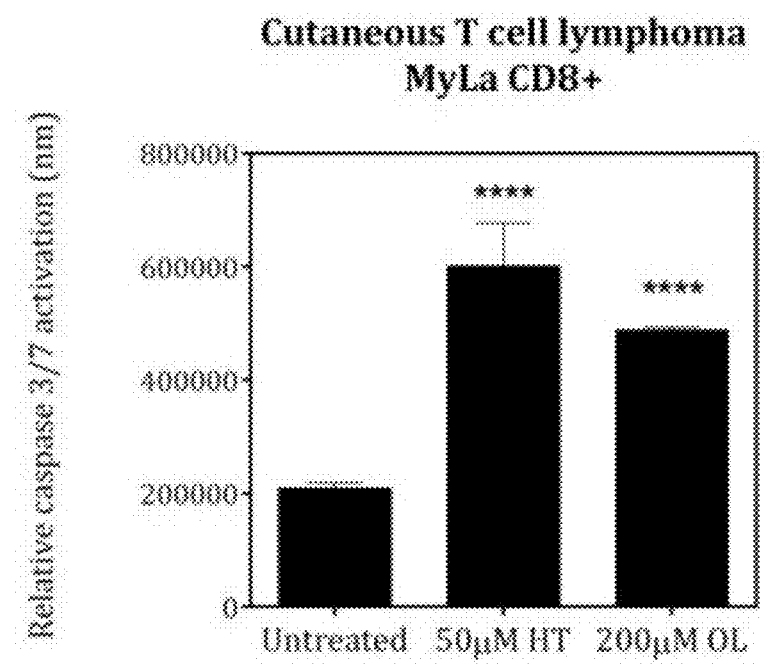
Figure 16E:
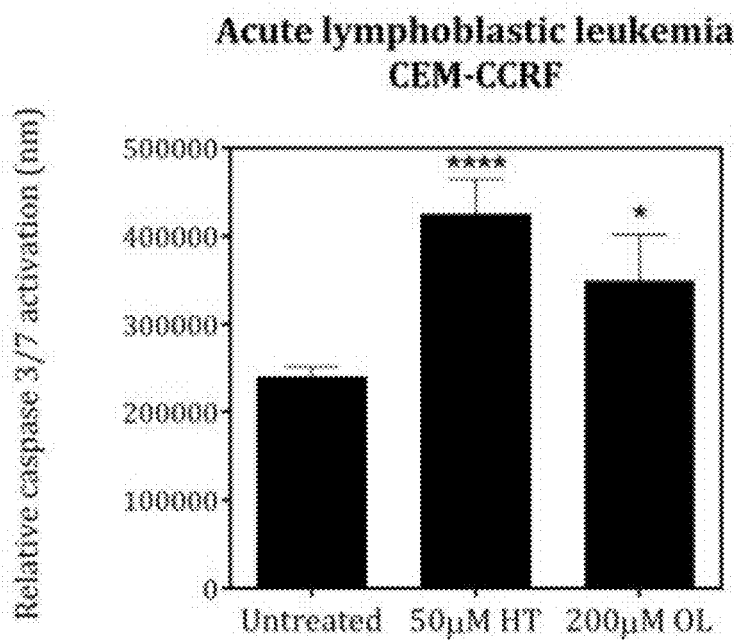
Figure 16F:
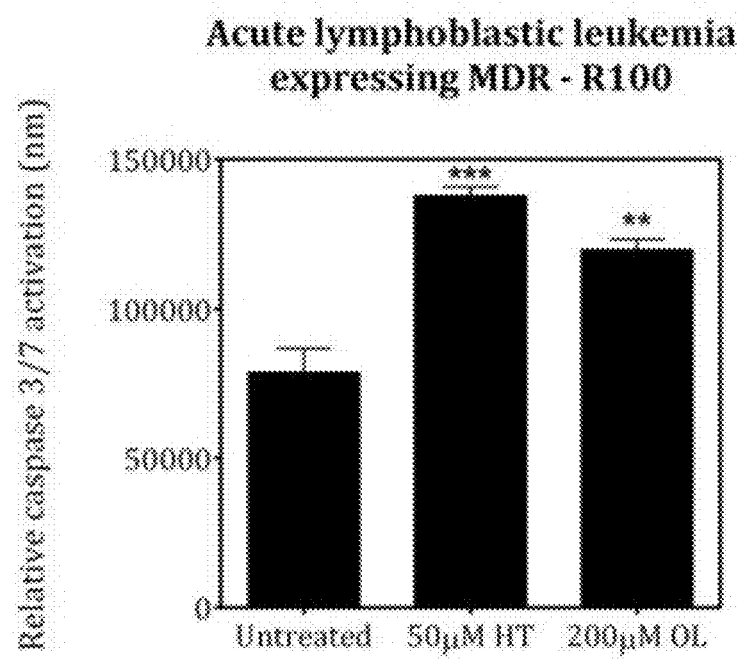
Figure 16G:
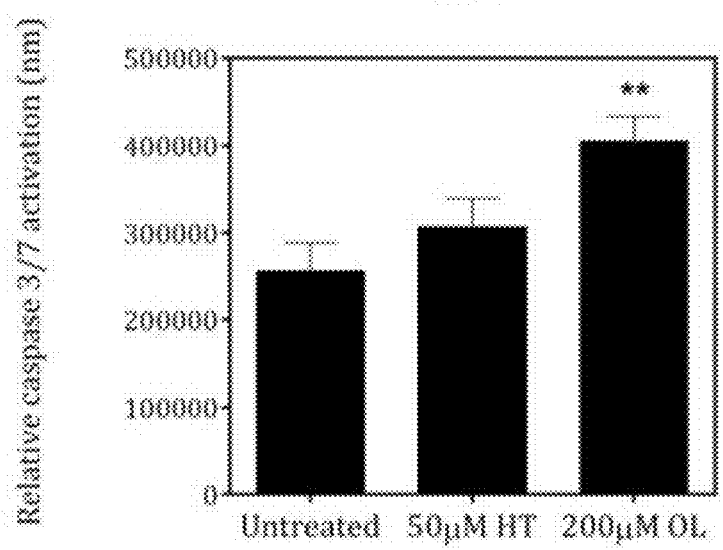
Figure 16H:
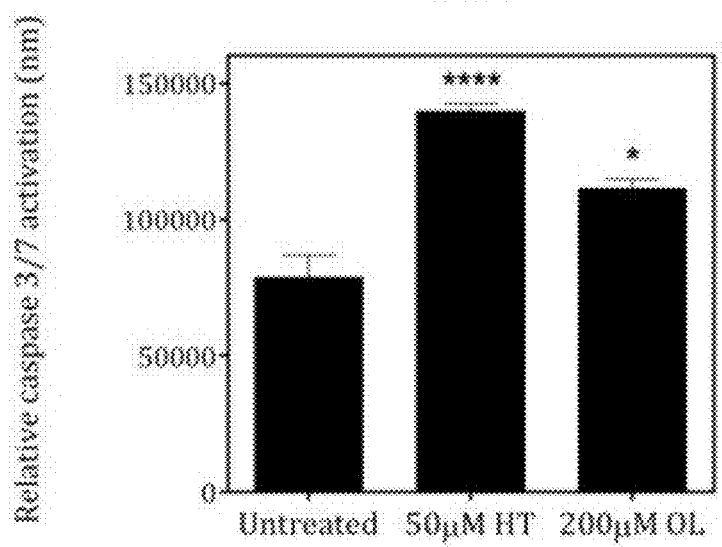
Figure 17A:
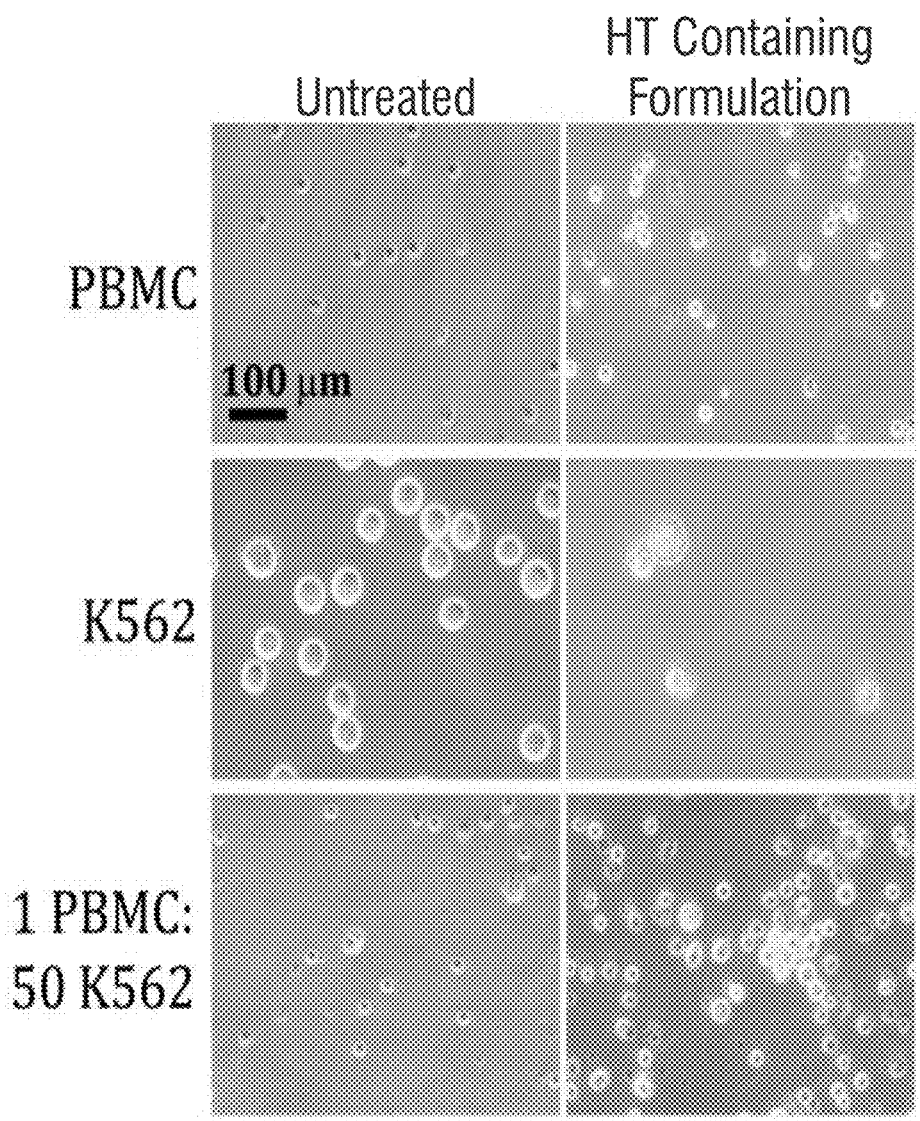
FIG. 17 (A-E) shows sensitization of K562 cells to immune surveillance by hydroxytyrosol according to an exemplary embodiment of the invention. (A) shows microscopic images of PBMC alone, K562 cells alone, or PBMC and K562 cells together in a ratio of 1 PBMC:50 K562 cells. Cells were either untreated or treated with a hydroxytyrosol-containing formulation according to the present invention. (B) shows the rate of cell proliferation of PBMC or K562 cells untreated or treated with a hydroxytyrosol-containing composition according to the present invention. (C) shows cell death of PBMC or K562 cells untreated or treated with a hydroxytyrosol-containing formulation according to the present invention. (D) shows the rate of cell proliferation of PBMC or K562 cells, incubated together in a ratio of 1 PBMC:50 K562 cells, untreated or treated with a hydroxytyrosol-containing formulation according to the present invention. (E) shows cell death of PBMC or K562 cells, incubated together in a ratio of 1 PBMC:50 K562 cells, untreated or treated with a hydroxytyrosol-containing formulation according to the present invention. Mean from a single experiment performed in duplicate are shown; total of 2 independent experiments tested.
Figure 17B:
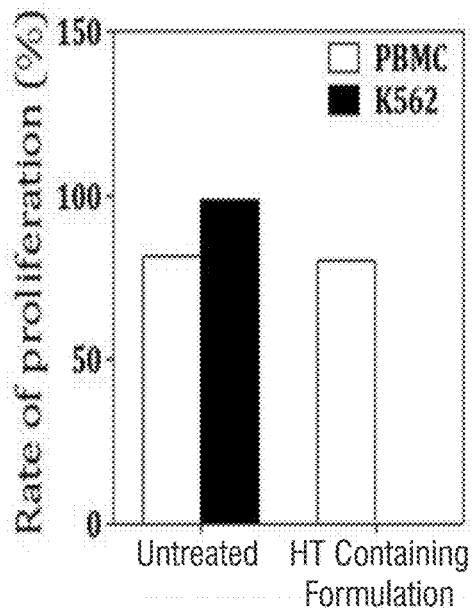
Figure 17C:
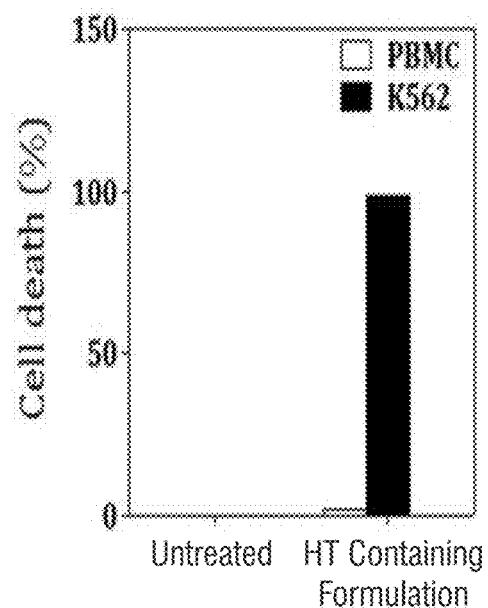
Figure 17D:
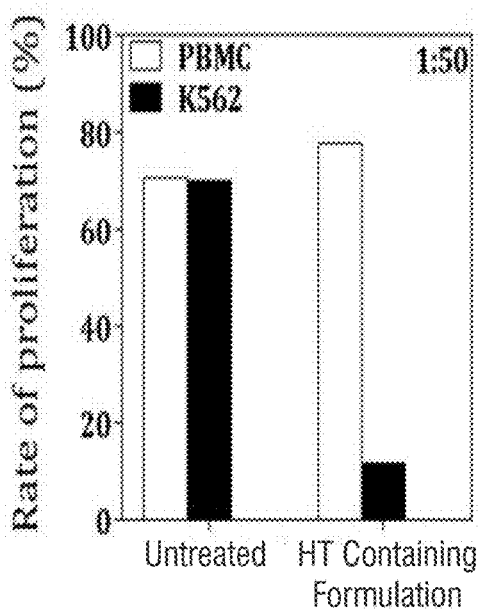
Figure 17E:
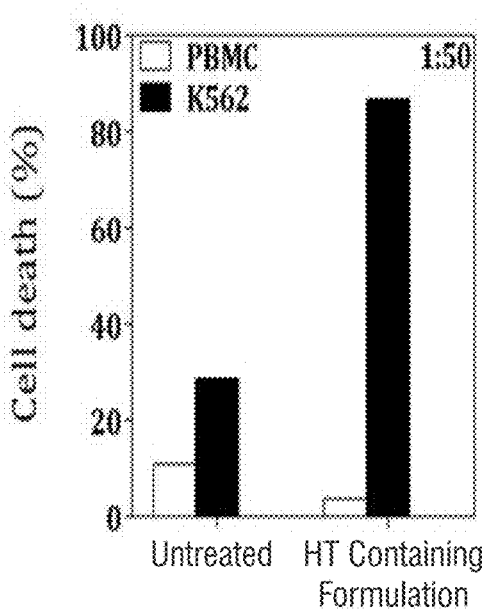

Effects of Hydroxytyrosol-Containing Formulations in Malignant Erythroleukemic and Normal Cells
Summary:
hydroxytyrosol-containing formulation sensitizes chronic myeloid leukemic K562 cells to immune surveillance by 65%.
Methods
Cell Viability Cells were seeded at densities of 7,500 cells/in black flat bottom 96-well plates (Nalge Nunc, Penfield, N.Y., USA) and treated with a dose response of Formulation 1, 2 (Table 7) for 24 hours at 37° C., 5% (v/v) $CO_2$. Cell viability was measured by the Cell Titer Blue assay kit as previously described.
Immune Surveillance Assay Normal peripheral blood mononuclear cells and erythroleukemic K562 cells were seeded at densities of $1 \times 10^6$/mL in 24 well culture (Nalge Nunc, New York, USA) and treated separately with hydroxytyrosol-containing formulation 2 (dilution factor 4) for 24 hours at 37° C., 5% (v/v) $CO_2$. Cells were then washed twice and co-incubated in ratios of 1:50; K562: PBMC for a further 24 hours at 37° C., 5% (v/v) $CO_2$. Cells were then incubated for with 5 μM Hoechst 33342 for 1 hour and 10 μM propidium iodide for 15 minutes prior to live imaging using an Olympus FSX100 Bio Imaging Navigator fluorescence microscope. Images were analyzed using Image J (Fiji, version 1.4) software and the number of dead cells shown by propidium iodide was quantified. Percentages of dead cells for the total population of cells per frame were calculated.
Results and Discussion Biological immune surveillance is the immune systems defense system within the human body to recognize and destroy not only invading pathogens but also host cells that become cancerous. A hydroxytyrosol-containing formulation of the present invention (Formulation 2, Table 9) sensitizes chronic myeloid leukemic K562 cells to immune surveillance by 65% (FIG. 17) by stimulation of rapid proliferation of normal peripheral blood cells, increasing the number of naturally occurring natural killer (NK) cells found in the population and enhancing cytotoxic immunity (FIG. 11).

Example 5

Hydroxytyrosol Induces Cell Death and Apoptosis Preferentially in Malignant Cells Compared to Normal Cells
Summary:
Hydroxytyrosol and oleuropein induce cell-death and apoptosis in human malignant cell lines but not in normal cells.
Methods
Cell Culture Human chronic myelogenous leukemia K562 cells (ATCC No. CCL-243), human large B-lymphocyte non-Hodgkin's lymphoma LCL cells, human leukemic monocyte lymphoma U937 cells (ATCC No. CRL-1593.2), human prostate adenocarcinoma PC3 (ATCC No. CRL-1435) and human gastric carcinoma SNU-16 cells (ATCC No. CRL-5974) were maintained in complete-Royal Park Memorial Institute (RPMI) 1640 medium supplemented with 20 mmol/L HEPES (pH 7.4; GIBCO-Invitrogen, Carlsbad, Calif., USA), 10% (v/v) fetal bovine serum (FBS), 2 mmol/L L-glutamine (GIBCO-Invitrogen), and 80 units gentamicin (GIBCO-Invitrogen). Cells were cultured in suspension in a humidified atmosphere of 5% (v/v) $CO_2$ at 37° C. and were maintained in exponential growth phase. For maintenance, cells were passaged twice per week and seeded at ratios 1:10.

Human peripheral blood mononuclear cells (PBMCs) were fractionated using the Ficoll Plaque fractionation method from whole blood obtained from the Australian Red Cross Blood Bank (ARCB) under ethic approval (#304/12). Cells were harvested fresh on the day of the experiments and maintained in complete-RPMI-1640 medium supplemented with 10% FBS, 2 mM L-glutamine and 20 μg/mL gentamicin at 37° C., 5% (v/v) $CO_2$.

Human cutaneous T cell lymphoma MyLa cells expressing $CD4^+$ (ECACC No. 95051032) and $CD8^+$ (ECACC No. 95051033) were obtained from the European Culture Collection of Cell Cultures (ECACC; CAMR, Salisbury, UK) and maintained in complete-RPMI 1640 medium supplemented with 2 mM glutamine (GIBCO-Invitrogen), 10% (v/v) human AB serum (Lonza, Basel, Switzerland) and 100 u/mL IL-2 (Sigma-Aldrich, USA) or 100 u/mL IL-2 (Sigma-Aldrich, USA) with 100 u/mL IL-4 (R&D Systems, MN, USA) respectively. Cells were cultured in suspension in a humidified atmosphere of 5% (v/v) CO2 at 37° C. and were maintained in exponential growth phase. For maintenance, cells were passaged three times per week and seeded at ratios 1:2. Liver hepatocellular carcinoma Hep G2 cells (ATCC No. Nb-8065) were maintained in RPMI-1640 supplemented with 10% fetal bovine serum (FBS), and were cultured in 75 $cm^2$ T-flask and maintained at 37° C. in 5% $CO_2$ humidified incubator.

Human acute T lymphoblast leukemic CEM-CCRF cells (ATTC NO. CCL-119), obtained from the ATCC were maintained in a Modified Eagle's Medium (α-MEM) supplemented with 2 mmol/L HEPES (pH 7.4; GIBCO-Invitrogen, Carlsbad, Calif., USA), 10% (v/v) FBS, 2 mmol/L L-glutamine (GIBCO-Invitrogen), and 80 units gentamicin (GIBCO-Invitrogen). Similarly, CEM-CCRF—P-glycoprotein (PGP)—over expressing, vinblastine derivative—R100 cells, expressing multi-drug resistance (MDR) were grown in a-MEM supplemented with 2 mmol/L HEPES (pH 7.4), 10% (v/v) FBS, 2 mmol/L L-glutamine, 80 units gentamicin and 100 ng/ml vinblastine. R100 cells were cultured in a-MEM/FBS/gentamicin media without vinblastine for 7 days prior to use in experiments. Cells were cultured in suspension in a humidified atmosphere of 5% (v/v) $CO_2$ at 37° C. and were maintained in exponential growth phase. For maintenance, cells were passaged twice per week and seeded at ratios 1:10.

Human acute myeloid leukemic HL-60 cells (ATCC No. CCL-240) obtained from the ATCC were maintained in Dulbecco's modified Eagle's medium (DMEM, Gibco®, Invitrogen, Carlsbad, USA) supplemented with 20% fetal bovine serum (FBS, In Vitro Technologies, Victoria, Australia), antibody/antimycotic containing 100 U/mL Penicillin, 100 µg/mL Streptomycin, 0.25 µg/mL Amphotericin B (Invitrogen, Carlsbad, Calif., USA) and 1× GlutaMAX (Gibco, Invitrogen). Cells were cultured in suspension in a humidified atmosphere of 5% (v/v) $CO_2$ at 37° C. and were maintained in exponential growth phase. For maintenance, cells were passaged twice per week and seeded at ratios 1:10.

Human epidermal squamous carcinoma A431 cells (ATCC No. CRL-1555), human breast adenocarcinoma MCF7 cells (ATCC No. HTB-22) and brain glioblastoma T98G cells (ATCC No. CRL-1690) obtained from the ATCC were grown as monolayers in a Modified Eagle's Medium (a-MEM) supplemented with 2 mmol/L HEPES (pH 7.4; GIBCO-Invitrogen), 10% (v/v) FBS, 2 mmol/L L-glutamine (GIBCO-Invitrogen), and 80 units gentamicin (GIBCO-Invitrogen). Human epithelial lung adenocarcinoma A549 cells (ATCC No. CCL-185), human liver hepatocellular carcinoma and human colorectal carcinoma HT-29 cells (ATCC No. HTB-38) were obtained from the American Type Culture Collection and grown as monolayers in DMEM (Gibco, Invitrogen) supplemented with 10% (v/v) FBS (In Vitro Technologies), antibody/antimycotic containing 100 U/mL Penicillin, 100 µg/mL Streptomycin, 0.25 µg/mL Amphotericin B (Invitrogen, Carlsbad). All adherent cells were maintained in the exponential growth phase in T75 $cm^2$ vented culture flasks and passaged by 0.05% (v/v) trypsin-EDTA (GIBCO, Invitrogen) before seeding; at 37° C., 5% (v/v) $CO_2$.

Cell Proliferation and Apoptosis

Cell proliferation was determined using the Cell Titer-Blue Assay kit (Promega, Madison, Wis., USA). Cells were seeded at 10,000 cells per well in black flat bottom 96-well plates (Nalge Nunc, Penfield, N.Y., USA) and treated with serial doses of hydroxytyrosol (0-3200 µM) and oleuropein (0-12800 µM) for 24, 48 and 120 hours at 37° C., 5% (v/v) $CO_2$. Following incubation with the test samples, Cell-Titer Blue reagent (20 µl per 100 µL) was added to each well and mixed gently for 5 sec prior to 4 hr incubation at 37° C. in a humidified atmosphere of 5% $CO_2$. Fluorescence intensity ($\lambda ex=550$ nm and $\lambda em=615$ nm) was determined using a Perkin Elmer Victor3 multilabel microplate counter (PerkinElmer, Waltham, Mass., USA). Data were expressed as % relative cell viability compared to untreated cells after correction of subtracting the media control fluorescence reading.

Apoptosis was determined following 24 hours incubation with 50 µM hydroxytyrosol and 200 µM oleuropein prior to cell lysis and measuring caspase-3/7 enzymatic activity with Apo-ONE Homogeneous Caspase-3/7 Assay kit (Promega, Wis., USA), according to the manufacturer's instructions. Following determination of growth inhibition as described above, Apo-1 substrate/buffer mix was added to each well at a ratio of 1:1 and incubated for 4 hours on a rotating platform in the dark at 22° C. The fluorescence intensity ($\lambda ex=485$ nm and $\lambda em=525$ nm) was determined on a Victor3 multilabel plate counter (PerkinElmer, Waltham, Mass., USA). Apoptosis was reported as the change in fluorescence over 4 hours and after subtraction of the media control.

Statistical Analysis

Statistical analysis was measured using Prism (version 6, GraphPad Software, San Diego, Calif., USA). A one-way analysis of variance (ANOVA) was employed, with a Bonferroni post-test to determine the statistical significance between differing treatments. The level of significance was accepted at $*p<0.05$, $p<0.01$, $*p<0.001$ and $****p<0.0001$.

Results and Discussion

Our findings indicate that hydroxytyrosol induces cell-death and apoptosis preferentially in malignant cells compared to normal cells. In vitro studies investigating the effects of hydroxytyrosol and oleuropein on proliferation in numerous normal and malignant cells (Table 1) show both hydroxytyrosol and oleuropein decreases the viability and inhibit proliferation of all malignant cells in a dose dependent manner following 24 hours treatment (FIGS. 12-15).

TABLE 1

Publicly available cell lines used to investigate the biological effects of olive constituents; hydroxytyrosol and oleuropein.

| | |
|---|---|
| PBMC | normal peripheral white blood |
| K562 | chronic myeloid leukemia (CML) |
| HL-60 | acute myeloid leukemia (AML) |
| MyLa CD4+ | cutaneous T cell lymphoma (CTCL) |
| MyLa CD8+ | cutaneous T cell lymphoma (CTCL) |
| CEM CCRF | acute T lymphoblast leukemia (ALL) |
| R100 | MDR acute T lymphoblast leukemia (MDR ALL) |
| LCL-25 | large B-lymphocyte non-Hodgkin's lymphoma |
| U937 | leukemic monocyte lymphoma |
| A431 | epidermal squamous carcinoma |
| A549 | epithelial lung adenocarcinoma |
| Hep G2 | liver hepatocellular carcinoma |
| HT-29 | colorectal carcinoma |
| MCF7 | breast adenocarcinoma |
| TG98 | brain glioblastoma |
| PC3 | prostate adenocarcinoma |
| SNU-16 | gastric carcinoma |

Furthermore, $EC_{50}$ values defined as the concentration (µM) of hydroxytyrosol or oleuropein required to inhibit 50% of proliferation in the cell population is shown following 24 hours treatment (Table 2). Haematological malignant cell lines were found to require smaller concentrations of hydroxytyrosol and oleuropein to augment proliferation when compared to the non-haematological malignant cell lines investigated (Table 2). The human cells lines, chronic myeloid leukemia K562 and acute T lymphoblast leukemia CEM-CCRF required the lowest concentrations of hydroxytyrosol to inhibit proliferation with $EC_{50}$ values of 150 µM and 121 µM respectively (Table 2). Oleuropein was most effective in the K562 cell line also with an $EC_{50}$ value of 337 µM. In most cell lines approximately a dose four times more concentrated was required of oleuropein to achieve $EC_{50}$ when compared to hydroxytyrosol.

TABLE 2

The $EC_{50}$ (μM) values of hydroxytyrosol (HT) and oleuropein (OL) following 24 hours of treatment.

| Cell line | HT (μM) | | | OL (μM) | | |
|---|---|---|---|---|---|---|
| | Mean | SEM | N | Mean | SEM | N |
| PBMC | 855 | 65 | 3 | 2707 | 410 | 3 |
| K562 | 150 | 18 | 3 | 337 | 42 | 3 |
| HL-60 | 632 | 109 | 3 | 717 | 121 | 3 |
| MyLa CD4+ | 1012 | 274 | 3 | 647 | 158 | 3 |
| MyLa CD8+ | 460 | 112 | 3 | 647 | 183 | 3 |
| CEM-CCRF | 121 | 15 | 3 | 437 | 101 | 3 |
| R100 | 190 | 59 | 3 | 320 | 89 | 3 |
| LCL | 370 | 85 | 3 | 403 | 130 | 3 |
| U937 | 563 | 179 | 3 | 730 | 188 | 3 |
| A431 | 870 | 113 | 3 | 1750 | 391 | 3 |
| A549 | 417 | 60 | 3 | 1083 | 361 | 3 |
| Hep-G2 | 427 | 104 | 3 | 703 | 250 | 3 |
| HT-29 | 800 | 85 | 3 | 1577 | 480 | 3 |
| MCF7 | 580 | 16 | 3 | 4750 | 531 | 3 |
| T98G | 1340 | 376 | 3 | 2767 | 1164 | 3 |
| PC3 | 2117 | 580 | 3 | 2293 | 207 | 3 |
| SNU-16 | 1100 | 163 | 3 | 2825 | 1123 | 3 |

In addition, investigation of the $EC_{50}$ values following 24, 48 and 120 hours incubations of hydroxytyrosol and oleuropein showed that $EC_{50}$ values decreased in response to incubation time of the olive constituents (Table 3).

TABLE 3

Time-dependent $EC_{50}$ (μM) values of hydroxytyrosol (HT) and oleuropein (OL).

| Cell line | HT (μM) | | | OL (μM) | | |
|---|---|---|---|---|---|---|
| | 24 hr | 48 hr | 120 hr | 24 hr | 48 hr | 120 hr |
| PBMC | 855 | NA | NA | 2707 | NA | NA |
| K562 | 150 | 150 | 91 | 337 | 950 | 585 |
| HL-60 | 632 | 100 | 13 | 717 | 900 | 100 |
| MyLa CD4+ | 1012 | 870 | 400 | 647 | 3800 | 3400 |
| MyLa CD8+ | 460 | 450 | 230 | 647 | 3600 | 270 |
| CEM-CCRF | 121 | 100 | 42 | 437 | 1800 | 325 |
| R100 | 190 | 100 | 40 | 320 | 1000 | 250 |
| LCL | 370 | 200 | 94 | 403 | 1100 | 640 |
| U937 | 563 | 500 | 250 | 730 | 2800 | 1250 |
| A431 | 870 | 920 | 480 | 1750 | 4400 | 2900 |
| A549 | 417 | 220 | 160 | 1083 | 1100 | 1220 |
| Hep-G2 | 427 | 470 | 205 | 703 | 2400 | 1300 |
| HT-29 | 800 | 230 | 310 | 1577 | 2500 | 1850 |
| MCF7 | 580 | 900 | 520 | 4750 | 3000 | 4100 |
| T98G | 1340 | 1750 | 700 | 2767 | 6100 | 5500 |
| PC3 | 2117 | 320 | 215 | 2293 | 3800 | 2500 |
| SNU-16 | 1100 | 80 | NA | 2825 | 800 | NA |

Given the 120 hour time point yielded remarkable cell death and the greatest inhibitory effects in proliferation of malignant cells, EC10 values; defined as the concentration required to reduce the cell viability of the population to 10%, were calculated also (Table 4). Acute myeloid leukemia HL-60 cells were found to have the smallest $EC_{50}$ and $EC_{10}$ values following a 120 hour treatment with hydroxytyrosol at 13 μM and 29 μM respectively. Acute T lymphoblast leukemic cell lines CEM-CCRF and its multidrug resistant derivative R100 cells followed with $EC_{50}$ values of 42 μM and 40 μM respectively and $EC_{10}$ values of 80 μM and 86 μM respectively (Table 4). Again, the olive constituents were more effective in reducing the proliferation of haematological malignant cell lines when compared to non-haematological malignant cell lines investigated. Finally, the data presented shows that the biological effects observed in the malignant cell lines where not seen in normal peripheral blood mononuclear cells (PBMC) (FIG. 12, 19). More importantly, following 120 hour treatment with hydroxytyrosol or oleuropein, cell proliferation was attenuated in PBMCs.

TABLE 4

$EC_{50}$ and $EC_{10}$ (μM) values following a 120 hr incubation with hydroxytyrosol (HT) and oleuropein (OL)

| | EC50 | | EC10 | |
|---|---|---|---|---|
| Cell line | HT (μM) | OL (μM) | HT (μM) | OL (μM) |
| PBMC | NA | NA | NA | NA |
| K562 | 91 | 585 | 176 | 756 |
| HL-60 | 13 | 100 | 29 | 230 |
| MyLa CD4+ | 400 | 3400 | 760 | 4800 |
| MyLa CD8+ | 230 | 270 | 650 | 3020 |
| CEM-CCRF | 42 | 325 | 80 | 700 |
| R100 | 40 | 250 | 86 | 530 |
| LCL | 94 | 640 | 177 | 1240 |
| U937 | 250 | 1250 | 370 | 2600 |
| A431 | 480 | 2900 | 1000 | 4450 |
| A549 | 160 | 1220 | 320 | 1540 |
| Hep-G2 | 205 | 1300 | 360 | 2600 |
| HT-29 | 310 | 1850 | 380 | 2950 |
| MCF7 | 520 | 4100 | 750 | 4700 |
| T98G | 700 | 5500 | 1120 | 6220 |
| PC3 | 215 | 2500 | 630 | 4600 |

The Apo-One homogenous caspase 3/7 assay was used to measure the relative caspase 3/7 induction in haematological malignant and normal peripheral blood cells. Cells were pre-treated with either 50 μM hydroxytyrosol and 100 μM oleuropein for 24 hours prior to cell lysis by the Apo-One assay reagents. The results show significant augmentation in the induction of caspase 3/7 apoptosis in all haematological cell lines investigated by either hydroxytyrosol or oleuropein but not normal peripheral blood cells (PBMC) (FIG. 16). In most cell lines, both hydroxytyrosol and oleuropein were found to be effective.

Example 6

Hydroxytyrosol Induces Genetic and Epigenetic Effects in Malignant K562 Cells and Transformed Human Keratinocytes.

Summary:

mRNA-Seq indicates that hydroxytyrosol regulates the expression of various genes in a dose-dependent manner—genes associated with cell-death, cell cycle and apoptosis are regulated in K562 cells. Antioxidant and anti-inflammatory pathways are modulated in human keratinocytes. In vitro assays indicate that hydroxytyrosol is a potent inhibitor of lysine-specific demethylase 1 (LSD1).

Methods

Cell Culture

Human chronic myelogenous leukemia K562 cells (ATCC No. CCL-243) were obtained from the American Type Culture Collection (Manassas, Va., USA) and maintained in complete-Royal Park Memorial Institute (RPMI) 1640 medium supplemented with 20 mmol/L HEPES (pH 7.4; GIBCO-Invitrogen, Carlsbad, Calif., USA), 10% (v/v) fetal bovine serum (FBS), 2 mmol/L L-glutamine (GIBCO-Invitrogen), and 80 units gentamicin (GIBCO-Invitrogen). Cells were cultured in suspension in a humidified atmosphere of 5% (v/v) $CO_2$ at 37° C. and were maintained in exponential growth phase. For maintenance, cells were passaged twice per week and seeded at ratios 1:10. Human neonatal foreskin keratinocytes transfected with the human papilloma virus (HPV) were grown as monolayers in keratinocyte—Serum Free Medium (SFM) medium (GIBCO-Invitrogen) supplemented with L-glutamine, human epidermal growth factor (EGF), and bovine pituitary extract (BPE) at 37° C., 5% (v/v) $CO_2$. Cells were passaged by trypsinisation and seeded at ratio of 1:3.

mRNA-Sequencing

Cells were seeded at densities of $1\times10^6$/mL in culture flasks (Nalge Nunc, New York, USA) and treated with hydroxytyrosol (0, 20, 100 µM), for 24 hours at 37° C., 5% (v/v) $CO_2$. mRNA sequencing was performed by TRIZOL extraction and library preparation using Illumina kits according to manufacturer's protocols. Next generation sequencing (NGS) was performed at a depth of approximately 20 million mapped reads per sample to determine the effect of hydroxytyrosol on genome-wide gene expression, in human erythroleukemic K562 cells and human keratinocytes (24 hr treatment, 20 and 100 µM). Reads generated by the Illumina base calling software V1.6 were aligned with Burrows Wheeler Aligner to the human transcriptome database curated by RefSeq (Hg18 build). Raw counts were normalized to adjust for slightly differing data volume across lanes giving the widely used score reads per transcript per million reads. These scores were used to determine relative fold changes and the conventionally used ±1.5 fold-change, which is discernible with qRT-PCR, was defined a significant change in expression. The online program MetaCore (GeneGo Inc. St. Joseph, MI, USA) was used for pathway analysis.

LSD1 Demethylase Profiling

Formulation 2 (4× diluted) was tested against positive control tranylcypromine for LSD1 inhibition activity. Formulation 2 (4× diluted) was tested in 10-dose $IC_{50}$ mode with 3-fold serial dilution in singlet starting at 100 µM and control compound, Tranylcypromine, was tested in 10-dose $IC_{50}$ mode with 3-fold serial dilution starting at 100 µM. The production of FAD-dependent $H_2O_2$ as a result of demethylase activity of LSD1 is measured by coupling with HRP and Amplex Red and fluorescence was measured using the EnVision plate reader at Ex/Em=535/590 nm. 10 µM Histone H3 (1-21) K4me2 peptide was used as the standard substrate. Data was represented at the percentage of LSD1 enzymatic activity inhibition relative to DMSO controls and a curve fit for the control compound.

Results and Discussion

These findings indicate that hydroxytyrosol induces cell-death and apoptosis preferentially in malignant K562 cells compared to PMBC cells. Similarly, the findings indicate that hydroxytyrosol induces DNA-double strand breaks in K562 cells but not normal PBMC. Analysis of genome-wide mRNA-Seq data indicates that hydroxytyrosol affects pathways associated with cell-death, apoptosis and cell cycle regulation. Further, these studies have identified that hydroxytyrosol regulates the expression of numerous genes associated with epigenetic processes. In particular, the findings indicate changes associated with DNA methyltransferases and histone deacetylase enzymes, suggesting that hydroxytyrosol may influence chromatin architecture by altering histone post-translational modifications (FIG. 18). Table 5 shows changes in expression of epigenetic-related genes in cancer cells following exposure to hydroxytyrosol according to an exemplary embodiment of the invention. DNA methyltransferase and histone deacetylase gene expression was assessed following exposure to 20 µM or 100 µM hydroxytyrosol.

TABLE 5

Changes in expression of epigenetic-related genes in cancer cells following exposure to hydroxytyrosol-containing formulation

| Gene Symbol | Gene Name | Fold Change |
|---|---|---|
| 20 µM HT | | |
| UP | | |
| PRDM6 | PR domain containing 6 | 3.50 |
| DOWN | | |
| PRDM12 | PR domain containing 12 | 1.50 |
| KDM4C | lysine (K)-specific demethylase 4C | 1.61 |
| PHF8 | PHD finger protein 8 | 1.62 |
| NCOA2 | nuclear receptor coactivator 2 | 1.63 |
| PRDM1 | PR domain containing 1, with ZNF domain | 1.68 |
| HDAC9 | histone deacetylase 9 | 1.82 |
| HDAC9 | histone deacetylase 9 | 2.00 |
| PRMT8 | protein arginine methyltransferase 8 | 2.13 |
| 100 µM HT | | |
| UP | | |
| SETD7 | SET domain containing (lysine methyltransferase) 7 | 3.41 |
| HDAC9 | histone deacetylase 9 | 2.05 |
| PPARGC1A | peroxisome proliferator-activated receptor gamma, coactivator 1 alpha | 2.00 |
| PRDM12 | PR domain containing 12 | 2.00 |
| PRDM9 | PR domain containing 9 | 1.85 |
| KDM4A | lysine (K)-specific demethylase 4A | 1.71 |
| KDM6B | lysine (K)-specific demethylase 6B | 1.70 |
| SMYD3 | SET and MYND domain containing 3 | 1.60 |
| SMYD3 | SET and MYND domain containing 3 | 1.57 |
| RPS6KA5 | ribosomal protein S6 kinase, 90 kDa, polypeptide 5 | 1.56 |
| HDAC9 | histone deacetylase 9 | 1.50 |
| DOWN | | |
| NCOA2 | nuclear receptor coactivator 2 | 1.50 |
| GTF3C4 | general transcription facto IIIC, polypeptide 4, 90 kDa | 1.55 |
| SETD1A | SET domain containing 1A | 1.56 |
| EHMT1 | euchromatic histone-lysine-N-methyltransferase 1 | 1.63 |
| KDM4C | lysine (K)-specific demethylase 4C | 1.66 |
| MLL3 | myeloid/lymphoid or mixed-lineage leukemia 3 | 1.68 |
| HDAC7 | histone deacetylase 7 | 1.76 |
| PRDM15 | PR domain containing 15 | 1.78 |
| HDAC7 | histone deacetylase 7 | 1.78 |
| PRMT8 | protein arginine methyltransferase 8 | 1.89 |
| PRDM10 | PR domain containing 10 | 1.92 |
| PRDM6 | PR domain containing 6 | 2.00 |
| NPM2 | Nucleophosmin/nucleoplasmin 2 | 3.33 |

Figure 18A:
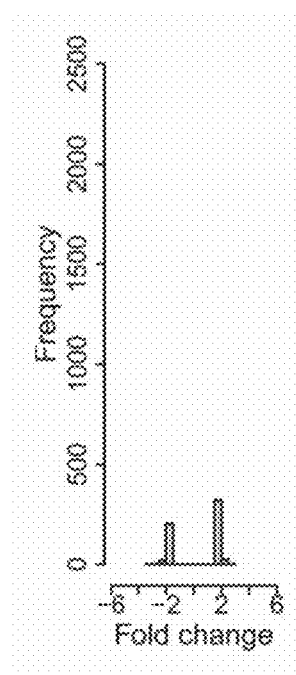
FIG. 18 (A-D) shows the number of genes differentially expressed in cancer cells following treatment with hydroxytyrosol according to an exemplary embodiment of the invention. (A) shows gene expression following exposure to 20 µM hydroxytyrosol for 24 hours. (B) shows gene expression following exposure to 100 µM hydroxytyrosol for 24 hours of PBMC or K562 cells, incubated together in a ratio of 1 PBMC:50 K562 cells, untreated or treated with a hydroxytyrosol-containing composition according to the present invention. (C-D) shows induction of genetic and epigenetic effects in human keratinocyte cells by hydroxytyrosol. (C) Histograms depict the number of genes differentially expressed following treatment with 20 µM hydroxytyrosol. (D) Hydroxytyrosol modifies the methylation status of histones differentially in malignant and normal cell lines. Western blot analysis shows epigenetic modification are altered differentially following treatment with 100 µM hydroxytyrosol in chronic myeloid leukemic cell K562 and normal peripheral blood cells PBMCs. Hydroxytyrosol increases di-methylation at histone H3 on lysine 9 but decreases di-methylation in PBMCs. SAHA shown as a positive control. Unmodified Histone H3 was used a loading control.
Figure 18B:
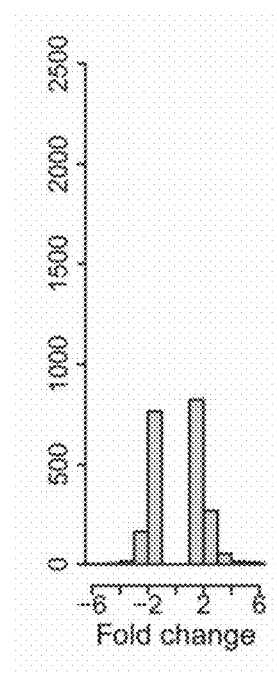
Figure 18C:
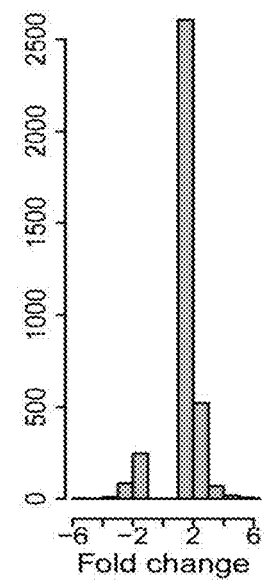

In addition, our findings indicate that hydroxytyrosol protects human skin keratinocytes from radiation-induced DNA damage (FIG. 20). Next generation sequencing analysis was used to explore potential mechanisms of action. The findings indicate that hydroxytyrosol regulates the expression of approximately ~3 thousand genes, the majority being up-regulated by 2-fold (FIG. 18C). Chromosomal analysis indicates that differential gene expression can be observed on the entire chromosome. As shown in Table 6, pathway analysis, using GeneGo, indicates that hydroxytyrosol affects intrinsic antioxidant pathways in the cells. In particular heme oxygenase 1 (HMOX-1) is up-regulated by 15-fold. Analysis of the sequencing data also indicates altered expression of genes associated with epigenetic mechanisms. Predominantly, hydroxytyrosol regulates the expression of histone methyltransferases, demethylases and histone deacetylase enzymes. This indicates regulation of the epigenome, particularly, histone post-translational modifications.

TABLE 6

Pathway analysis using GeneGo

| Gene Symbol | Gene Name | Fold Change |
|---|---|---|
| UP | | |
| PRDM1 | PR domain containing 1, with ZNF domain | 4.00 |
| HDAC9 | histone deacetylase 9 | 3.00 |
| PRDM11 | PR domain containing 11 | 3.00 |
| PRDM1 | PR domain containing 1, with ZNF domain | 2.67 |
| PRDM8 | PR domain containing 8 | 1.85 |
| HDAC5 | histone deacetylase 5 | 1.81 |
| SETDB2 | SET domain, bifurcated 2 | 1.75 |
| HDAC5 | histone deacetylase 5 | 1.70 |
| JHDM1D | jumonji C domain containing histone demethylase 1 homolog D (S. cerevisiae) | 1.66 |
| HDAC11 | histone deacetylase 11 | 1.65 |
| KDM2B | lysine (K)-specific demethylase 2B | 1.64 |
| PRDM8 | PR domain containing 8 | 1.64 |
| KDM3A | lysine (K)-specific demethylase 3A | 1.60 |
| PRDM4 | PR domain containing 4 | 1.56 |
| KDM2B | lysine (K)-specific demethylase 2B | 1.55 |
| HDAC11 | histone deacetylase 11 | 1.54 |
| SETMAR | SET domain and mariner transposase fusion gene | 1.53 |
| ELP3 | elongation protein 3 homolog (S. cerevisiae) | 1.51 |
| NCOA1 | Nuclear receptor coactivator 1 | 1.51 |
| DOWN | | |
| PRDM12 | PR domain containing 12 | 1.50 |
| SMYD3 | SET and MYND domain containing 3 | 1.55 |
| KDM5D | lysine (K)-specific demethylase 5D | 2.00 |
| MLL3 | myeloid/lymphoid or missed-lineage leukemia 3 | 2.00 |
| PRMT8 | protein arginine methyltransferase 8 | 2.00 |
| SETBP1 | SET binding protein 1 | 2.00 |

Finally in vitro studies indicate hydroxytyrosol is a potent inhibitor of lysine-specific demethylase 1 (LSD1) (FIG. 14). Importantly, the hydroxytyrosol composition of the invention demonstrated more potent inhibition of LSD1 than tranylcypromine. Tranylcypromine is a known irreversible inhibitor of LSD1 that is currently undergoing phase II clinical trials for treatment of acute myeloid leukemia patients. The effective concentration of the hydroxytyrosol composition of the invention at which 50% of LSD1 activity was inhibited ($EC_{50}$) was approximately 5 lower than that of tranylcypromine. In addition, this effective concentration is also lower than those reported for other novel LSD1 inhibitors. For example, the novel inhibitors reported by Wang et al., Cancer Res. 71(23): 7238-7249 (2011), exhibited half maximal inhibitory concentrations at 5.27-11.16 µM (5.27-11.16 e-006 M), while Namoline, reported by Willmann et al., Int. J. of Cancer 131(11): 2704-09 (2012), has a reported $IC_{50}$ of 50 µM (50 e-006). Thus, the hydroxytyrosol composition according to the present invention is a more potent inhibitor of LSD1 than other drugs currently being pursed for cancer treatment, including drugs currently in clinical trials.

Example 7

Hydroxytyrosol Modifies Histone Methylation by Inhibiting Lysine Demethylase 1 (LSD1)

Summary:

In vitro assays indicate that hydroxytyrosol inhibits lysine demethylase 1 (LSD1) by direct binding to its substrates and subsequently effects the methylation status of histones in malignant cells.

Methods

LSD1 Demethylase Profiling

Hydroxytyrosol was tested against positive control tranylcypromine for LSD1 inhibition activity. Hydroxytyrosol was tested in 10-dose $IC_{50}$ mode with 3-fold serial dilution in singlet starting at 100 µM and control compound, Tranylcypromine, was tested in 10-dose $IC_{50}$ mode with 3-fold serial dilution starting at 100 µM. The production of FAD-dependent $H_2O_2$ as a result of demethylase activity of LSD1 is measured by coupling with HRP and Amplex Red and fluorescence was measured using the EnVision plate reader at Ex/Em=535/590 nm. 10 µM Histone H3 (1-21) K4me2 peptide was used as the standard substrate. Data was represented at the percentage of LSD1 enzymatic activity inhibition relative to DMSO controls and a curve fit for the control compound.

Western Blotting

Cells were treated with or without 100 µM hydroxytyrosol for 24 hours prior to collection of whole cell lysates using Mammalian Protein Extraction Reagent (M-PER; Thermo Scientific, Rockford, USA). Total protein was measured using a Bradford Assay with Bovine Serum Albumin (BSA; Sigma-Aldrich) at 595 nM using a Emax Precision microplate reader. Equal amounts of protein (40 µg/lane) were fractionated using 12% SDS-PAGE and transferred to nitrocellulose membranes. The membranes were incubated overnight with primary antibodies polyclonal rabbit anti-H3K9me3 (1:500; Abcam) and polyclonal rabbit anti-acetylated histone H3 (1:2000; 06-599, Millipore). The membranes were incubated with peroxidise-conjugated goat anti-mouse or donkey anti-rabbit secondary antibodies (1:10000) followed by enhanced chemilluminescence staining.

Results and Discussion

Figure 18D:
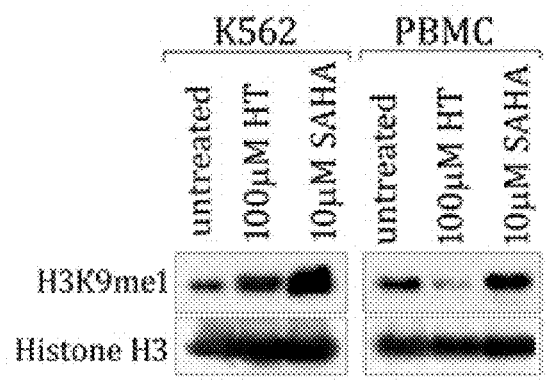
Figure 19:
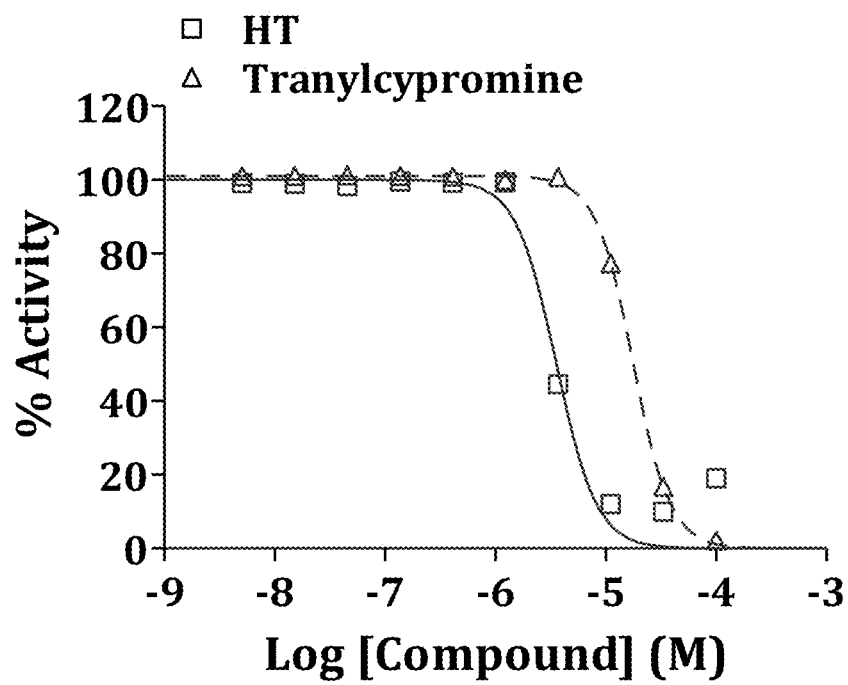
FIG. 19 shows that hydroxytyrosol is a potent inhibitor of lysine-specific demethylase 1 (LSD1) according to an exemplary embodiment of the invention. The known LDS1 inhibitor tranylcypromine is shown a positive control.

In vitro studies investigating the inhibitory potential of hydroxytyrosol to LSD1 indicate hydroxytyrosol is a potent inhibitor of LSD1 (FIG. 19). The FDA approved LSD1 inhibitor tranylcypromine was used as a positive control. The data shows hydroxytyrosol to be a more effective LSD1 inhibitor against tranylcypromine. A direct target of LSD1 is histone H3 at lysine 9. Western blot analysis shows hydroxytyrosol modifies histone H3 lysine 9 (H3K9) di-methylation differentially in chronic myeloid leukemic K562 cells and normal peripheral blood mononuclear cells (PBMC). Following treatment with hydroxytyrosol, di-methylation was increased in K562 cells but decreased in PBMC cells (FIG. 18D).

Example 8

Overview of the Protective Effects of Hydroxytyrosol, Oleuropein, Alone and in Combination, in Human Keratinocytes Summary:

Hydroxytyrosol-containing Formulations reduce the cytotoxic effects induced by $H_2O_2$ and doxorubicin, represented by reduced γH2AX formation.

Methods

Cell Culture

Human neonatal foreskin keratinocytes transfected with the human papilloma virus (HPV) were grown as monolayers in keratinocyte—Serum Free Medium (SFM) medium (GIBCO-Invitrogen) supplemented with L-glutamine, human epidermal growth factor (EGF), and bovine pituitary extract (BPE) at 37° C., 5% (v/v) $CO_2$.

Cell Viability and Apoptosis

Cells were pre-treated with hydroxytyrosol (dilution factor 1=200 µM), oleuropein (dilution factor 1=50 µM) and the Formulations 1 and 2 (Table 9) for 24 hours; 37° C., 5% (v/v) $CO_2$. In separate experiments, cells were treated with Formulation 3 (Table 9) for 24 hours prior to 24 hour incubation with 30 µM $H_2O_2$ or were treated with McCord Formulation 2 for 24 hours prior to 24 hours incubation with 0.25 µM doxorubicin; 37° C., 5% (v/v) $CO_2$. Cell viability was measured using the Cell-Titer Blue® Assay kit (Promega, Madison, Wis., USA) as previously described.

γH2AX Immunofluorescence

Keratinocytes pre-treated with Formulations 1, 2 and 3 (Table 9) for 24 hours prior to exposure to 0, 2 and 12 Gy (137Cs) and incubated for a further hour; 37° C., 5% (v/v) $CO_2$, before staining for γH2AX as previously described.

Results and Discussion

Figure 20A:
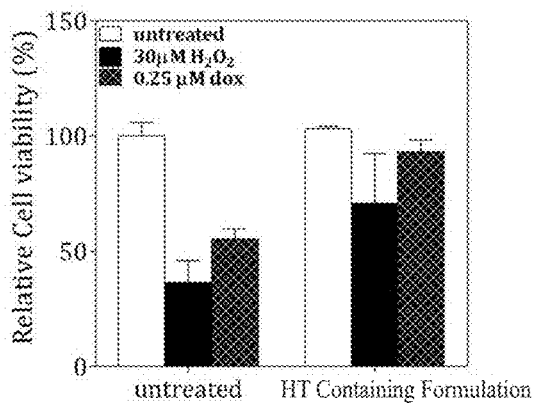
FIG. 20 (A-D) shows an overview of the protective effects of hydroxytyrosol-containing formulation in human keratinocytes according to an exemplary embodiment of the present invention. (A) Hydroxytyrosol-containing formulation reduces cytotoxic effects induced by $H_2O_2$ and doxorubicin. (B) Hydroxytyrosol (HT) and oleuropein (OL) reduces γ-radiation DNA damage in a dose-dependent manner. (C-D) The hydroxytyrosol-containing formulation dramatically protects human keratinocytes from γ-radiation induced DNA damage to a greater extent with the presence of HT and OL.
Figure 20B:
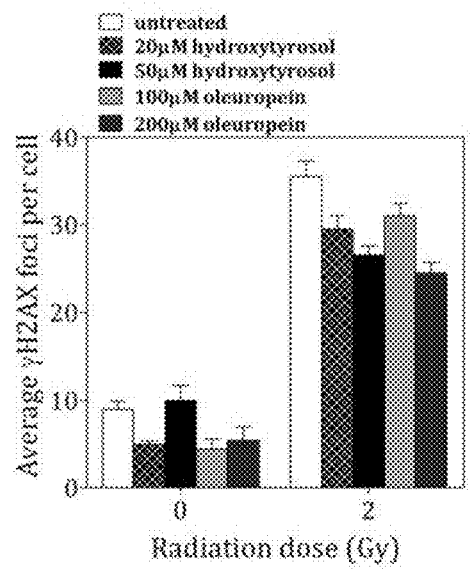
Figure 20C:
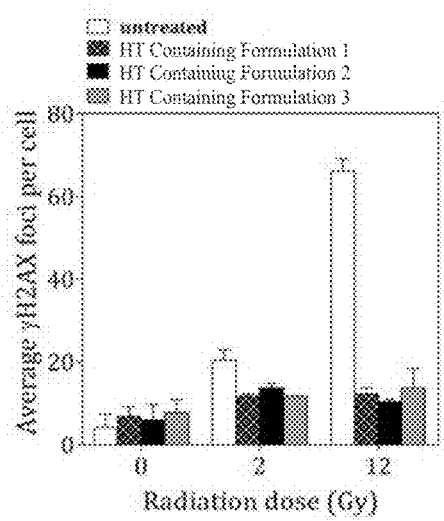
Figure 20D:
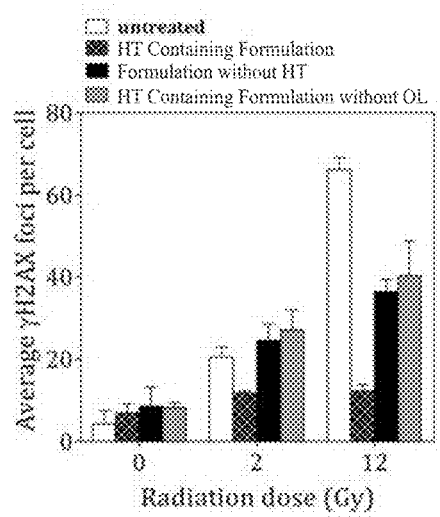

These studies explored the protective potential of variations of HT-containing formulations 1, 2, and 3 (Table 9) to confer the highest radioprotective activity warranting further investigation. The findings indicate that the formulation protects from damage induced by hydrogen peroxide and the anthracycline, doxorubicin (FIG. 20A). In addition, potent protection from ionizing radiation-induced DNA damage was observed (FIG. 20C, D). Removal of the olive phenolics, hydroxytyrosol or oleuropein from the formulation highlights the importance of these compounds in conferring radioprotective activity. Overall, the findings indicate a potential role for the hydroxytyrosol-containing Formulations of the invention in ameliorating acute skin side effects associated with cancer radiotherapy.

Example 9

Effects of Hydroxytyrosol-Containing Formulations on Wound Healing Parameters—In Vitro Studies Summary:

An exemplary hydroxytyrosol-containing Formulation improves the migration of keratinocytes, human microvascular endothelial and human umbilical vein endothelial cells following treatment with high glucose and doxorubicin.

Methods

Cell Culture

Human neonatal foreskin keratinocytes transfected with the human papilloma virus (HPV), kindly provided by Dr. Pritinder Kaur (Peter McCallum Cancer Institute) were grown as monolayers in keratinocyte—Serum Free Medium (SFM) medium (GIBCO-Invitrogen) supplemented with L-glutamine, human epidermal growth factor (EGF), and bovine pituitary extract (BPE). Human microvascular endothelial cells (HMEC-1) transfected with the rous sarcoma virus were obtained from the American Type Culture Collection (Manassas, Va., USA) and grown as monolayers in MCDB-131 medium (GIBCO-Invitrogen) supplemented with L-glutamine, epidermal growth factor (EGF), heparin, hydrocortisone and Gluta-MAX (GIBCO-Invitrogen). Human umbilical vein endothelial cells (HUVECs, Technoclone, Vienna, Austria) were cultured in endothelial cell growth medium (ECM) supplemented with 100 U/ml penicillin, 100 µg/ml streptomycin, 0.25 µg/ml fungizone, 2 mM L-glutamine, 5 U/ml heparin, 30-50 µg/ml endothelial cell growth supplement (Technoclone, Vienna, Austria). All cells were passaged by typsination and seeded into 6 well culture dishes at cell densities of $1 \times 10^6$ cells per well; at 37° C., 5% (v/v) $CO_2$.

Scratch Assay

Cells were seeded at $1 \times 10^6$ cells per well in 6 well plates (Nalge Nunc) and allowed to attached overnight prior to 24 hr incubations with hydroxytyrosol-containing formulation 1, 2 or 3 (Table 9). In separate experiments, cells were treated with 30 mM glucose for 3 days prior to one day incubation in fresh media and then 24 hour incubation with the Formulation before scratching. Experiments to determine the protection of cells following doxorubicin treatment involved treatment with the McCord formulation or individual components for 24 hours prior to 1 hour incubation with 1 µM doxorubicin. Cells were washed and incubated for a further 24 hours in fresh media before scratching. Cells were then scratched by scraping the cell monolayer in a straight line using a pipet tip. Cell debris was removed following three washes with PBS (without $Ca^{2+}$ and $Mg^{2+}$) and the growth media was replaced. The cells were incubated at 37° C., 5% (v/v) $CO_2$ and images were acquired at time intervals between 0-200 hours. Cell migration was determined by measuring the gap distance between the two most inner cells from the scratch line using Fiji, Image J (version 1.4).

Angiogenesis (Vascular Tube Formation) Assay

Human umbilical vein endothelial cells were seeded at 50,000 cells per well in a 48 well, flat bottom culture plate (Nalge Nunc) and allowed to attached overnight. Cells were treated with Formulation 2, dilution factor=4) for 24 hours prior to typsination by 0.05% trypsin EDTA. The cells were seeded at 10,000 cells per well in the ibidi µ-treat angiogenesis culture slide (Ibidi, Martinsried, Germany) coated with 0.8% agarose culture medium mix according to the manufacturer's protocols. Cells were imaged immediately (0 hours) and consecutively every 3 hours, using an Olympus CKX41, (Tokyo, Japan) light microscope using a 10× objective. Tube length was analyzed in Image J (Fiji; version 1.4) according the manufacturers analyses protocols.

Total Antioxidant Capacity Assay

Human peripheral blood mononuclear cells were seeded at $1 \times 10^6$ cells per well in 12 well culture plates (Nalge Nunc) with Formulation 2 (dilution factor=4) (Table 9), 50 µM hydroxytyrosol or 200 µM Oleuropein for 24 hours; 37° C., 5% (v/v) $CO_2$. In separate experiments, cells were treated with 30 mM glucose for 72 hours prior to 24 hours incubation in fresh media and then a 24 hour incubation with the hydroxytyrosol-containing formulation 2 (dilution factor=4); 37° C., 5% (v/v) $CO_2$. Experiments to determine the protection of cells following doxorubicin treatment involved pre-treatment with Formulation 2 (dilution factor=4) for 24 hours prior to 1 hour incubation with 1 µM doxorubicin. Cells were washed and incubated for a further 24 hours in fresh media; 37° C., 5% (v/v) $CO_2$. Cells were harvested for their total protein by centrifugation at 1000×g for 10 minutes at 4° C. to pellet cell suspensions. Lysates were collected by sonication in iced water of the cell pellet in emerged in cold lysis buffer (5 mM potassium phosphate (pH 7.4), 0.9% sodium chloride, 0.1% glucose). Following centrifugation at 10,000×g for 15 minutes at 4° C., the supernatant was collected and Bradford assay was performed to determine protein concentration of each sample according the manufacturers protocols. Cell lysates were then used to perform the antioxidant assay kit (Cayman; cat: 709001, MI, USA) according the manufacturer's protocol. Cell lysates were analyzed for their total antioxidant capacity. This included the full array of enzymes, small molecules and macromolecules that the cell has developed to counteract ROS and reduce their damage together with any food-derived antioxidants. The sum of endogenous and food-derived antioxidants in the sample represented the total antioxidant activity of the cells and was measured by their ability to inhibit the oxidation of ABTS (2,2'-Azino-di-[3-ethylbenzthiazoline sulphonate]) in the presence of metmyoglobin using the Perkin Elmer Multi-plate reader (λem=750 nm). The capacity of the antioxidants in the sample to prevent ABST oxidation was compared with known millimolar concentrations of Trolox, a water-soluble tocopherol analogue and all values were adjusted according the known amounts of protein present per sample.

Results and Discussion

Figure 21A:
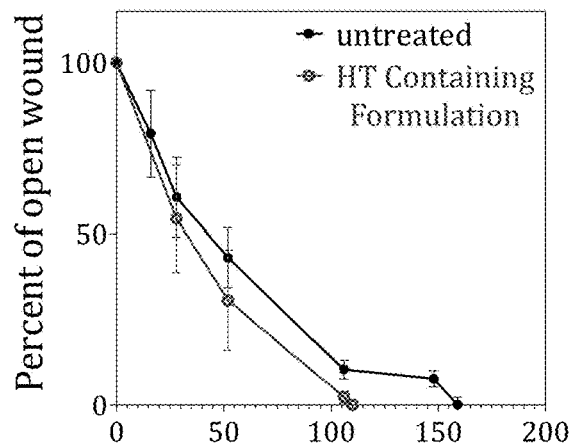
FIG. 21 (A-C) shows improved migration of human keratinocytes following treatment with high glucose and doxorubicin in the presence of hydroxytyrosol according to an exemplary embodiment of the invention. (A) shows cell migration with or without treatment with hydroxytyrosol. (B) shows cell migration with or without treatment with hydroxytyrosol in the presence of doxorubicin. (C) shows cell migration with or without treatment with hydroxytyrosol in the presence of high glucose. Mean±standard deviations from a single experiment performed in duplicate are shown; total of 3 independent experiments tested.
Figure 21B:
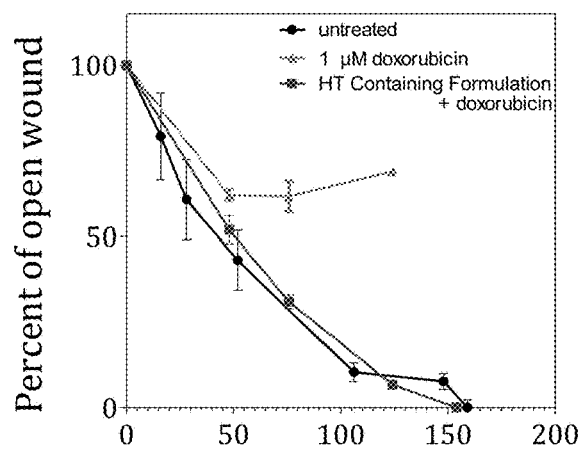
Figure 21C:
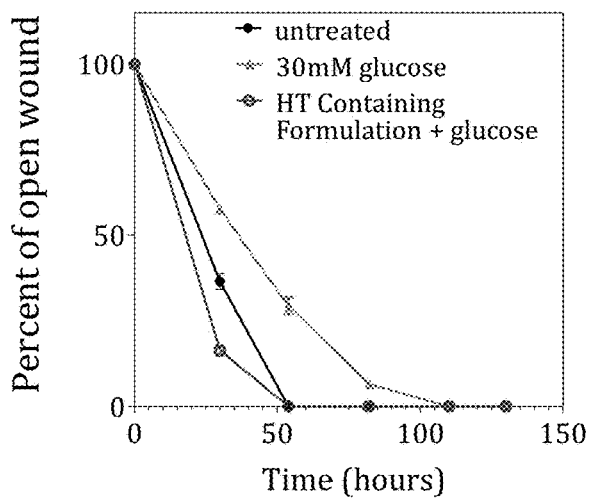
Figure 22A:
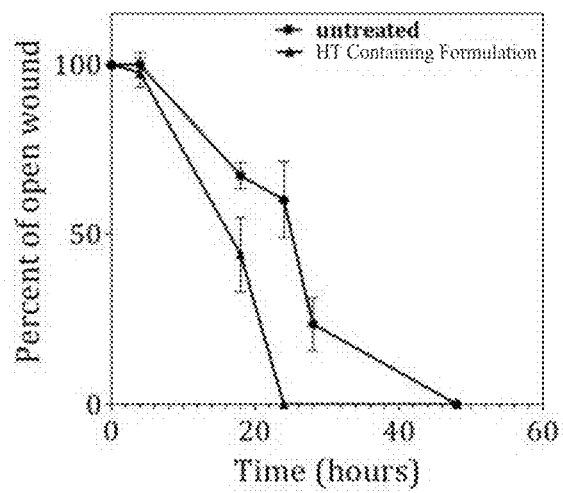
FIG. 22 (A-C) shows improved migration of human microvascular endothelial cells following treatment with high glucose and doxorubicin according to an exemplary embodiment of the invention. (A) shows cell migration with or without treatment with hydroxytyrosol. (B) shows cell migration with or without treatment with hydroxytyrosol in the presence of doxorubicin. (C) shows cell migration with or without treatment with hydroxytyrosol in the presence of high glucose. Mean±standard deviations from a single experiment performed in duplicate are shown; total of 3 independent experiments tested.
Figure 22B:
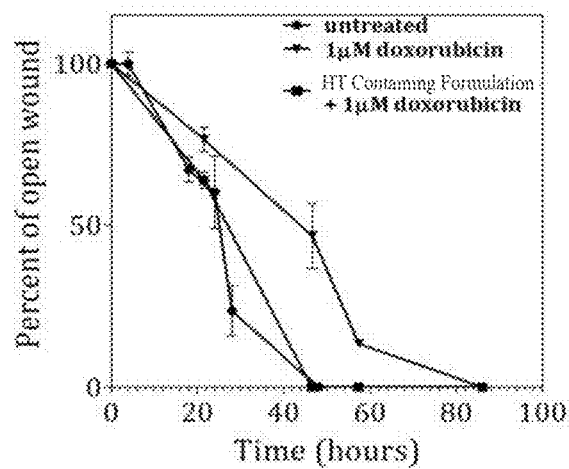
Figure 22C:
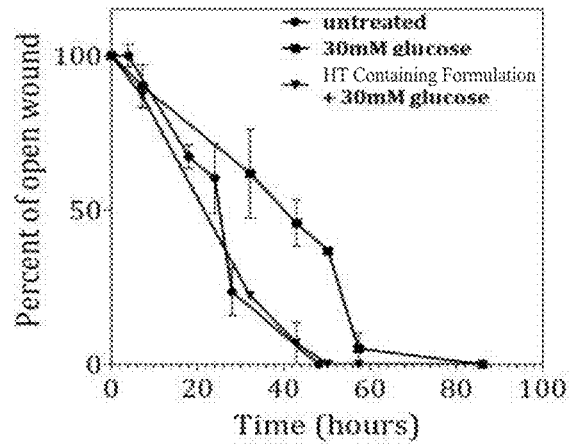
Figure 23A:
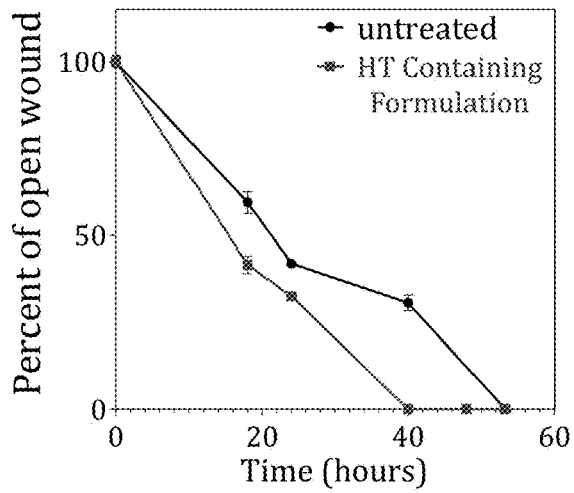
FIG. 23 (A-C) shows improved migration of human umbilical vein endothelial cells following treatment with high glucose and doxorubicin according to an exemplary embodiment of the invention. (A) shows cell migration with or without treatment with hydroxytyrosol. (B) shows cell migration with or without treatment with hydroxytyrosol in the presence of doxorubicin. (C) shows cell migration with or without treatment with hydroxytyrosol in the presence of high glucose. Mean±standard deviations from a single experiment performed in duplicate are shown; total of 3 independent experiments tested.
Figure 23B:
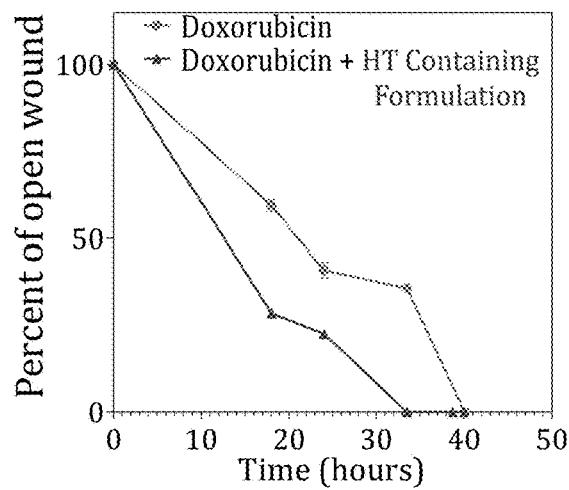
Figure 23C:
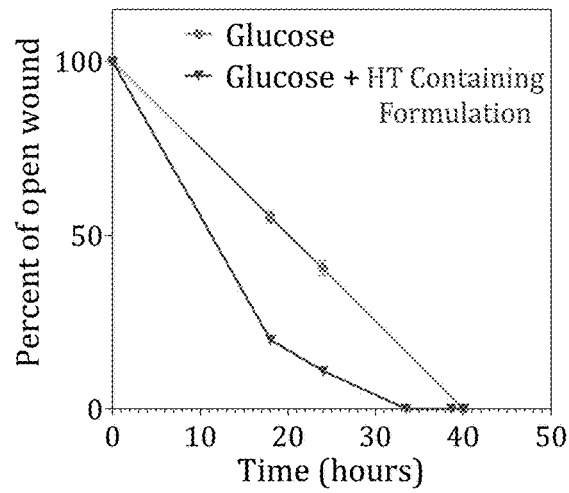

Our findings indicate that the hydroxytyrosol-containing formulations of the present invention accelerate the migration of human keratinocytes (FIG. 21), HMEC-1 (FIG. 22) and HUVEC cells (FIG. 23) cells following physical wounding. To simulate endothelial dysfunction associated with diabetic complications, cells were pre-treated with 30 mM glucose for 3 days prior to wounding. The findings indicated that glucose prolonged the time required for 50% of the wound to heal significantly. The hydroxytyrosol-containing formulation had a pronounced protective effect on glucose-induced endothelial cell dysfunction, returning the time required to heal 50% of the wound to that similar to untreated cells. Further, doxorubicin also induced endothelial cell dysfunction, increasing the time required for 50% of the wound to heal to in untreated cells. As observed, with the effects mediated by glucose, the hydroxytyrosol-containing formulation exhibited a pronounced protective effect. Treatment with the hydroxytyrosol-containing formulation improved the wound healing response to that similar of the untreated cells.

Figure 25A:
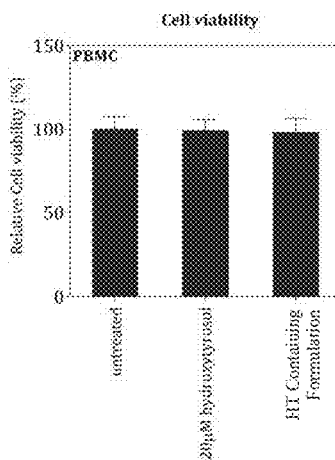
FIG. 25 (A-F) shows hydroxytyrosol and hydroxytyrosol-containing formulation 2 (4× diluted; see Table 9) improve total antioxidant capacity in PBMC (C) and deplete antioxidant capacity of chronic myeloid leukemic K562 cells (F). In K562 cells (D, E), hydroxytyrosol and hydroxytyrosol-containing formulation 2 (4× diluted) reduce the cells viability (D) and initiates caspase 3/7 mediated apoptosis (E), these effects are not observed in the normal PBMC cells (A, B). Mean±standard deviations from a single experiment performed in triplicate are shown; total of 2 independent experiments tested. The level of significance was accepted at $*p<0.05$, $p<0.01$, $*p<0.001$ and $****p<0.0001$.
Figure 25B:
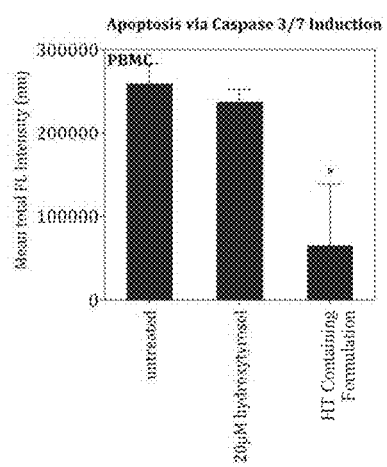
Figure 25C:
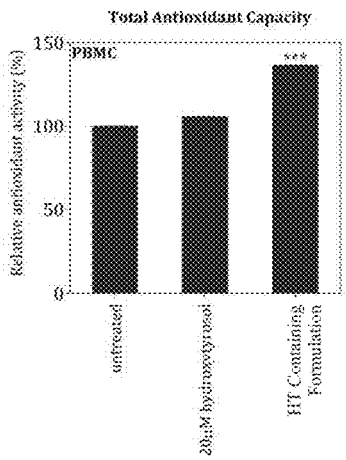
Figure 25D:
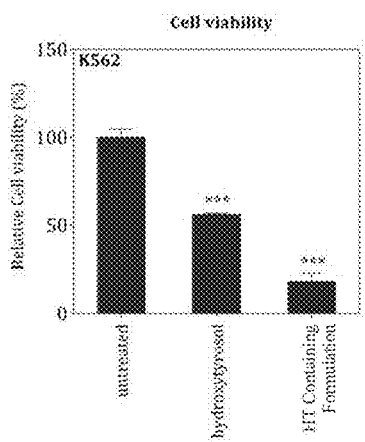
Figure 25E:
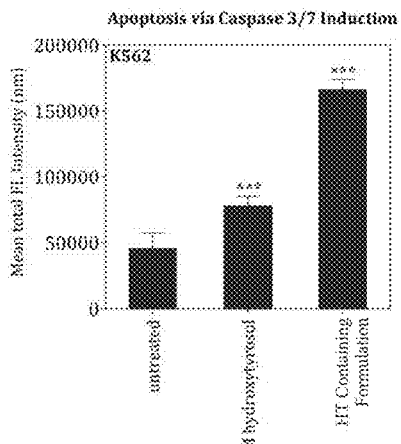
Figure 25F:
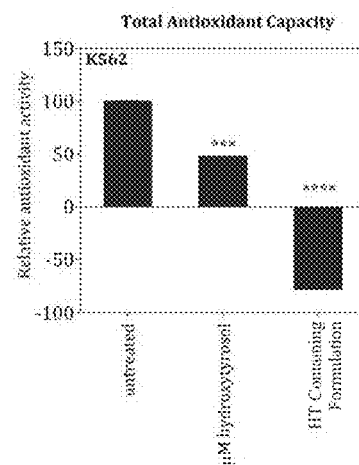
Figure 26A:
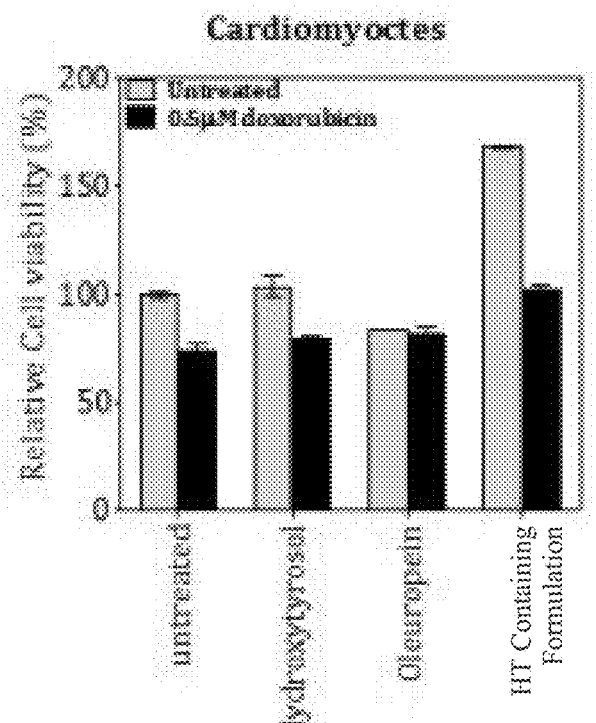
FIG. 26 (A-D) shows the protective effects of polyphenolic compounds according to an exemplary embodiment of the invention in models of muscle damage. (A) shows cell viability in cardiomyocytes with or without treatment with hydroxytyrosol in the presence or absence of doxorubicin. (B) shows viability in embryonic cardiac myoblasts with or without treatment with hydroxytyrosol in the presence or absence of doxorubicin. (C) shows viability in smooth muscle cells with or without treatment with hydroxytyrosol in the presence of doxorubicin. (D) shows viability in skeletal muscle cells with or without treatment with hydroxytyrosol in the presence or absence of doxorubicin or hydrogen peroxide.
Figure 26B:
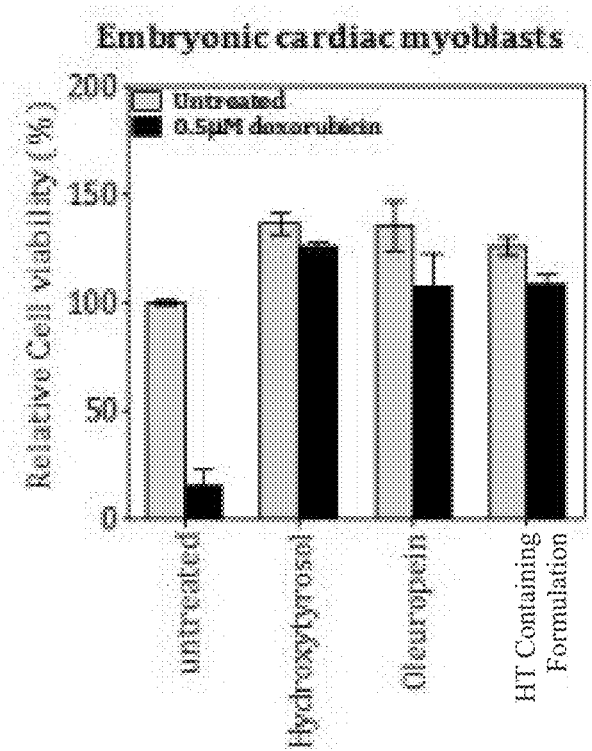
Figure 26C:
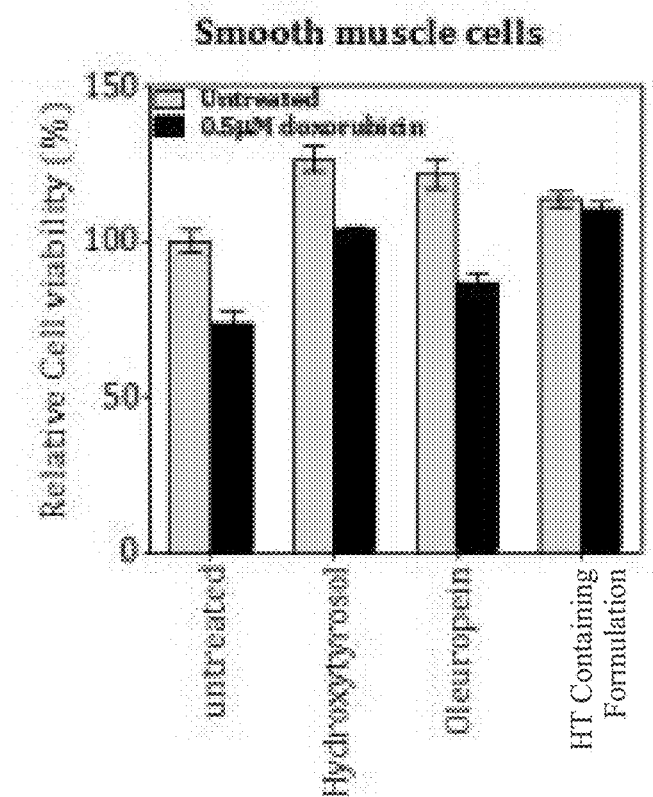
Figure 26D:
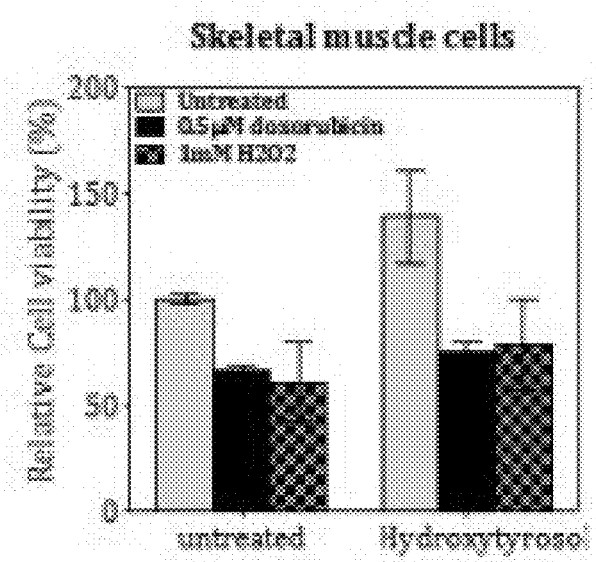

Following investigations of total antioxidant capacity in PBMCs and K562 cells, the results show hydroxytyrosol and hydroxytyrosol-containing formulation 2 deplete total antioxidant capacity of the chronic myeloid leukemic cells and enhance the antioxidant capacity of the normal peripheral blood mononuclear cells (FIG. 25E). Furthermore, this trend is reflected in the relative cell viability of the cells. Hydroxytyrosol and hydroxytyrosol-containing Formulation 2 were found to significantly induce caspase 3/7 mediated apoptosis in malignant K562 cells.

Figure 24:
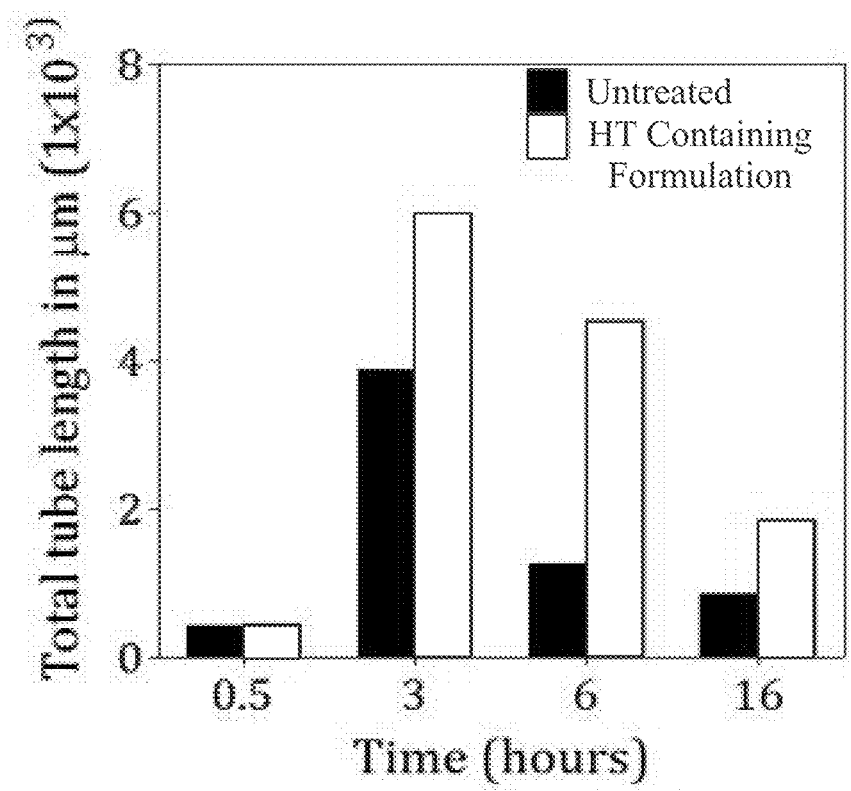
FIG. 24 shows improved angiogenesis (vascular tube formation) in human umbilical vein endothelial cells according to an exemplary embodiment of the invention. Mean±standard deviations from a single experiment performed in triplicate are shown; total of 2 independent experiments tested.

Furthermore, the results show hydroxytyrosol-containing Formulations of the present invention increased tubule formation in HUVEC cells and had a prolonged effect in increased tube length up to 16 hours (FIG. 24). Following investigations of total antioxidant capacity in PBMCs, the results show Hydroxytyrosol, Oleuropein and formulations containing both Hydroxytyrosol and Oleuropein significantly increased the total antioxidant of the cells. In addition, hydroxytyrosol-containing formulations restored the depleted antioxidant capacity of normal peripheral blood mononuclear cells induced by stress with high glucose and doxorubicin (FIG. 25). The mRNA sequence and microarray analysis results in Table 7 are further summarized in Example 10, Table 8 below.

Table 7. Overview of the effects of hydroxytyrosol-containing formulations on wound healing parameters in vitro investigations.

Example 10

Effects of Hydroxytyrosol, Oleuropein and Hydroxytyrosol-Containing Formulations in Models of Muscle Damage Summary:

Phenolic compounds in olive, hydroxytyrosol and oleuropein and hydroxytyrosol-containing formulations protect muscle cells from damage.

Methods

Cell Culture

Clonal embryonic ventricular H9c2 myoblasts that have been isolated from BDIX rat heart tissue and obtained from the European Culture Collection and grown in culture flasks in Dulbecco's modified Eagle's medium (DMEM, Gibco®, Invitrogen, Carlsbad, USA) supplemented with 10% fetal bovine serum (FBS, In Vitro Technologies, Victoria, Australia), antibody/antimycotic containing 100 U/mL Penicillin, 100 μg/mL Streptomycin, 0.25 μg/mL Amphotericin B (Invitrogen, Carlsbad, Calif., USA). The cells were incubated at a humidified atmosphere at 37° C., 5% $CO_2$. To induce myogenic transdifferentiation, cells were cultured in DMEM containing 1% FBS for up to 9 days with the culture media replaced every two days. To induce cardiogenesis, cells were cultured in DMEM containing 1% FBS in the presence of 10 nM all-trans retinoic acid (Sigma-Aldrich, St. Luis, Mo., USA) for 7 days with the culture medium replaced daily. The murine skeletal myocyte cell line C2C12 and the murine smooth muscle cell line SMC, were grown in low-glucose DMEM and 10% FBS maintained at 37° C. and 5% $CO_2$ according to the recommendations of American Type Culture Collection. To induce differentiation, the C2C12 myocytes were grown to 90% confluence before switching to a 2% FBS differentiation medium for 7 days, with a daily media change.

Cell Viability and Apoptosis

Cells were pre-treated with hydroxytyrosol (dilution factor 1=200 μM), oleuropein (dilution factor 1=50 μM) and hydroxytyrosol-containing Formulation 2 (dilution factor 4) (Table 9) for 24 hours; 37° C., 5% (v/v) $CO_2$. In separate experiments, cells were treated with hydroxytyrosol-containing formulation 2 (dilution factor 4) for 24 hours prior to 24 hour incubation with 1 mM $H_2O_2$ or 0.5 μM doxorubicin; 37° C., 5% (v/v) $CO_2$. Cell viability was measured using the Cell-Titer Blue® Assay kit (Promega, Madison, Wis., USA) as previously described.

TABLE 7

Overview of the effects of hydroxytyrosol-containing formulations on wound healing parameters in vitro investigations.

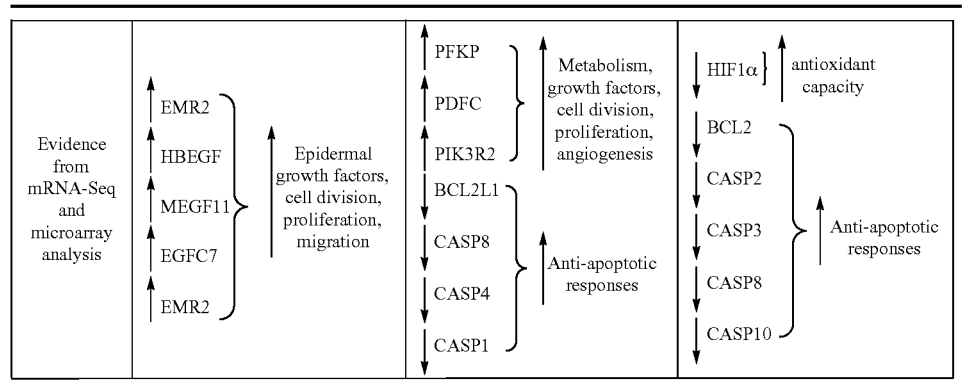

Results and Discussion

Our findings indicate that the hydroxytyrosol-containing Formulation of the invention stimulated proliferation of embryonic cardio myoblasts, cardiomyocytes and smooth muscle cells. In addition, the hydroxytyrosol-containing Formulation of the invention displayed protective effects in prevented doxorubicin induced cell damage to the embryonic cardio myoblasts, cardiomyocytes and smooth muscle cells. Furthermore, antioxidants hydroxytyrosol and oleuropein displayed similar effects in all muscle cell lines (FIG. 26).

Example 11

Table 8 below summarizes the epigenetic effects induced by hydroxytyrosol according to an exemplary embodiment of the invention. The listed genes correspond to the evidence from mRNA sequence and micro-array analysis set out in Table 7.

TABLE 9

Concentrations of components of the hydroxytyrosol-containing formulations tested.

| | Compound | | |
|---|---|---|---|
| | F1 | F2 | F3 |
| Hydroxytyrosol (μM) | 200 | 80 | 80 |
| Oleuropein (μM) | 800 | 320 | 320 |
| N-acetylcysteine (mM) | 8 | 8 | 8 |
| L-proline (μM) | 200 | 200 | 400 |
| Glycine (mM) | 8 | 8 | 20 |
| Taurine (μM) | 400 | 400 | 800 |

Example 12

Effect of Hydroxytyrosol on Genes Related to Glucose Metabolism

Summary:

Typically normal cells metabolize glucose by glycolysis and oxidative phosphorylation. In contrast, even in the

TABLE 8

Epigenetic Profile induced by hydroxytyrosol-containing formulations

| Gene* | Function | HT-containing Formulation Effect on Gene |
|---|---|---|
| LSD1 | Silent in normal human cells but it activated in 90% of all human cancers. LSD1 is believed to regulate the expression of genes by serving as a catalyst for the demthylation of mono- and di-methylated histones H3-K4 or K9. | Hydroxytyrosol is a potent Inhibitor of the LSD1 gene |
| EMR2 | Expresses the EMR2 protein that promotes cell-to-cell adhesion by interacting with chondroitin sulfate chains | Up regulated in epidermal keratinocytes |
| HBEGF | Required for normal heart function and heart valve development may be involved in macrophage mediated cellular proliferation. | Up-regulated in epidermal keratinocytes |
| MEGF11 | Provides a mechanism by which the cell mechanism is for the different cell types to be distributed evenly across the surface of the retina. | Up-regulated in epidermal keratinocytes |
| EGFC7 | Creates a protein that is a potent mitogenic factor that plays an important role in the growth, proliferation and differentiation of numerous cell types. Dysregulation of this gene has been associated with the growth and progression of certain cancers. | Up-regulated in epidermal keratinocytes |
| PFKP | Serves as a catalyst for the third step of glycolysis. | Up-regulated in human microvascular endothelial cells |
| PDFC | Binds to activated (phosphorylated) protein-tyrosine kinases, through its SH2 domain and acts as an adaptor mediating the association of the P110 catalytic unit to the plasma membrane. | Up-regulated in Human microvascular endothelial cells |
| PIK3R2 | Promotes the production of secondary messengers important in growth signaling pathways | Up-regulated in human microvascular endothelial cells |
| BCL2L1 | acts as a potent inhibitor of cell-death. Acts as a potent inhibitor of cell death. Acts as a regulator of G2 checkpoint and progression to cytokinesis during mitosis. | Down-regulated in human microvascular endothelial cells |
| Caspases 8, 4, 1 | family has been implicated in the pathogenesis of many diseases including stroke, Alzheimer's disease, myocardial infarction, cancer, and inflammatory disease. | Down-regulated in human microvascular endothelial cells |
| HIF1α | Plays an essential role in embryonic revascularization, tumor angiogeneisis and pathogenesis and pathophysiology of Ischemic disease. | Up-regulated in Peripheral Mononuclear Blood Cells |
| BCL2 | Encodes an integral outer mitochondrial membrane protein that blocks the apoptotic death of some cells such as lymphocytes. | Down regulated in Peripheral Mononuclear Blood Cells |
| Caspases 2, 3, 8, 10 | The CASP family has been implicated in the pathogenesis of many diseases including stroke, Alzheimer's disease, myocardial infarction, cancer, and inflammatory disease. | Down-regulated in Peripheral Mononuclear Blood Cells |

*All functions have been derived from NCBI's Gene database presence of oxygen, proliferating and cancer cells exhibit an increased uptake of glucose and increased rate of glycolysis and predominantly undergo lactic acid fermentation. This phenomenon is known as the Warburg effect in honor of Otto Warburg who first made these observations in the 1920s. After a period of general lack of interest, the field has recently become an intense focus of research. Indeed it is becoming evident that there is a strong correlation between gene expression and cancer metabolism. These studies utilized mRNA-Sequencing and explored a "Warburg gene-set" which was derived from the publicly available Cell Signaling Technology pathway map. The following were evaluated: (1) changes in the expression of Warburg-related genes in human erythroleukemic compared to normal peripheral blood mononuclear cells and (2) the effects of incubation of K562 cells on relevant genes.

Methods

Cell Culture

Human chronic myelogenous leukemia K562 cells were obtained from the American Type Culture Collection (Manassas, Va., USA) and maintained in complete-Royal Park Memorial Institute (RPMI) 1640 medium supplemented with 20 mmol/L HEPES (pH 7.4; GIBCO-Invitrogen, Carlsbad, Calif., USA), 10% (v/v) fetal bovine serum (FBS), 2 mmol/L L-glutamine (GIBCO-Invitrogen), and 80 units gentamicin (GIBCO-Invitrogen). Cells were cultured in suspension in a humidified atmosphere of 5% (v/v) $CO_2$ at 37° C. and were maintained in exponential growth phase. For maintenance, cells were passaged twice per week and seeded at ratios 1:10. Human peripheral blood mononuclear cells (PBMCs) were fractionated using the Ficoll Plaque fractionation method from whole blood obtained from the Australian Red Cross Blood Bank (ARCB) under ethic approval (#304/12). Cells were harvested fresh on the day of the experiments and maintained in complete-RPMI-1640 medium supplemented with 10% FBS, 2 mM L-glutamine and 20 µg/mL gentamicin at 37° C., 5% (v/v) $CO_2$.

mRNA-Sequencing

Cells were seeded at densities of $1\times10^6$/mL in culture flasks (Nalge Nunc, New York, USA) and K562 cells were treated with or without 100 µM hydroxytyrosol for 24 hours at 37° C., 5% (v/v) $CO_2$. mRNA sequencing was performed by TRIZOL extraction and library preparation using Illumina kits according to manufacturer's protocols. Next generation sequencing (NGS) was performed at a depth of approximately 20 million mapped reads per sample. Reads generated by the Illumina base calling software V1.6 were aligned with Burrows Wheeler Aligner to the human transcriptome database curated by RefSeq (Hg18 build). Raw counts were normalized to adjust for slightly differing data volume across lanes giving the widely used score reads per transcript per million reads. These scores were used to determine relative fold changes and the conventionally used ±1.5 fold-change, which is discernible with qRT-PCR, was defined a significant change in expression. The online program MetaCore (GeneGo Inc. St. Joseph, MI, USA) was used for pathway analysis. The Warburg gene-set shown in Table 10 was used to investigate changes in Warburg-related genes in human erythroleukemic compared to normal peripheral blood mononuclear cells and changes in expression of Warburg-related genes following incubation of K562 cells with hydroxytyrosol.

Results and Discussion

Previous in vitro investigations indicate that hydroxytyrosol induces cell-death and apoptosis preferentially in malignant cells compared to normal cells. Using genome wide next generation sequencing (mRNA-Seq) analysis, this study investigated the Warburg-related gene expression changes in erythroleukemic K562 cells compared to normal PBMC cells and K562 cells treated with 100 µM hydroxytyrosol (Table 10). As anticipated, the findings indicate that 51 genes of the total of 134 Warburg-related genes (38%) were significantly regulated in K562 cells compared to PBMC. Pre-treatment of cells with hydroxytyrosol resulted in differential expression of 30% of these genes; with 87% reversing expression towards that observed in PBMC cells. In accordance with the experimental data a pro-apoptotic effect was observed following treatment with hydroxytyrosol. Preliminary interrogation of the data shows significant up-regulation in the tumor suppressor gene TP53 (tumor protein p53; 1.91 fold change) and the TP53-induced glycolysis and apoptosis regulator C12orf5 (chromosome 12 open reading frame 5) in K562 cells following treatment with hydroxytyrosol. In addition, a strong pro-apoptotic affect was observed via the up-regulation of caspases 4, 7 and 8 and the p53 up-regulated modulator of apoptosis BCL2 binding component 3 (BBC3), by a fold change of 1.87, 2.01, 1.62, and 2.29 respectively. Further, metabolic regulators PFKFB4 (6-phosphofructo-2-kinase/fructose-2, 6-biphosphatase 4), PFKB2 (6-phosphofructo-2-kinase/fructose-2,6-biphosphatase 2) and ACLY (ATP citrate lyase) were down-regulated by 1.79, 1.53 and 1.59 fold change respectively (Table 10). Importantly, down-regulation of the iron-transporter (transferrin receptor 2; TRF2), which is involved in iron hemostasis, growth and proliferation, was significantly down-regulated by hydroxytyrosol (1.9-fold).

TABLE 10

Warburg-related gene expression changes in erythroleukemic K562 cells compared to normal PBMC cells and K562 cells treated with 100 µM hydroxytyrosol.

| | | Fold Change | |
| --- | --- | --- | --- |
| Gene Symbol | Gene Name | K562 vs. PBMC | K562 + 100 µM HT |
| Up-regulated | | | |
| ME1 | malic enzyme 1, NADP(+)-dependent, cytosolic | 14.62 | 2.22 |
| TFR2 | transferrin receptor 2 | 12.15 | −1.90 |
| VEGFA | vascular endothelial growth factor A | 9.92 | 2.65 |
| SLC1A5 | solute carrier family 1 (neutral amino acid transporter), member 5 | 7.69 | |
| HK1 | hexokinase 1 | 7.57 | |
| PIK3CB | phosphoinositide-3-kinase, catalytic, beta polypeptide | 7.09 | |

TABLE 10-continued

Warburg-related gene expression changes in erythroleukemic K562 cells compared to normal PBMC cells and K562 cells treated with 100 μM hydroxytyrosol.

| Gene Symbol | Gene Name | Fold Change K562 vs. PBMC | K562 + 100 μM HT |
|---|---|---|---|
| SLC25A5 | solute carrier family 25 (mitochondrial carrier; adenine nucleotide translocator), member 5 | 6.93 | |
| VDAC1 | voltage-dependent anion channel 1 | 5.91 | |
| SREBF1 | sterol regulatory element binding transcription factor 1 | 5.71 | −1.69 |
| PFKFB2 | 6-phosphofructo-2-kinase/fructose-2,5-biphosphatase 2 | 5.70 | −1.53 |
| FGF11 | fibroblast growth factor 11 | 5.44 | |
| PDHX | pyruvate dehydrogenase complex, component X | 5.14 | |
| PFKM | phosphofructokinase, muscle | 4.71 | |
| VDAC3 | voltage-dependent anion channel 3 | 4.46 | |
| LDHA | lactate dehydrogenase A | 4.13 | |
| BCL2L1 | BCL2-like 1 | 4.03 | |
| ACLY | ATP citrate lyase | 3.94 | −1.60 |
| PRKAB1 | protein kinase, AMP-activated, beta 1 non-catalytic subunit | 3.50 | |
| MTOR | mechanistic target of rapamycin (serine/threonine kinase) | 2.56 | |
| PFKP | phosphofructokinase, platelet | 2.55 | |
| MYC | v-myc myelocytomatosis viral oncogene homolog (avian) | 2.24 | |
| HK2 | hexokinase 2 | 2.14 | |
| CASP9 | caspase 9, apoptosis-related cysteine peptidase | 2.07 | |
| PIK3R2 | phosphoinositide-3-kinase, regulatory subunit 2 (beta) | 2.07 | |
| SLC25A4 | solute carrier family 25 (mitochondrial carrier; adenine nucleotide translocator), member 4 | 1.96 | |
| PDHB | pyruvate dehydrogenase (lipoamide) beta | 1.92 | |
| PFKFB4 | 6-phosphofructo-2-kinase/fructose-2,6-biphosphate 4 | 1.73 | −1.79 |
| CASP3 | caspase 3, apoptosis-related cysteine peptidase | 1.71 | |
| CASP6 | caspase 6, apoptosis-related cysteine peptidase | 1.62 | |
| PIK3R4 | phosphoinositide-3-kinase, regulatory subunit 4 | 1.59 | |
| PIK3C3 | phosphoinositide-3-kinase, class 3 | 1.51 | |
| SLC2A3 | solute carrier family 2 (facilitated glucose transporter), member 3 | 1.51 | |
| Down-regulated | | | |
| ME2 | malic enzyme 2, NAD(+)-dependent, mitochondrial | −1.71 | |
| BAD | BCL2-associated agonist of cell death | −1.85 | |
| BAX | BCL2-associated X protein | −1.89 | |
| SLC1A4 | solute carrier family 1 (glutamate/neutral amino acid transporter), member 4 | −2.17 | 4.28 |
| BCL2 | B-cell CLL/lymphoma 2 | −2.23 | |
| PIK3C2B | phosphoionositide-3-kinase, class 2, beta polypeptide | −2.53 | |
| APAF1 | apoptotic peptidase activating factor 1 | −2.75 | |
| HIF1A | hypoxia inducible factor 1, alpha subunit (basic helix-loop-helix transcription factor) | −3.08 | |
| CASP7 | caspase 7, apoptosis-related cysteine peptidase | −3.40 | 2.27 |
| PIK3R1 | phosphoinositide-3-kinase, regulatory subunit 1 (alpha) | −4.81 | |
| PFKFB3 | 6-phosphofructo-2-kinase/fructose-2,6-biphosphatase 3 | −4.94 | |
| PDK3 | pyruvate dehydrogenase kinase, isozyme 3 | −5.46 | |
| BBC3 | BCL2 binding component 3 | −5.98 | 2.66 |
| CASP8 | caspase 8, apoptosis-related cysteine peptidase | −8.30 | 1.62 |
| C12orf5 | chromosome 12 open reading frame 5 | −8.71 | 3.57 |
| SLC2A6 | solute carrier family 2 (facilitated glucose transporter), member 6 | −12.23 | |
| PIK3CD | phosphoionositide-3-kinase, catalytic, delta polypeptide | −12.42 | |
| TP53 | tumor protein p53 | −19.68 | 2.30 |
| FGF18 | fibroblast growth factor 18 | −31.32 | |
| AKT3 | v-akt murine thymoma viral oncogene homolog 3 (protein kinase B, gamma) | −78.31 | 2.04 |
| CASP4 | caspase 4, apoptosis-related cysteine peptidase | −211.10 | 1.87 |

We claim:

1. A method of screening an individual or a cell of an individual for Lysine Specific Demethylase 1 (LSD1) linked cancer or pre-cancer comprising,
   a) administering to said individual or said cell a composition comprising hydroxytyrosol, a hydroxytyrosol derived and/or substituted compound, and/or a hydroxytyrosol metabolite selected from the group consisting of:
      (i) hydroxytyrosol that is isolated, purified and/or synthesized and has the following formula:

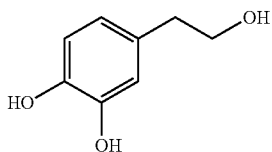

(ii) a hydroxytyrosol acyl derivative according to the following structure:

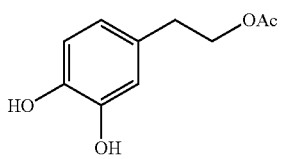

and
   (iii) hydroxytyrosol derived and/or substituted compound and/or hydroxytyrosol metabolite has

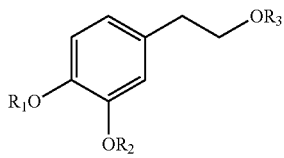

wherein R1, R2, and R3 provide a pharmaceutically acceptable salt, solvate, prodrug and/or isomer of hydroxytyrosol; and
   b) assaying for LSD1 linked cancer cell growth, proliferation and/or death; alteration of expression of an LSD1 gene; LSD1 linked cancer cell invasion, migration or adhesion and/or expression of LSD1 linked cancer cell markers in said individual or cell.

2. The method of claim 1, wherein said assay comprises assaying for inhibition of LSD1.

3. The method of claim 1 wherein R1, R2 and R3 are independently selected from the group consisting of hydrogen, substituted or unsubstituted alkyl, substituted or unsubstituted alkenyl, substituted or unsubstituted alkynyl, substituted or unsubstituted aryl, substituted or unsubstituted heterocyclyl, substituted or unsubstituted acyl, ORa, SRa, SORa, SO2Ra, OSO2Ra, OSO3Ra, NO2, NHRa, N(Ra)2, =N—Ra, N(Ra)CORa, N(CORa)2, N(Ra)SO2Ra, N(Ra)C(=NRa)N(Ra)Ra, CN, halogen, CORa, COORa, OCORa, OCOORa, OCONHRa, OCON(Ra)2, CONHRa, CON(Ra)2, CON(Ra)ORa, CON(Ra)SO2Ra, PO(ORa)2, PO(ORa)Ra, PO(ORa)(N(Ra)Ra) and aminoacid ester having inhibitory efficacy against the LSD1 protein; and further wherein each of the Ra groups is independently selected from the group consisting of hydrogen, substituted or unsubstituted alkyl, substituted or unsubstituted alkenyl, substituted or unsubstituted alkynyl, substituted or unsubstituted aryl, and substituted or unsubstituted heterocyclyl, substituted or unsubstituted acyl, and the like having inhibitory efficacy against the LSD1 protein; and further wherein each of the substituted or unsubstituted alkyl, alkenyl, alkynyl, aryl, heterocyclyl, and/or acyl groups are C1-28 (including all ranges therein).

4. The method of claim 1, wherein said method comprises administering said composition to an individual.

5. The method of claim 1, wherein said method comprises administering said composition to a cell.

6. The method of claim 1, comprising assaying for cell death.

7. The method of claim 1, comprising assaying for cell proliferation.

* * * * *